(12) United States Patent
Ingolia et al.

(10) Patent No.: US 6,180,361 B1
(45) Date of Patent: Jan. 30, 2001

(54) RECOMBINANT DNA EXPRESSION VECTORS AND DNA COMPOUNDS THAT ENCODE DEACETOXYCEPHALOSPORIN C SYNTHETASE AND DEACETYLCEPHALOSPORIN C SYNTHETASE

(75) Inventors: Thomas D. Ingolia; Stephen W. Queener; Suellen M. Samson, all of Indianapolis; Paul L. Skatrud, Greenwood, all of IN (US)

(73) Assignee: Eli Lilly and Company, Indianapolis, IN (US)

( * ) Notice: Under 35 U.S.C. 154(b), the term of this patent shall be extended for 0 days.

(21) Appl. No.: 07/283,429

(22) Filed: Dec. 12, 1988

Related U.S. Application Data

(63) Continuation-in-part of application No. 07/021,836, filed on Mar. 4, 1987, now abandoned.

(51) Int. Cl.[7] .............. C12N 15/13; C12N 9/02; C12N 15/67; C12N 15/80
(52) U.S. Cl. .............. 435/69.1; 435/47; 435/189; 435/252.3; 435/252.33; 435/254.11; 435/254.3; 435/254.4; 536/23.2; 536/24.1
(58) Field of Search .............. 435/69.1, 172.3, 435/252.3, 320, 252.33, 473, 34, 320.1, 47, 189, 254.11, 254.3, 254.4; 536/23.2, 24.1

(56) References Cited

U.S. PATENT DOCUMENTS

| | | | |
|---|---|---|---|
| 4,178,210 | 12/1979 | Demain et al. | 435/47 |
| 4,307,192 | 12/1981 | Demain et al. | 435/47 |
| 4,753,881 | 6/1988 | Yeh et al. | 435/183 |
| 4,762,786 | 8/1988 | Chapman, Jr. et al. | 435/172.3 |
| 4,874,703 * | 10/1989 | Jaskunas | 435/252.33 |
| 4,885,251 | 12/1989 | Ingolia et al. | 435/183 |
| 4,892,819 * | 1/1990 | Carr et al. | 435/69.1 |

FOREIGN PATENT DOCUMENTS

0191221A1  8/1986 (EP) .............. C12N/15/00

OTHER PUBLICATIONS

Felix et al., 1981, J. Antibiotics XXXIV (5):567.
Kupka et al., 1983, Can. J. Microbiol. 29:488.
Scheidegger et al., 1984, J. Antibiotics XXXVII (5):22.
Wolfe et al., 1984, Science 226:1386.
Minuth et al., 1982, Current Genetics 5:155.
Queener et al., 1985, Microbiology 1985:468.
Samson et al., 1985, Nature 318:191.
Martin and Liras, Trends in Biotech. 3(2):39.
Shen et al., 1986, Bio/Technology 4:61.
Hynes et al., 1983, Mol. Cell. Bio. 3(8):1430.
Turgeon et al., 1985, Mol. Gen. Genet. 201:450.
Hynes, 1986, Experimental Mycology 10:1.
Kupka et al., 1983, FEMS Microbiol. Lettrs. 16:1.
Beri, R.K., and Turner, G., Curr. Genet. 11, 639–641 (1987).*
Heim, J., et al., 1984, Applied Microbiology and Biotechnology 19: 232–236.*
Matsada, G., et al., 1981, FEBS Letters 126(1):111–113.*
Suggs, S., et al., 1981, Proc. Nat'l Acad. Sci USA 78(11):6613–6617.*
Ullrich, A., et al., 1984, The EMBO Journal 3(2):361–364.*

(List continued on next page.)

* cited by examiner

*Primary Examiner*—Ponnathapu Achutamurthy
*Assistant Examiner*—William Moore
(74) *Attorney, Agent, or Firm*—Ronald S. Maciak; Amy E. Hamilton

(57) ABSTRACT

The present invention provides DNA compounds that encode the expandase/hydroxylase enzyme of *Cephalosporium acremonium*. The compounds can be used to construct recombinant DNA expression vectors for a variety of host cells, including *E. coli*, Penicillium, and Cephalosporium.

53 Claims, 34 Drawing Sheets

Restriction Site and Function Map of Plasmid pPS56 (12.06 kb)

OTHER PUBLICATIONS

Levinson, A., et al, 1984, Journal of Molecular and Applied Genetics 2(6):507–517.*

Jensen, S.E., et al., 1985, The Journal of Antibiotics 38(2): 263–265.*

Leatherbarrow, R.J. and Fersht, A.R., 1986, Protein Engineering 1(1): 716.*

Zumstein, L. and Wang, J.C., 1986, Journal of Molecular Biology 191:333–340.*

Lathe, R., 1985, Journal of Molecular Biology, 183: 1–12.*

Hewick, R.M., et al., 1981, The Journal of Biological Chemistry, 256(15): 7990–7997.*

Kelly, J.M. and Hynes, M.J., 1985, The EMBO Journal, 4(2):475–479.*

Sanchez, F., et al., 1987, Gene, 51(1):97–102.*-

Restriction Site and Function Map of Plasmid pIT503**
(9700 bp)

Restriction Site and Function Map of Plasmid p1103
(6000 bp)

Restriction Site and Function Map of
Plasmid pIT160**
(5419 bp)

Restriction Site and Function Map of
Plasmid pCZR111**
(6395 bp)

Restriction Site and Function Map of
Plasmid pCZR336**
(6400 bp)

Restriction Site and Function Map of Plasmid pIT507
(8017 bp)

Restriction Site and Function Map of Plasmid p1104
(2700 bp)

Restriction Site and Function Map of Plasmid p1105
(3800 bp)

Restriction Site and Function Map of
Plasmid pIT511**
(7342 bp)

Restriction Site and Function Map of
Plasmid p1106
(3740 bp)

Restriction Site and Functon Map of Plasmid pIT512
(7222 bp)

Restriction Site and Function Map of
Plasmid p3SR2**

(9362 bp)

Restriction Site and Function Map of Plasmid pMLC12
(2671 bp)

Restriction Site and Function Map of Plasmid pPS34
(8655 bp)

Restriction Site and Function Map of Plasmid pPS51
(7661 bp)

Restriction Site and Function Map of Plasmid pPS52
(14661 bp)

Restriction Site and Function Map of Plasmid pPS53
(3671 bp)

Restriction Site and Function Map of
Plasmid pPS54
(10861 bp)

Restriction Site and Function Map of Plasmid pPS55 (5.06 kb)

Restriction Site and Function Map of Plasmid pPS56 (12.06 kb)

Restriction Site and Function Map of Plasmid pPS57 (5.36 kb)

Restriction Site and Function Map of Plasmid pPS58
(7963 bp)

Restriction Site and Function Map of Plasmid pPS59
(8000 bp)

Restriction Site and Function Map of Plasmid pPS60
(7342 bp)

Restriction Site and Function Map of Plasmid pPS61

Restriction Site and Function Map of Plasmid pPS62 (7.49 kb)

Restriction Site and Function Map of Plasmid pLC1
(5050 bp)

RECOMBINANT DNA EXPRESSION VECTORS AND DNA COMPOUNDS THAT ENCODE DEACETOXYCEPHALOSPORIN C SYNTHETASE AND DEACETYLCEPHALOSPORIN C SYNTHETASE

CROSS-REFERENCE

This application is a continuation-in-part of application Ser. No. 07/021,836, filed Mar. 4, 1987, now abondoned.

SUMMARY OF THE INVENTION

The present invention comprises a DNA sequence that encodes deacetoxycephalosporin C synthetase and deacetylcephalosporin C synthetase activities. Deacetoxycephalosporin C synthetase (DAOCS) catalyzes the reaction in which deacetoxycephalosporin C (DAOC) is formed from penicillin N and is often referred to as expandase. Deacetylcephalosporin C synthetase (DACS) catalyzes the formation of deacetylcephalosporin C (DAC) from DAOC, a hydroxylation reaction. These reactions are critical steps in the biosynthesis of important antibiotics, such as cephalosporins from *Cephalosporium acremonium* and 7α-methoxycephalosporins from *Streptomyces clavuligerus*.

The DNA compounds of the present invention encode the DAOCS and DACS in a single open reading frame. Transcription of this open reading frame, followed by translation of the resulting mRNA, yields a single polypeptide chain that possesses both DAOCS and DACS activities. Because of this dual nature of the compounds of the present invention, the terms "DAOCS/DACS," "DACS/DAOCS," "expandase/hydroxylase," and "EXP/HYD" are used to denote that a given gene, coding sequence, and enzyme possesses both DACS and DAOCS attributes. The linkage of these activities is not universally observed; for example, cephamycin-producing species of Streptomyces utilize two different polypeptides to express the DAOCS and DACS activities. Although concomitant expression of the DAOCS and DACS activities is convenient, and usually most preferred, it is not a critical aspect of the invention. Genetic engineering techniques, as exemplified herein, provide a ready means to separate the genetic information encoding DAOCS from DACS and so separately express either the DAOCS or DACS activity. Thus, the dual nature of the illustrative compounds, vectors, and enzymatic activities of the invention is not a limitation, for the invention also comprises single nature molecules: those that demonstrate only DACS or DAOCS attributes.

The DNA compound that encodes the DACS/DAOCS activities was isolated from *Cephalosporium acremonium* genomic DNA and used to construct recombinant DNA expression vectors. Three types of these expression vectors are especially useful: the first drives high-level expression of the DAOCS/DACS activities in *E. coli;* the second in *C. acremonium;* and the third in *Penicillium chrysogenum*.

The *E. coli*-produced DAOCS/DACS activities catalyze the formation of DAOC from penicillin N and DAC from DAOC. Crude cell extracts of these *E. coli* transformants of the invention exhibited DAOCS/DACS activities without any prior activation treatment. These *E. coli* expression vectors and transformants provide an efficient means for obtaining large amounts of active DAOCS/DACS enzyme. The DAOCS/DACS enzyme is useful not only for the production of DAOC and DAC but also for the expansion of penicillins other than penicillin N and hydroxylation of cephalosporins other than DAOC to form novel antibiotics.

The Cephalosporium vectors of the present invention are useful for purposes of constructing strains for use by the pharmaceutical industry. Cephalosporium is an economically important organism used to produce penicillin and cephalosporin antibiotics. Transformation of Cephalosporium with the expression vectors of this invention results in higher intracellular levels of DAOCS and DACS in the transformants. These transformants can be used to increase the efficiency of, and yield of antibiotic in, industrial fermentation.

The Penicillium vectors of the present invention are most useful to introduce cephalosporin synthesizing activities into high-level penicillin producing Penicillium strains. The DAOCS activity is useful for conversion of the various penicillins to cephalosporins, either alone or in conjunction with other activities, such as DACS or epimerase. For example, concomitant expression of isopenicillin N epimerase activity (from, e.g., *Cephalosporium acremonium*) and DAOCS activity in Penicillium leads to production of DAOC, a heretofore unknown metabolite in Penicillium.

The present invention also provides an improved method for introducing recombinant DNA molecules to Penicillium species. This novel transformation system utilizes the amdS gene of *Aspergillus nidulans*. Using acetamide ($CH_3CONH_2$) as the sole carbon or nitrogen source on transformation plates, one can select Penicillium host cells transformed with a vector containing the amdS gene from their untransformed counter-parts, which are unable to grow on the plates because wild-type Penicillium express no acetamidase activity.

The DNA compounds encoding DAOCS/DACS are readily modified to construct expression vectors that increase the efficiency and yield of fermentations involving other organisms, such as Paecilomyces and Streptomyces, especially *S. clavuligerus*. Although the DACS/DAOCS-encoding DNA of the present invention was isolated from *Cephalosporium acremonium*, this DNA can be used to construct vectors that drive expression of DACS/DAOCS in a wide variety of host cells, as illustrated by the *E. coli* expression vectors described above. The construction protocols utilized for the *E. coli*, Cephalosporium, and Penicillium vectors of the invention can be followed to construct analogous vectors for other organisms, merely by substituting, if necessary, the appropriate regulatory elements. Most organisms that produce penicillins and cephalosporins utilize the common precursor penicillin N, a substrate for DAOCS. The DACS/DAOCS-encoding DNA compounds of the present invention can be used to construct expression vectors useful for improving the efficiency and yield of fermentations involving a wide variety of penicillin and cephalosporin antibiotic-producing organisms.

The DNA compounds of the present invention are derived from genomic DNA of *Cephalosporium acremonium* and are significantly homologous in nucleotide sequence to the DNA compounds encoding DAOCS and/or DACS activity in other cephalosporin-producing organisms, such as *Streptomyces clavuligerus*. Because of this homology, the DACS/DAOCS-encoding DNA compounds of the present invention can be labelled and used to screen genomic libraries of organisms that produce cephalosporin C or similar compounds for the presence of either DACS or DAOCS-encoding DNA. Many organisms comprise DACS/DAOCS activity-encoding DNA that can be identified and isolated using the DNA compounds of the present invention, and the present invention comprises these equivalent, homologous DNA compounds.

The DACS/DAOCS-encoding DNA compounds of the present invention were isolated in conjunction with the regulatory sequences that control transcription and, ultimately, expression of the *Cephalosporium acremonium* DAOCS/DACS activities. The present invention comprises these novel regulatory sequences, which can be used, as disclosed herein, to drive transcription, translation, and expression of any gene product in Cephalosporium. These regulatory sequences are especially preferred for use in *C. acremonium*.

The present invention also comprises the regulatory signals of the DACS/DAOCS gene located at the 3' end of the coding strand of the coding region of the *Cephalosporium acremonium* DACS/DAOCS gene. These 3' regulatory sequences encode the transcription termination and mRNA polyadenylation and processing signals of the DACS/DAOCS gene. Placing these signals at the 3' end of the coding strand of the coding region of the gene to be expressed enhances expression of the desired gene product in Cephalosporium.

The following section provides a more detailed description of the present invention. For purposes of clarity and as an aid in the understanding of the invention, as disclosed and claimed herein, the following items are defined below.

amdS—an acetamidase gene; also used in the Figures to denote the *Asperigillus nidulans* acetamidase gene.

AmR—the apramycin resistance-conferring gene; also used to denote the apramycin-resistant phenotype.

Antibiotic—a substance produced by a micro-organism that, either naturally or with limited modification, will inhibit the growth of or kill another microorganism or eukaryotic cell.

Antibiotic Biosynthetic Gene—a DNA segment that encodes an activity necessary for an enzymatic reaction in the process of converting primary metabolites into antibiotics or converting one antibiotic compound into a different antibiotic compound.

Antibiotic-Producing organism—any organism, including, but not limited to, Streptomyces, Bacillus, Flavobacterium, Monospora, Cephalosporium, Paecilomyces, Podospora, Penicillium, and Nocardia, that either produces an antibiotic or contains genes that, if expressed, would produce an antibiotic.

Antibiotic Resistance-Conferring Gene—a DNA segment that encodes an activity that confers resistance to an antibiotic.

ApR—the ampicillin resistance-conferring gene; also used to denote the ampicillin-resistant phenotype. Note that ApS denotes the ampicillin-sensitive phenotype.

Bifunctional Cloning Shuttle Vector—a recombinant DNA cloning vector that can replicate and/or integrate into organisms of two different taxa.

bp—a base pair of double-stranded DNA.

CAT—the chloramphenicol resistance-conferring gene, which encodes an acetyltransferase.

cI857—a gene encoding a temperature sensitive repressor of the λpL promoter.

cIPS—isopenicillin N synthetase or isopenicillin N synthetase-encoding DNA from *Cephalosporium acremonium*.

Cloning—the process of incorporating a segment of DNA into a recombinant DNA cloning vector.

Coding sequence—the sequence of DNA in a gene that encodes either the amino acid residue sequence of the protein expressed by the gene or, in the case of rRNA or tRNA genes, the RNA sequence of the rRNA or tRNA expressed by the gene.

Coding strand—the "sense" strand, the single strand of a double-stranded coding sequence that is the complement of the "anti-sense" strand, which is the strand transcribed by RNA polymerase.

cos—phage λ cohesive end sequences.

Cosmid—a recombinant DNA cloning vector that can replicate in a host cell in the same manner as a plasmid but that can also be packed into phage heads.

DAC—deacetylcephalosporin C, the structure of which is depicted below:

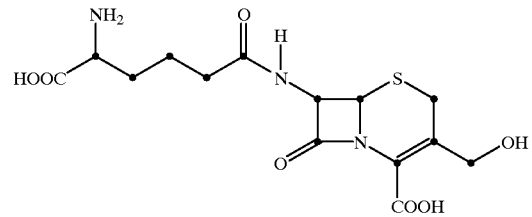

DACS—deacetylcephalosporin C synthetase, the enzymatic activity that catalyzes conversion of DAOC to DAC.

DAOC—deacetoxycephalosporin C, the structure of which is depicted below:

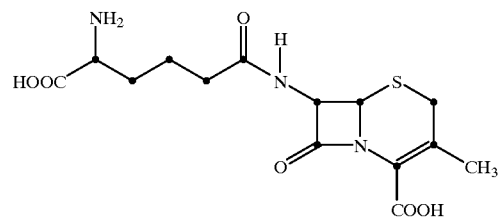

DAOCS—deacetoxycephalosporin C synthetase, the enzymatic activity encoded by the DAOCS gene, which catalyzes conversion of penicillin N to DAOC.

EkbGH—enterokinase-linker bovine growth hormone or DNA encoding same.

EXP/HYD—abbreviation for expandase/hydroxylase and used in the Figures herein to denote the location of DAOCS/DACS-encoding DNA.

Gene—a segment of DNA that comprises a promoter, translational activating sequence, coding sequence, and 3' regulatory sequences positioned to drive expression of the gene product, either a protein (and thus necessarily an mRNA), tRNA, or rRNA.

Genomic Library—a set of recombinant DNA cloning vectors into which segments of DNA, which substantially represent the entire genome of a particular organism, have been cloned.

hGH—human growth hormone or DNA encoding same.

HmR—the hygromycin resistance-conferring gene; also used to denote the hygromycin-resistant phenotype.

Hybridization—the process of annealing two homologous single-stranded DNA molecules to form a double-stranded DNA molecule that may or may not be completely base-paired.

IPS—isopenicillin N synthetase.

IPSp or cIPSp—the promoter and other 5' regulatory sequences of the *Cephalosporium acremonium* isopenicillin N synthetase (IPS) gene.

IPSt or cIPSt—the transcription termination, mRNA polyadenylation, and other 3' regulatory and processing signals of the *Cephalosporium acremonium* IPS gene.

Isopenicillin N Synthetase—an enzyme, also known as cyclase, that catalyzes the formation of isopenicillin N from δ-(L-α-aminoadipyl)-L-cysteinyl-D-valine.

KmR—the kanamycin resistance-conferring gene; also used to denote the kanamycin-resistant phenotype.

lacI—the *E. coli* lacI gene.

lacZα—the promoter and β-galactosidase (lacZ) α-fragment derived from the *E. coli* lac operon.

lppT—the transcription terminator of the *E. coli* lpp gene.

lppP—the promoter of the *E. coli* lpp gene.

M13 ORI—the origin of replication of phage M13.

mel—the tyrosinase gene.

MCS—a multiple-cloning site.

mRNA—messenger ribonucleic acid.

ORI—a plasmid or vector origin of replication, the DNA sequence that serves as an attachment or start site for DNA polymerase.

PGK—the promoter and other 5' regulatory sequences of the yeast *Saccharomyces cerevisiae* phosphoglycerate kinase gene.

pIPS—the IPS gene or IPS coding sequence of *Penicillium chrysogenum*.

pIPSp—the promoter of the IPS gene of *Penicillium chrysogenum*.

pL—the leftward promoter from bacteriophage lambda.

Promoter—a DNA sequence that promotes transcription of adjacent DNA.

rbs—ribosome-binding site, a sequence on the 5' end of an mRNA molecule that is encoded by a translational activating sequence and to which ribosomes can bind.

Recombinant DNA Cloning Vector—any autonomously replicating or integrating agent, including, but not limited to, plasmids, comprising a DNA molecule to which one or more additional DNA molecules can be or have been added.

Recombinant DNA Expression Vector—any autonomously replicating or integrating agent, including, but not limited to, plasmids, comprising a promoter and other 5' regulatory sequences positioned to drive expression of a DNA segment that encodes a polypeptide or RNA of research or commercial interest.

Recombinant DNA Sequence—Any DNA sequence, excluding the original chromosome from which the DNA sequence was derived, including, but not limited to restriction fragments and recombinant DNA vectors.

Recombinant DNA Vector—any recombinant DNA cloning or expression vector.

Restriction Fragment—any linear DNA molecule generated by the action of one or more enzymes.

rRNA—ribosomal ribonucleic acid.

Sensitive Host Cell—a host cell that cannot grow in the presence of a given antibiotic without a DNA segment that confers resistance thereto.

TcR—the tetracycline resistance-conferring gene; also used to denote the tetracycline-resistant phenotype. Note that TcS denotes the tetracycline-sensitive phenotype.

Transcription Terminator—a DNA sequence that acts to block transcription of DNA into RNA by RNA polymerase.

Transfectant—a recipient host cell that has undergone transformation by phage DNA or by DNA packaged into a phage particle.

Transformant—a recipient host cell that has undergone transformation.

Transformation—the introduction of DNA into a recipient host cell that changes the genotype and results in a change in the recipient cell.

Translational activating sequence—a 5' regulatory DNA sequence that, when transcribed into mRNA, promotes translation of mRNA into protein.

tRNA—transfer ribonucleic acid.

trp—the promoter and translational activating sequence of the tryptophan operon of *E. coli*.

BRIEF DESCRIPTION OF THE FIGURES

The restriction site and function maps presented in FIGS. 1–33 are approximate representations of the recombinant DNA vectors disclosed herein. The spacing of restriction sites on the map is proportional to the actual spacing of the restriction sites on the vector, but observed restriction site distances may vary somewhat from calculated map distances. The restriction site information is not exhaustive; therefore, there may be more restriction sites of a given type on the vector than actually shown on the map.

DETAILED DESCRIPTION OF THE INVENTION

Figure 1:
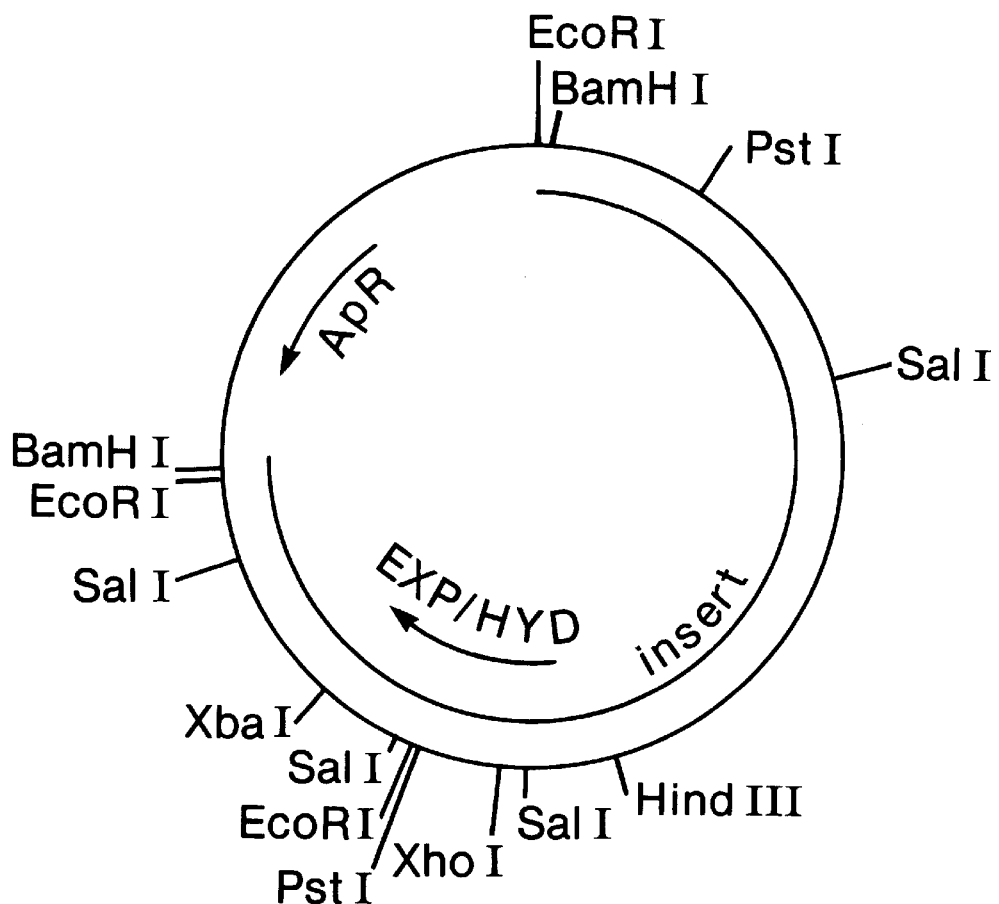
FIG. 1. Restriction site and function map of plasmid pIT503.

The present invention comprises DNA compounds and recombinant DNA cloning and expression vectors that encode DAOCS and DACS activity. These compounds provide for the expression of a single protein that expresses both activities or for a protein that expresses only one of the two activities. A particular DNA sequence, from the Brotzu strain of *Cephalosporium acremonium*, encoding both DACS and DAOCS activities is shown below. In the depiction, only the "sense" or coding strand of the double-stranded DNA molecule is shown, and the DNA is depicted from left to right in the 5'→3' orientation. The nucleotide sequence is numbered; the numbers appear above the DNA sequence. Immediately below each line of DNA sequence, the amino acid residue sequence of the synthetase encoded by the DNA is listed from left to right in the amino-terminus→carboxy-terminus direction. Each amino acid residue appears below the DNA that encodes it. The amino acid residue sequence is numbered; the numbers appear below the amino acid residue sequence.

```
                DNA Sequence of the DACS/DAOCS Gene
                (the expandase/hydroxylase gene) of
                     Cephalosporium acremonium 10          20          30          40
5'-A AGC TTG TAC GGA GAA TTA AGG CTT GCA CGA TTC CAT GGC GGT CTC 50          60          70          80          90
   GAC GAT CAG GGA CCA TGC ACG ATA CAT ATT CTC CTG CGA ACC AAG AAC 100         110         120         130         140
   GAG AAG AGA ACT CGA TGG CTT CTT ATG ATT CGT TGA CAA AAC TTC ACA 150         160         170         180         190
   AGA CAC TCG TGG GTT TAC AAT GCT ACA TTG ACG TGT GCG GCC AAG GCT 200         210         220         230
   GAG GGG AAG CAG GGC GTC ACT TAC GGC TAA GTA GCA GTT GTC TAA AAA 240         250         260         270         280
   GGA GTT CCT CGG CGT AAG CTA CGA GGT GGG GTT TGA GAT ATA TAT ATA 290         300         310         320         330
   CCG CTT TGA CAA CGT TTC GTT CTC ACT GGG ATC TTG TGA ATC CTT AAA 340         350         360         370         380
   TTC CTC TTG CAG AAC TTT CCT CCA CGC TAC TCC TCT CAA GTC ATC GCT 390         400         410         420         430
   CAA AAC CAC AGC ATC AAC ATG ACT TCC AAG GTC CCC GTC TTT CGT CTC
                               MET THR SER LYS VAL PRO VAL PHE ARG LEU
                                               5                    10

440         450         460         470
   GAC GAC CTC AAG AGC GGC AAG GTC CTC ACC GAG CTC GCC GAG GCC GTC
   ASP ASP LEU LYS SER GLY LYS VAL LEU THR GLU LEU ALA GLU ALA VAL
                       15                  20                  25

480         490         500         510         520
   ACC ACC AAG GGT ATC TTC TAC TTG ACC GAG AGC GGC CTG GTC GAC GAC
```

-continued

DNA Sequence of the DACS/DAOCS Gene
(the expandase/hydroxylase gene) of
*Cephalosporium acremonium*

```
THR THR LYS GLY ILE PHE TYR LEU THR GLU SER GLY LEU VAL ASP ASP
            30              35              40

530         540         550         560         570
GAC CAC ACC TCG GCG CGT GAG ACG TGC GTT GAC TTT TTC AAG AAC GGA
ASP HIS THR SER ALA ARG GLU THR CYS VAL ASP PHE PHE LYS ASN GLY
            45              50              55

580         590         600         610         620
AGC GAG GAG GAG AAG AGG GCC GTG ACG CTC GCC GAC CGT AAC GCC CGC
SER GLU GLU GLU LYS ARG ALA VAL THR LEU ALA ASP ARG ASN ALA ARG
        60              65              70

630         640         650         660         670
CGC GGC TTC TCT GCC CTC GAG TGG GAG AGC ACC GCC GTC GTC ACC GAG
ARG GLY PHE SER ALA LEU GLU TRP GLU SER THR ALA VAL VAL THR GLU
75              80              85              90

680         690         700         710
ACG GGC AAG TAC TCG GAC TAC TCG ACG TGC TAC TCC ATG GGC ATC GGC
THR GLY LYS TYR SER ASP TYR SER THR CYS TYR SER MET GLY ILE GLY
                95              100             105

720         730         740         750         760
GGC AAC CTG TTC CCG AAC CGG GGC TTC GAG GAC GTC TGG CAG GAC TAC
GLY ASN LEU PHE PRO ASN ARG GLY PHE GLU ASP VAL TRP GLN ASP TYR
            110             115             120

770         780         790         800         810
TTC GAC CGC ATG TAC GGC GCA GCC AAG GAT GTC GCG CGC GCC GTT CTC
PHE ASP ARG MET TYR GLY ALA ALA LYS ASP VAL ALA ARG ALA VAL LEU
            125             130             135

820         830         840         850         860
AAC TCT GTG GGC GCC CCG CTC GCC GGG GAG GAC ATT GAT GAC TTC GTC
ASN SER VAL GLY ALA PRO LEU ALA GLY GLU ASP ILE ASP ASP PHE VAL
        140             145             150

870         880         890         900         910
GAG TGC GAT CCC CTC CTC CGC CTA CGG TAC TTC CCC GAA GTG CCG GAG
GLU CYS ASP PRO LEU LEU ARG LEU ARG TYR PHE PRO GLU VAL PRO GLU
155             160             165             170

920         930         940         950
GAC CGC GTC GCC GAA GAG GAA CCC CTC CGC ATG GGA CCC CAC TAC GAC
ASP ARG VAL ALA GLU GLU GLU PRO LEU ARG MET GLY PRO HIS TYR ASP
                175             180             185

960         970         980         990         1000
CTA TCG ACC ATC ACG CTC GTG CAC CAG ACA GCC TGC GCC AAC GGC TTC
LEU SER THR ILE THR LEU VAL HIS GLN THR ALA CYS ALA ASN GLY PHE
            190             195             200

1010        1020        1030        1040        1050
GTG AGC CTG CAG TGC GAG GTG GAC GGA GAA TTC GTC GAC CTC CCG ACG
VAL SER LEU GLN CYS GLU VAL ASP GLY GLU PHE VAL ASP LEU PRO THR
            205             210             215

1060        1070        1080        1090        1100
CTC CCC GGC GCC ATG GTC GTC TTC TGC GGC GCG GTC GGC ACC CTG GCC
LEU PRO GLY ALA MET VAL VAL PHE CYS GLY ALA VAL GLY THR LEU ALA
        220             225             230

1110        1120        1130        1140        1150
ACG GGC GGC AAG GTC AAG GCG CCC AAG CAC CGG GTC AAG TCT CCC GGG
THR GLY GLY LYS VAL LYS ALA PRO LYS HIS ARG VAL LYS SER PRO GLY
235             240             245             250

1160        1170        1180        1190
CGC GAC CAG CGC GTC GGC AGC AGC CGC ACG TCG AGC GTC TTC TTC CTG
ARG ASP GLN ARG VAL GLY SER SER ARG THR SER SER VAL PHE PHE LEU
                255             260             265

1200        1210        1220        1230        1240
CGG CCG AAG CCC GAC TTC AGC TTC AAC GTG CAG CAG TCG AGG GAG TGG
```

-continued

DNA Sequence of the DACS/DAOCS Gene
(the expandase/hydroxylase gene) of
Cephalosporium acremonium

```
ARG PRO LYS PRO ASP PHE SER PHE ASN VAL GLN GLN SER ARG GLU TRP
        270                 275                 280

1250            1260            1270            1280            1290
GGT TTC AAC GTC CGC ATC CCG TCG GAG CGC ACG ACG TTC AGG GAG TGG
GLY PHE ASN VAL ARG ILE PRO SER GLU ARG THR THR PHE ARG GLU TRP
        285                     290                     295

1300            1310            1320            1330            1340
CTT GGC GGG AAC TAT GTC AAC ATG CGG AGG GAT AAG CCG GCG GCA GCG
LEU GLY GLY ASN TYR VAL ASN MET ARG ARG ASP LYS PRO ALA ALA ALA
        300                     305                     310

1350            1360            1370            1380            1390
GAG GCG GCT GTC CCC GCG GCT GCC CCT GTC TCT ACC GCA GCT CCT ATA
GLU ALA ALA VAL PRO ALA ALA ALA PRO VAL SER THR ALA ALA PRO ILE
315                     320                     325                     330

1400            1410            1420            1430
GCC ACT TAG GGA ACC CGC CGA TCG AGT AAT AAA TCT ACG GGA GTT TAA
ALA THR 1440            1450            1460            1470        480
GAA GAA AAA TTG CCC TAT AAA TTG CTA AAT TTT TAA AAC ACA AAG CAT 1490            1500            1510
GAG TGT CAA GAG TTT CAA GTT TCA A-3'
``` wherein A is deoxyadenyl, G is deoxyguanyl, C is deoxycytidyl, T is thymidyl, ALA is an alanine residue, ARG is an arginine residue, ASN is an asparagine residue, ASP is an aspartic acid residue, CYS is a cysteine residue, GLN is a glutamine residue, GLU is a glutamic acid residue, GLY is a glycine residue, HIS is a histidine residue, ILE is an isoleucine residue, LEU is a leucine residue, LYS is a lysine residue, MET is a methionine residue, PHE is a phenylalanine residue, PRO is a proline residue, SER is a serine residue, THR is a threonine residue, TRP is a tryptophan residue, TYR is a tyrosine residue, and VAL is a valine residue.

The DNA sequence shown above is ~63% in G and C content and encodes a polypeptide with a calculated molecular weight of 36,462 daltons and an observed molecular weight of about 40,000 daltons. Those skilled in the art will recognize that the DNA sequence depicted above is an important part of the present invention. The above sequence can be conventionally synthesized by the modified phosphotriester method using fully protected deoxyribonucleotide building blocks. Such synthetic methods are well known in the art and can be carried out in substantial accordance with the procedure of Itakura et al., 1977, Science 198:1056 and Crea et al., 1978, Proc. Nat. Acad. Sci. USA 75:5765. In addition, an especially preferred method is disclosed in Hsiung et al., 1983, Nucleic Acid Research 11:3227 and Narang et al., 1980, Methods in Enzymology 68:90. In addition to the manual procedures referenced above, the DNA sequence can be synthesized using automated DNA synthesizers, such as the Systec 1450A or ABS (Applied Biosystems, 850 Lincoln Centre Drive, Foster City, Calif. 94404) 380A DNA Synthesizers.

Due to the degenerate nature of the genetic code, which results from there being more than one codon for most of the amino acid residues and translation stop signal, the amino acid residue sequence of DACS/DAOCS enzyme depicted above can be encoded by a multitude of different DNA sequences. Because these alternate DNA sequences would encode the same amino acid residue sequence of the present invention, the present invention further comprises these alternate sequences.

Due to the diverse number of Cephalosporium species and even of different strains within the same species there are genetic variants of the DACS/DAOCS-encoding DNA of the present invention. These genetic variants share substantial DNA and amino acid residue sequence homology with the compounds of the present invention and encode proteins with similar, if not for all practical purposes identical, activity, but differ somewhat from the actual compounds of the present invention. These genetic variants are also equivalent to the compounds of the present invention.

The DACS/DAOCS activity-encoding DNA compounds of the present invention were isolated from a strain of *Cephalosporium acremonium* commonly known as the Brotzu strain that is available from the American Type Culture Collection, Rockville, Md., under the accession number ATCC 11550. A genomic library of the total genomic DNA of the Brotzu strain was constructed in the bifunctional cosmid vector pKC462A (available in *E. coli* K12 SF8 under NRRL B-15973) and examined for the presence of sequences homologous to a set of 32 different deoxyribooligonucleotides. This set of 32 different deoxyribooligonucleotides was constructed in accordance with information obtained from a partial amino acid sequence of the *C. acremonium* DACS/DAOCS enzyme and knowledge of the genetic code. A variety of vectors were identified that were homologous to one or more of the 32 different deoxyribooligonucleotides. DNA sequencing revealed which vectors encoded the *C. acremonium* DACS/DAOCS enzyme.

After the vectors that encoded the DACS/DAOCS enzyme were identified, an ~7.0 kb BamHI restriction fragment comprising the DACS/DAOCS gene was isolated and inserted into commercially available plasmid pUC8 to yield plasmid pIT503, which was then transformed into *E. coli* K12 JA221 host cells. The *E. coli* K12 JA221/pIT503 transformants have been deposited and made part of the stock culture collection of the Northern Regional Research Laboratories (NRRL), Peoria, Ill. 61604, under the accession number NRRL B-18170. A restriction site and function map of plasmid pIT503 is presented in FIG. 1 of the accompanying drawings.

Plasmid pIT503 serves as useful starting material for the construction of other expression vectors of the invention. These vectors are especially useful in a method for producing DACS/DAOCS activity in a recombinant host cell, said method comprising:

(1) transforming said host cell with a recombinant DNA expression vector that comprises: (a) a promoter and translational activating sequence; and (b) a DNA sequence that encodes DACS/DAOCS activity and is positioned for expression from said promoter; and (2) culturing said host cell transformed in step (1) under conditions that allow for expression of said DACS/DAOCS activity.

Plasmid pIT503 can be isolated from *E. coli* K12 JA221 by the procedure described in Example 1 and used to construct the *E. coli* DACS/DAOCS expression vectors of the invention. Plasmid pIT503 was used as starting material to construct plasmid pIT507, which drives high-level expression of DACS/DAOCS activity in *E. coli*. The construction protocol for plasmid pIT507 is presented in Example 2 (see 2K) and involves ligating the ~2.2 kb SstI-BamHI, DACS/DAOCS-encoding restriction fragment of plasmid pIT503 to the ~5.8 kb NdeI-BamHI fragment of pCZR336 and an ~60 bp SstI-NdeI synthetic fragment.

Figure 11:
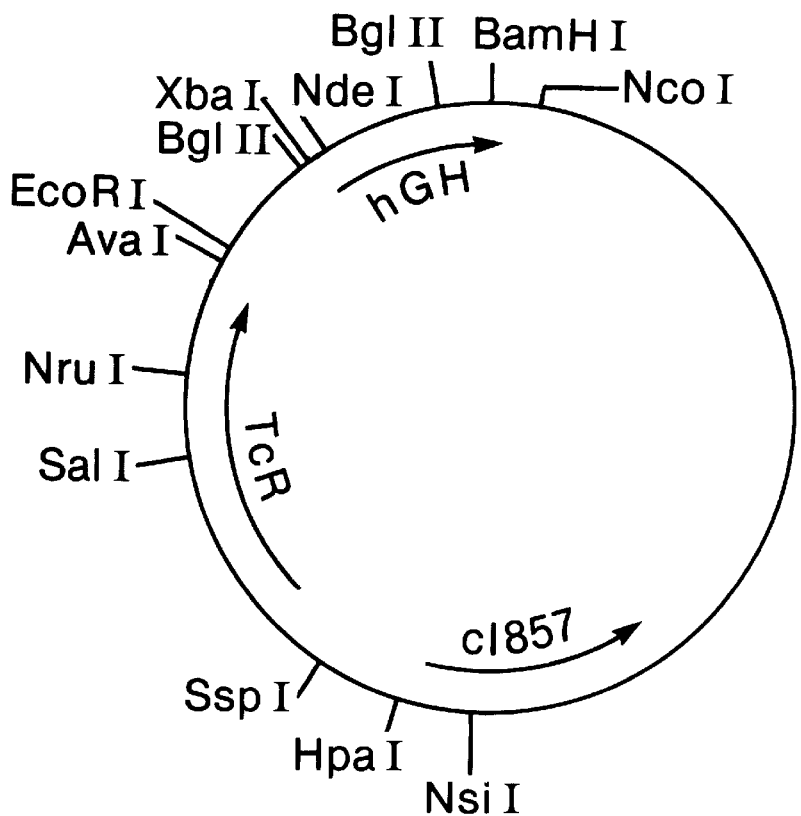
FIG. 11. Restriction site and function map of plasmid pCZR336.

Plasmid pCZR336 comprises a λpL-derived promoter, translational activating sequence, the λpL operator encoded by the cI857 repressor gene, a first "cistron" encoding a small peptide that precedes the gene of interest, and a DNA sequence encoding an hGH derivative. At low temperatures of about 30° C., the cI857 protein encoded on plasmids pCZR336 and pIT507 is active and able to repress activity of the λpL promoter, but when the temperature is raised to about 42° C., the cI857 protein is inactivated, and the λpL promoter drives transcription of large amounts of mRNA encoding hGH (pCZR336) or DACS/DAOCS (pIT507). A restriction site and function map of plasmid pCZR336 is presented in FIG. 11 of the accompanying drawings.

Plasmid pIT507 comprises the same first cistron, cI857 gene, λpL promoter, and translational activating sequence as does plasmid pCZR336 but contains the coding sequence of the DACS/DAOCS gene from plasmid pIT503 instead of the hGH coding sequence. The ~2.2 kb SstI-BamHI restriction fragment of plasmid pIT503 comprises the majority of the coding sequence for DACS/DAOCS, and the remainder of the coding sequence is contained on an ~60 bp NdeI-SstI synthetic fragment, with slight modifications from the wild-type DNA sequence to facilitate future work. The NdeI restriction enzyme recognition sequence, which is

comprises the

Figure 12:
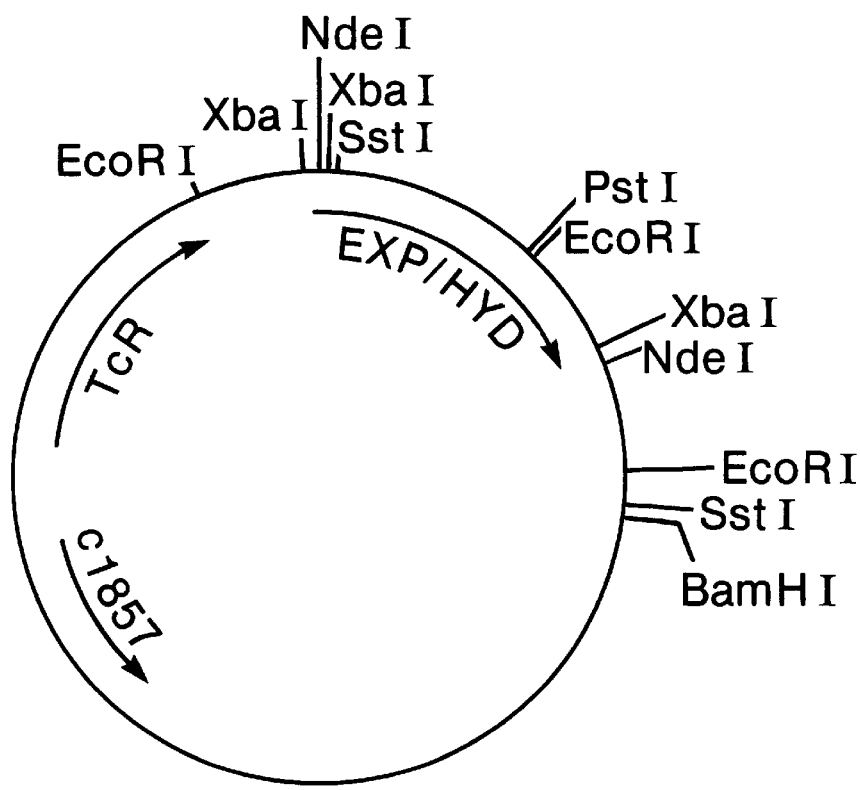
FIG. 12. Restriction site and function map of plasmid pIT507.

that encodes the amino-terminal methionyl residue of DACS/DAOCS. Plasmid pIT507 was constructed so that the λpL promoter and the translational activating sequences are positioned to drive expression of the DACS/DAOCS-encoding DNA. A restriction site and function map of plasmid pIT507 is presented in FIG. 12 of the accompanying drawings. Example 2 describes the construction of plasmid pIT507 in more detail.

At temperatures of about 42° C., *E. coli* K12 JM109/pIT507 express DACS/DAOCS activity at high levels, approaching ~15% of the total cell protein. Crude cell extracts from these *E. coli* K12 JM109/pIT507 transformants are able to catalyze the conversion of penicillin N into DAOC and DAC, whereas cell extracts from non-transformed *E. coli* K12 JM109 cells cannot catalyze this conversion. The method of assay and results of the assay for the conversion reaction are presented in Example 3.

Many *E. coli* K12 strains contain an endogenous penicillinase activity, probably encoded by the ampC locus. For this reason it is desirable to effect a partial purification of the DAOCS/DACS polypeptide so that optimal DAOCS/DACS activity is observed. For these purposes, purification of the enzyme through DEAE-Trisacryl is sufficient to separate the endogenous *E. coli* penicillinase activity from the desired DAOCS/DACS activity. An example of this type of partial purification is summarized below in Example 3. An alternative to the use of partial purification to overcome the deleterious effects of the penicillinase is to use a strain defective in the production of this activity. One such strain, *E. coli* K12 A85892, is available from the Northern Regional Research Center under the accession number NRRL B-18096.

Plasmids pIT507 and pIT511 (described below) provide an efficient means of producing large amounts of DACS/DAOCS in *E. coli*. Because *E. coli*/pIT507 express DACS/DAOCS at levels approaching 15% of total cell protein, and because culturing *E. coli* is less complex than culturing organisms that naturally produce DAOCS and/or DACS, *E. coli*/pIT507 transformants can be used to produce recombinant DACS/DAOCS more efficiently and economically than non-recombinant or "natural" DACS/DAOCS producers.

DAOCS can be used to produce DAOC from penicillin N in a cell-free system as described in Example 3. DAOC is not only a useful antibiotic, but also can be used as the starting material for the production of such important antibiotics as cephalexin and other cephalosporins (see U.S. Pat. No. 4,307,192). Perhaps the most important use of DACS/DAOCS is the use of the enzyme to transform penicillins other than penicillin N into novel cephalosporin derivatives.

Cell-free extracts of penicillin and cephalosporin-producing organisms can be used to synthesize unnatural (not produced in nature) β-lactams. The *E. coli* expression vectors of the present invention provide an inexpensive and efficient method of obtaining DACS/DAOCS, which can be used in vitro to transform penicillins that do not naturally occur in nature to form novel antibiotics or antibiotic core structures.

Plasmid pIT507 is especially preferred for driving expression of DACS/DAOCS in *E. coli* not only because of the high expression levels achieved when using the plasmid but also because of the selectable marker present on the plasmid.

Many recombinant DNA vectors encode a β-lactamase, so that cells containing the vector can grow in the presence of certain β-lactam antibiotics, such as ampicillin. However, if one desires to use a cell-free extract containing DACS/DAOCS for purposes of constructing β-lactams, one does not want the extract to contain β-lactamase activity. Thus, plasmid pIT507 does not encode a β-lactamase for a selectable marker but rather employs a tetracycline resistance-conferring gene, which encodes a protein that does not react with β-lactams.

The DACS/DAOCS expression vectors of the present invention are not limited to a particular selectable marker. Those skilled in the art recognize that many selectable markers are suitable for use on DACS/DAOCS expression vectors. Such selectable markers include genes that confer kanamycin resistance, genes that confer chloramphenicol resistance, or other antibiotic resistance-conferring genes.

The search for unnatural penicillins that will serve as substrates for DACS/DAOCS can be complemented by a search for mutant DACS/DAOCS enzymes that will accept penicillins other than penicillin N as substrate. The present invention provides the starting material for such a search for a mutant DACS/DAOCS and comprises DNA compounds derived through mutagenesis of a DACS/DAOCS coding sequence. E. coli is the best host for mutational cloning experiments, and the E. coli expression vectors of the present invention can be readily mutated by procedures well known in the art, such as, for example, treatment with radiation (X-ray or UV) or chemical mutagens (such as ethylmethanesulfonate, nitrosoguanidine, or methyl methanesulfonate) or site-specific mutagenesis, to obtain mutant enzymes that recognize unnatural penicillins as substrate and catalyze the conversion of those unusual and/or unnatural penicillins to unnatural cephalosporins.

Example 4 describes the construction protocol for another expression vector, designated pIT511, identical to plasmid pIT507 except that all but about 120 bp of 3' noncoding (downstream of the translation termination signal) information has been eliminated from the expression vector. This vector is a superior starting material for mutagenesis work because the DACS/DAOCS coding region is a larger percentage of the total vector.

As those skilled in the art will recognize, the present invention allows one to change the codons for the DACS/DAOCS gene at will. Given the DNA sequence for the DACS/DAOCS gene, only routine procedures are required to generate mutant DACS/DAOCS enzymes that vary from the natural DACS/DAOCS enzyme at any number of amino-acid residue positions. Such mutant enzymes would be encoded by mutant DACS/DAOCS coding sequences, including sequences in which amino-acid codons have been deleted from or inserted into the natural DACS/DAOCS coding sequence. Such mutant DACS/DAOCS enzymes are within the scope of the present invention, because even if one cannot absolutely predict whether a given mutation will destroy activity of the encoded DACS/DAOCS, one need merely express the mutant sequence, as exemplified herein, to ascertain the effect on DACS/DAOCS activity.

Examples of production of mutant forms of DACS/DAOCS are given in Examples 5 and 6. Example 5 describes a deletion of the coding information for 10 amino acids from near the amino terminus of the DACS/DAOCS by deletion of the corresponding 30 bp in the coding sequence and the expression of the mutant polypeptide in E. coli. This mutant DACS/DAOCS is expressed from plasmid pIT512, as exemplified by E. coli K12 JM109/pIT512 transformants.

Besides alteration of the amount of genetic information (thereby causing insertion or deletion of amino acids in the resulting protein) the specific DNA sequence can be altered, thereby altering the encoded amino acid sequence. One way of accomplishing this site-directed mutagenesis is described in Example 6. The DACS/DAOCS protein contains a cysteine residue at position 100; Example 6 describes a procedure for changing this residue to a serine in the DACS/DAOCS coding region of the expression vector plasmid pIT513. This general method can be used to change any residue to any of the other 19 naturally-encoded amino acids. In vitro splicing of mutant genes created by such a method allows production of proteins with combinations of mutations.

The present invention is not limited to the particular vectors exemplified herein. Instead, the present invention comprises DNA compounds that encode any DAOCS and/or DACS activity. The DNA compounds of the present invention can be used to construct expression vectors that drive expression of DACS/DAOCS activity in any host cell in which the expression vector replicates or integrates and in which the promoter and translational activating sequence used to express the DACS/DAOCS activity functions.

Therefore, although the E. coli expression vectors exemplified herein utilize a two cistron construction whose transcription is driven by λpL in E. coli, the present invention comprises any E. coli expression plasmid or vector that drives expression of DACS/DAOCS in E. coli. Thus, the present invention comprises expression vectors that drive expression of DACS/DAOCS and utilize a replicon functional in E. coli, such as, for example, a replicon from such plasmids as pBR322, pACYC184, F, ColV-K94, R1, R6-5, or R100. Nor is the present invention solely limited to plasmid vectors, for the present invention also comprises expression vectors that express DACS/DAOCS activity and utilize integration or viral replication to provide for replication and maintenance in the host cell.

The present invention is not limited to a particular promoter and translational activating sequence to drive expression of the DACS/DAOCS synthetase activity-encoding DNA. The present invention comprises the use of any promoter and translational activating sequence that functions in E. coli and is used to express DACS/DAOCS in E. coli. Many promoter and translational activating sequences functional in E. coli are known and are suitable for driving expression of DACS/DAOCS activity in E. coli. Such transcriptional and translational activating sequences include, but are not limited to, the lpp, lac, trp, tac, λpL, and λpR promoter and translational activating sequences.

In addition to the various E. coli transcriptional and translational activating sequences exemplified above, transcriptional and translational activating sequences from other organisms can be ligated to the present DAOC synthetase-encoding DNA compounds to form expression vectors that drive expression of DAOC synthetase activity in host cells in which the activating sequence functions. Although E. coli is the host best suited for DACS/DAOCS production and subsequent purification for in vitro use, vectors that drive expression of DAOC synthetase activity in host cells other than E. coli are also useful, especially for purposes of increasing the cephalosporin antibiotic-producing ability and efficiency of a given organism.

A variety of organisms produce β-lactam antibiotics. The following Table presents a non-comprehensive list of β-lactam antibiotic-producing organisms.

TABLE I

β-Lactam Antibiotic-Producing Organisms

| Organism | Antibiotic |
|---|---|
| Agrobacterium | various β-lactams |
| Arachnomyces minimus | penicillins and cephalosporins |
| Anixiopsis peruviana | penicillins and cephalosporins |
| Cephalosporium | |
| acremonium purpurascens polyaleurum chrysogenum curtipes | penicillins and cephalosporins |
| Chromobacterium | various β-lactams |
| Emericellopsis | |
| terricola minima synnematicola glabra mirabilis salmosynnemata | penicillins and cephalosporins |
| Flavobacterium | various β-lactams |
| Gluconobacter | various β-lactams |
| Nocardia | |
| lactamadurans | cephamycin C |
| uniformis | nocardicin |
| Paecilomyces | |
| carneus persicinus | penicillins and cephalosporins |
| Penicillium chrysogenum | various penicillins and other β-lactams |
| Serratia | various β-lactams |
| Spiroidium fuscum | penicillins and cephalosporins |
| Streptomyces | |
| antibioticus | clavulanic acid |
| argenteolus | asparenomycin A, MM 4550, and MM 13902 |
| cattleya | thienamycin |
| chartreusis | SF 1623 and cephamycin A and B |
| cinnamonensis | cephamycin A and B |
| clavuligerus | PA-32413-I, cephamycin C, A16886A, penicillins, cephalosporins, clavulanic acid, and other clavams |
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B and carpetimycin A and B |
| halstedi | cephamycin A and B |
| heteromorphus | C2081X and cephamycin A and B |
| hygroscopicus | deacetoxy-cephalosporin C |
| lipmanii | cephamycin, penicillin N, 7-methoxycephalosporin C, A16884, MM4550, MM13902 |
| olivaceus | epithienamycin F, MM 4550, and MM 13902 |
| panayensis | C2081X and cephamycin A and B |
| pluracidomyceticus | pluracidomycin A |
| rochei | cephamycin A and B |
| sioyaensis | MM 4550 and MM 13902 |
| sp. OA-6129 | OA-6129A |
| sp. KC-6643 | carpetimycin A |
| tokunomensis | asparenomycin A |
| viridochromogenes | cephamycin A and B |
| wadayamensis | WS-3442-D |

Many of the foregoing β-lactam antibiotic-producing organisms are used in the pharmaceutical industry for purposes of antibiotic production. The antibiotic-producing ability of these organisms can be increased and made more efficient by increasing the intracellular concentration of the antibiotic biosynthetic enzymes during the fermentation. The DACS/DAOCS activity-encoding DNA compounds of the present invention can be used to construct expression vectors that, when transformed into the appropriate host cell, increase the intracellular concentration of DACS/DAOCS activity of the transformed host cell and thereby increase the antibiotic-producing ability and efficiency of that cell, provided that the host cell produces a β-lactam antibiotic.

A vector that will increase the intracellular concentration of DACS/DAOCS activity of a given host cell into which the vector is transformed requires the following elements: 1) a DACS/DAOCS activity-encoding DNA compound of the present invention; and 2) a promoter and translational activating sequence that not only functions in the host cell to be transformed, but also is positioned in the correct orientation and position to drive expression of the DACS/DAOCS activity-encoding DNA. Of course, stable transformants can only be obtained if the vector replicates, either as an extrachromosomal element or integrated in the genomic DNA, in the host cell. The above-described vector could also comprise an antibiotic resistance-conferring gene or some other element that provides a means of selecting for host cells which contain the vector, but such selectable elements may neither be necessary nor desired when the vector integrates into the chromosomal DNA of the host cell.

The present invention also provides illustrative expression vectors for Penicillium and Cephalosporium. For convenience, key features of the intermediate and expression plasmids described below and in the Examples are listed in Table II below. The relationships among the plasmids are also shown schematically in FIG. 34 of the attached drawings.

TABLE II

| Plasmid | Figure | Example | Selections | Gene of Interest | Source of Promoter for Gene of Interest |
|---|---|---|---|---|---|
| pIT503 | 1 | 1 | TcR | DACS/DAOCS | DACS/DAOCS |
| pIT507 | 12 | 2K | TcR | DACS/DAOCS | λpL |
| pIT511 | 15 | 4 | TcR | DACS/DAOCS | λpL |
| p3SR2 | 18 | 8 | ApR, amdS | — | — |
| pMLC12 | 19 | 7,8 | CAT | — | — |
| pPS34 | 20 | 7 | ApR, HmR(cIPSp) | cIPS | cIPS |
| pPS51 | 21 | 8 | CAT, amdS | — | — |
| pPS52 | 22 | 9 | CAT, amdS | DACS/DAOCS | DACS/DAOCS |
| pPS53 | 23 | 10 | CAT | — | — |
| pPS54 | 24 | 11 | CAT, amdS | pIPS | pIPS |
| pPS55 | 25 | 7 | CAT, HmR(cIPSp) | — | — |
| pPS56 | 26 | 7 | CAT, HmR(cIPSp) | DACS/DAOCS | DACS/DAOCS |
| pPS57 | 27 | 12 | CAT, HmR(pIPSp) | — | — |
| pPS58 | 28 | 14 | TcR | DACS/DAOCS | pIPS |
| pPS59 | 29 | 15 | TcR | DACS/DAOCS | pIPS |
| pPS60 | 30 | 13 | TcR | DACS/DAOCS | pIPS* |
| pPS61 | 31 | 16 | CAT, amdS | DACS/DAOCS | pIPS |
| pPS62 | 32 | 17 | CAT, HmR(pIPSp) | DACS/DAOCS | pIPS |

*The Penicillium IPS promoter is separated by extraneous DNA from the DAOCS protein coding region in this construction.
TcR = tetracycline resistance-conferring gene
ApR = ampicillin resistance-conferring gene
CAT = chloramphenicol acetyltransferase
amdS = acetamidase gene
HmR(cIPSp) = hygromycin B phosphotransferase coding sequence fused with the *Cephalosporium acremonium* IPS gene promoter
HmR(pIPSp) = hygromycin B phosphotransferase coding sequence fused to *P. chrysogenum* IPS gene promoter.

Figure 19:
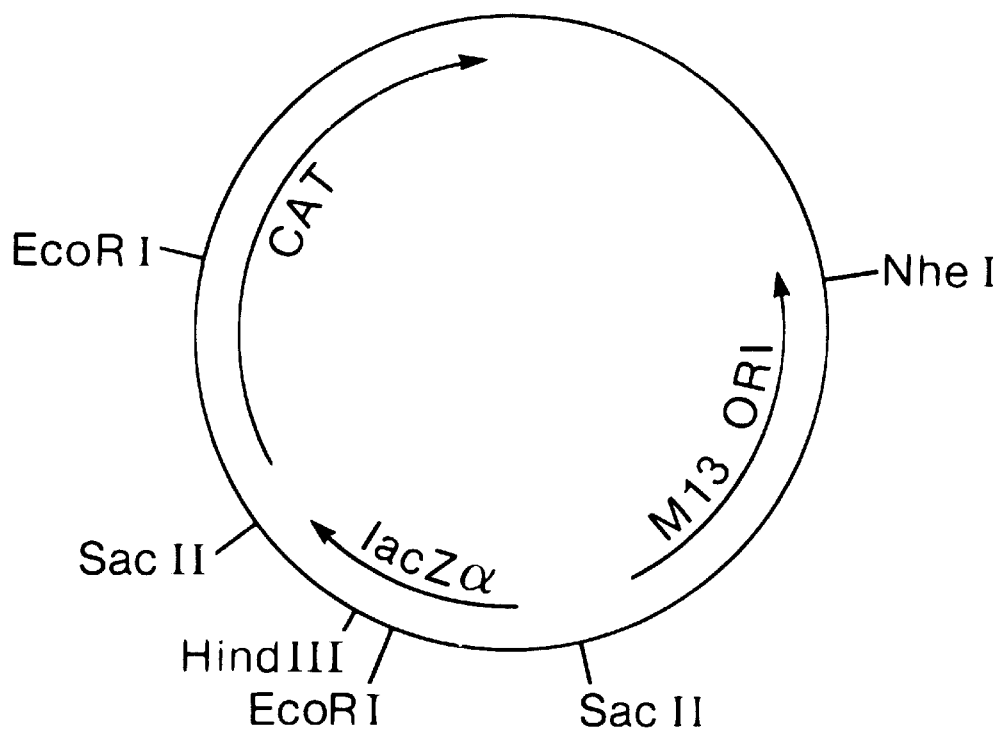
FIG. 19. Restriction site and function map of plasmid pMLC12.
Figure 20:
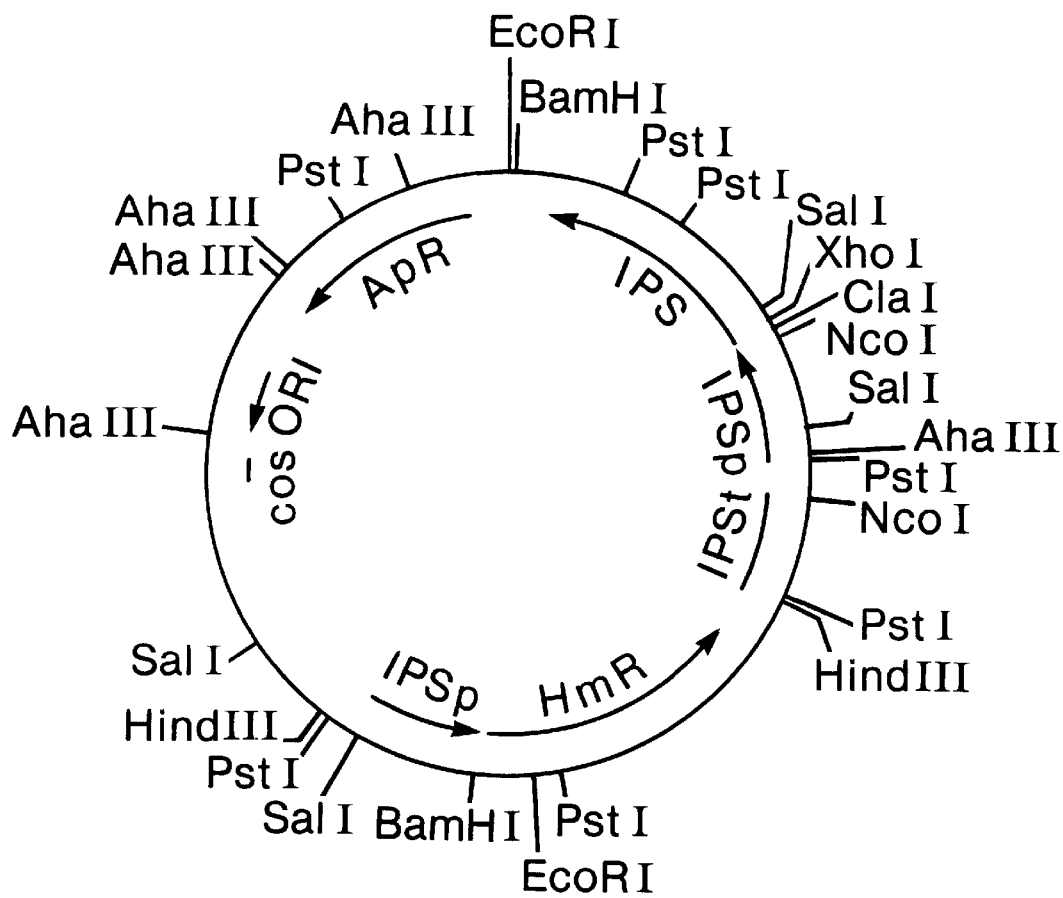
FIG. 20. Restriction site and function map of plasmid pPS34.
Figure 25:
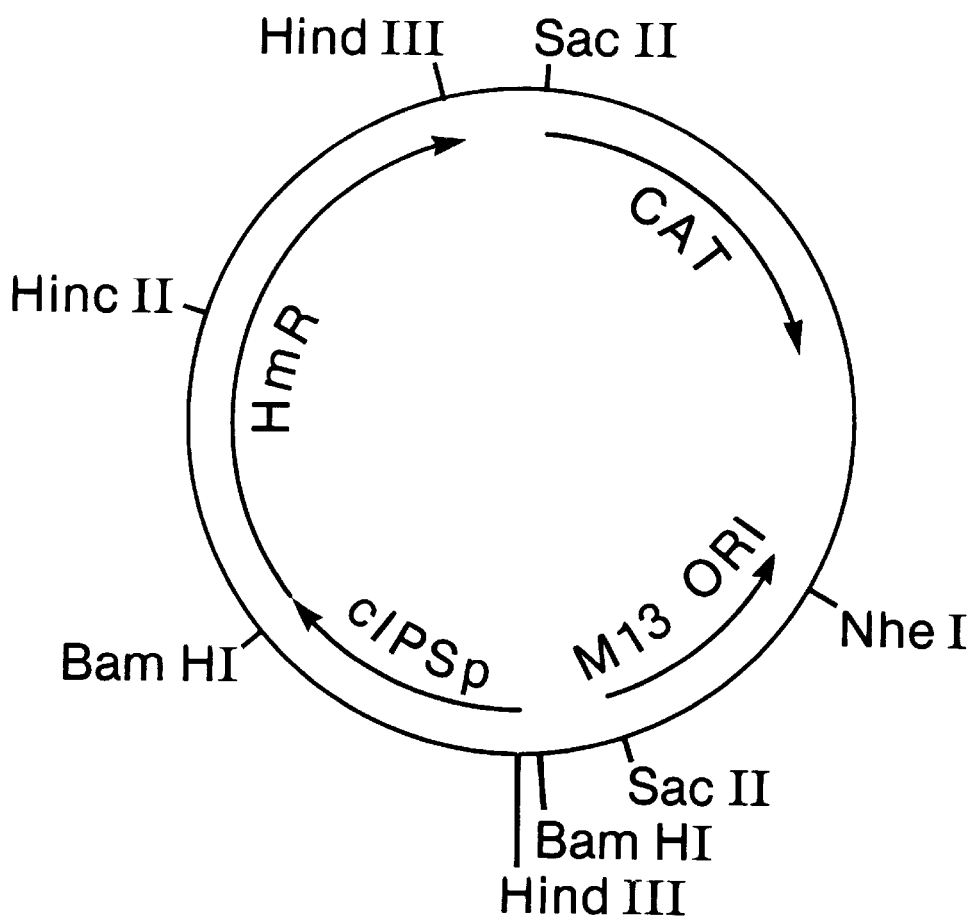
FIG. 25. Restriction site and function map of plasmid pPS55.
Figure 26:
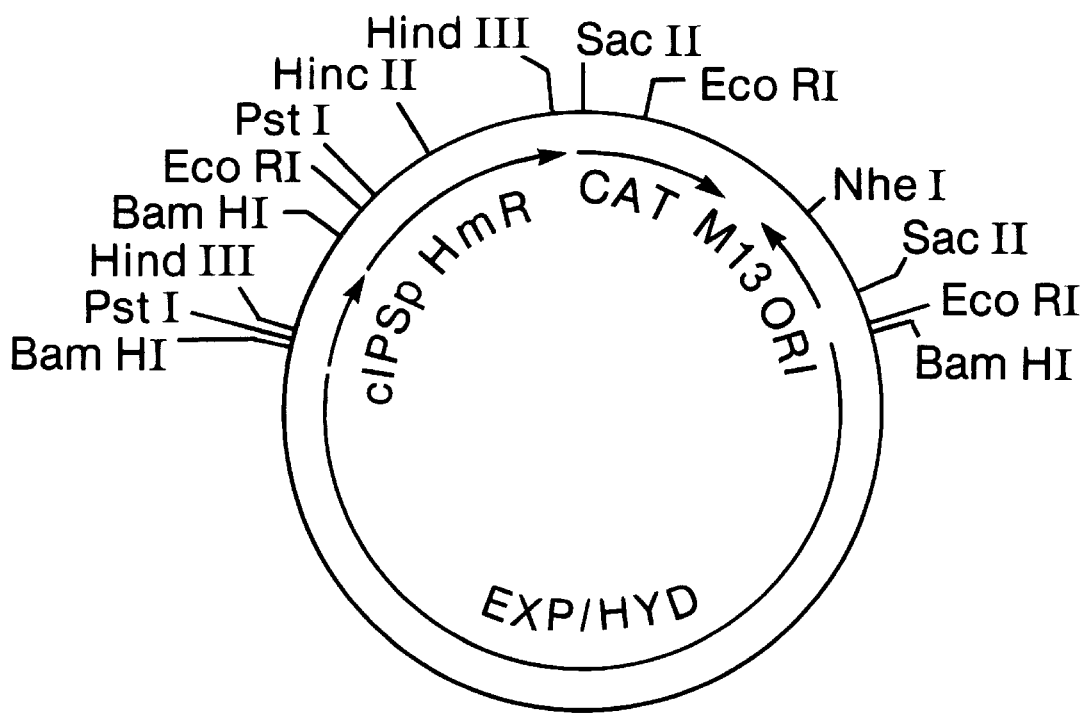
FIG. 26. Restriction site and function map of plasmid pPS56.

Plasmid pPS56 is a *Cephalosporium* expression vector of the invention. Plasmid pPS55 (FIG. 25) is an intermediate in the construction of plasmid pPS56 (FIG. 26). Plasmid pPS55 is constructed from the HindIII backbone of plasmid pMLC12 (FIG. 19) and the ~2.3 kb HindIII fragment from plasmid pPS34 (FIG. 20) that contains the *C. acremonium* IPS promoter fused to the hygromycin B phosphotransferase coding sequence (see Example 7). The ~7 kb, DACS/DAOCS gene-containing, BamHI fragment from plasmid pIT503 (FIG. 1) is fused to partially BamHI-digested plasmid pPS55 to yield plasmid pPS56 as described in Example 7B.

The *Cephalosporium acremonium* promoter and translational activating sequence encoded on plasmid pIT503 is correctly positioned to drive expression of the DACS/DAOCS synthetase activity-encoding DNA, because in the construction of plasmid pIT503 no deletions or insertions affecting the promoter and translational activating sequence were introduced in the DNA flanking the 5' end of the coding strand of the DACS/DAOCS activity-encoding DNA. Plasmid pIT503 and derivatives that contain the intact DACS/DAOCS gene can therefore be used to increase the antibiotic-producing ability and efficiency of Cephalosporium and related host cells in which the *C. acremonium* promoter and translational activating sequence functions. Plasmid pPS56 is preferred for this purpose, but plasmids pIT503 and pPS52 can also be used. This increased antibiotic-producing ability and efficiency results from increased levels of DACS/DAOCS activity, which in turn results from the presence of additional, expressed copies of the DACS/DAOCS gene. Plasmid pPS56 also comprises a hygromycin resistance-conferring gene that functions in *C. acremonium* and allows for selection of *C. acremonium*/pPS56 transformants.

Once the *Cephalosporium acremonium*/pPS56 transformants are selected (Example 21), however, there is no need to maintain the pressure of selection, hygromycin B, in the growth medium. Selective pressure is not required, because the *C. acremonium*/pPS56 transformants are very stable. This stability is believed to result from the plasmid pPS56 transforming *C. acremonium* via chromosomal integration. The present invention, however, is not limited to plasmids that drive expression of DACS/DAOCS synthetase activity in *C. acremonium* and transform via chromosomal integration but also includes extrachromosomally replicating DACS/DAOCS expression vectors (see U.S. Pat. No. 4,492, 758).

Figure 23:
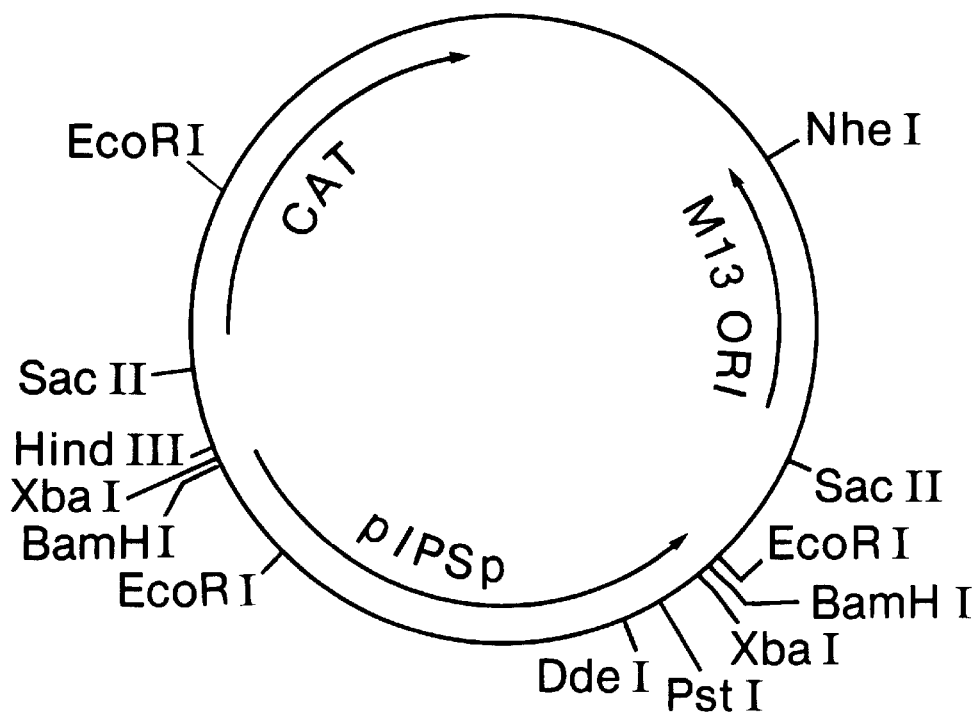
FIG. 23. Restriction site and function map of plasmid pPS53.
Figure 27:
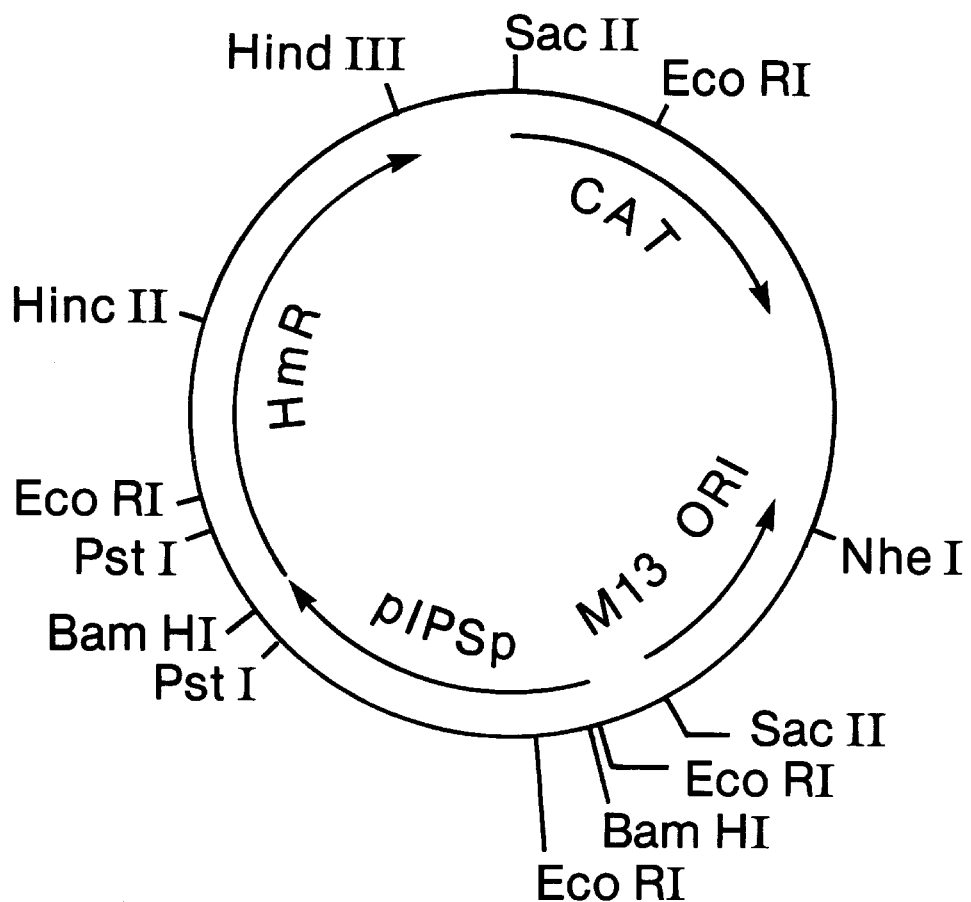
FIG. 27. Restriction site and function map of plasmid pPS57.
Figure 33:
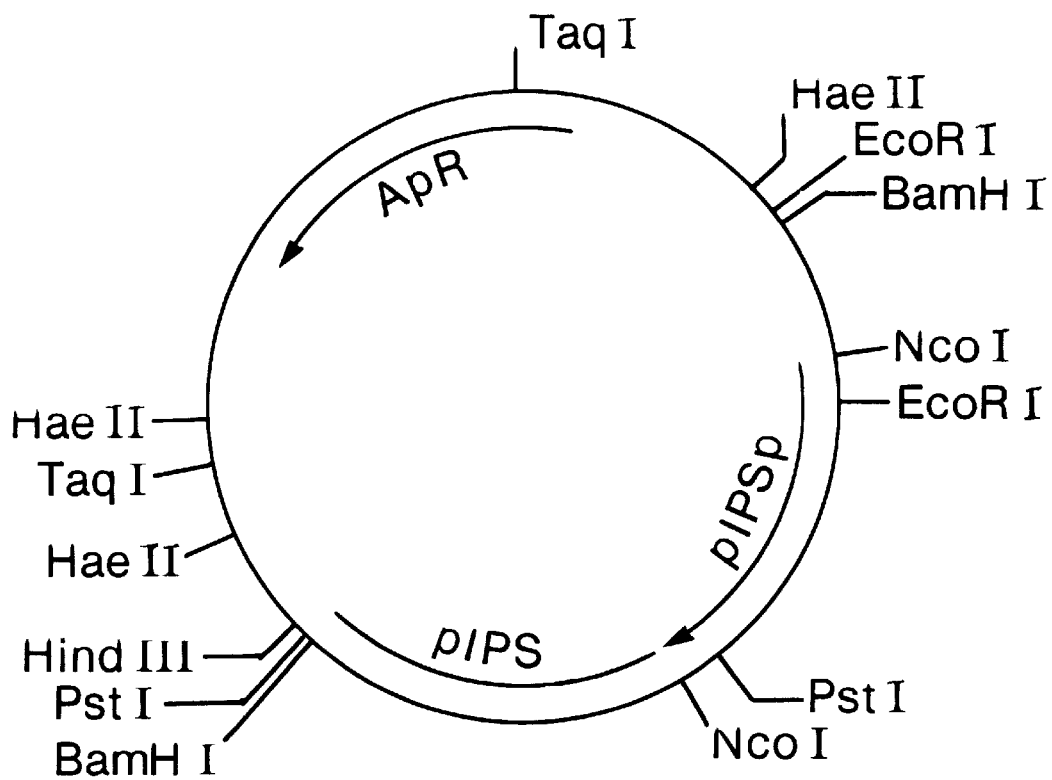
FIG. 33. Restriction site and function map of plasmid pLC1.
Figure 34:
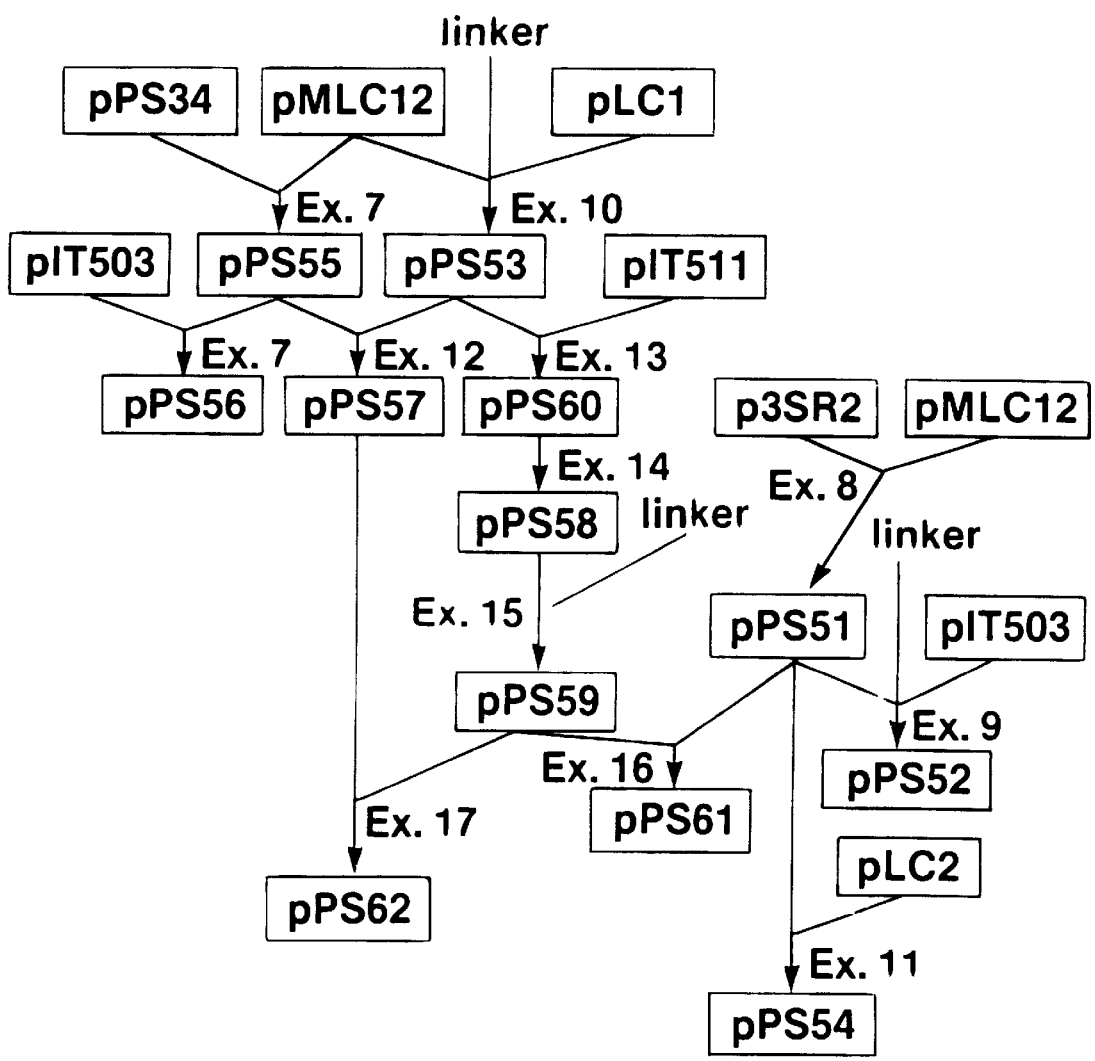
FIG. 34. Relationships and derivatizations of several of the plasmids of the present invention.

The promoter of the *Cephalosporium acremonium* DACS/DAOCS might also function in Penicillium (see the discussion of plasmid pPS52 below), but the optimal Penicillium expression vectors utilize a promoter derived from a Penicillium gene. The Penicillium IPS promoter from plasmid pLC1 (NRRL B-18181 and FIG. 33) is linked with the backbone of plasmid pMLC12 with the aid of a synthetic linker to produce plasmid pPS53 (FIG. 23), as described in Example 10. Plasmid pPS53 is an intermediate in the construction of several other cloning vectors and expression plasmids (FIG. 34). The ~1.0 kb, promoter-containing BamHI fragment of plasmid pPS53 is fused with the ~4.3 kb BamHI, HmR coding sequence-containing fragment of plasmid pPS55 to create plasmid pPS57 (FIG. 27), as described in Example 12.

Plasmid pPS57 is an intermediate in the construction of Penicillium expression vector pPS62 (FIG. 34). Plasmid pPS62 contains a selectable marker (HmR) and a hybrid DACS/DAOCS gene, with both the DACS/DAOCS and HmR coding sequences under the control of the promoter (2 copies) of the Penicillium IPS gene. The construction protocol for plasmid pPS62 is described in further detail below (see also Example 17).

Figure 28:
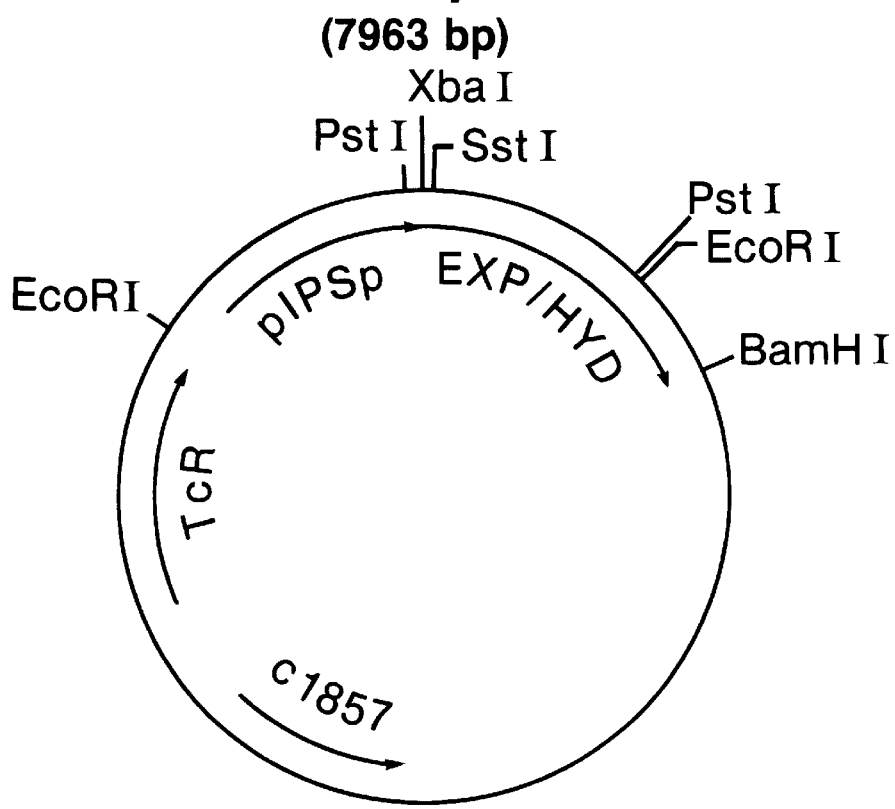
FIG. 28. Restriction site and function map of plasmid pPS58.
Figure 30:
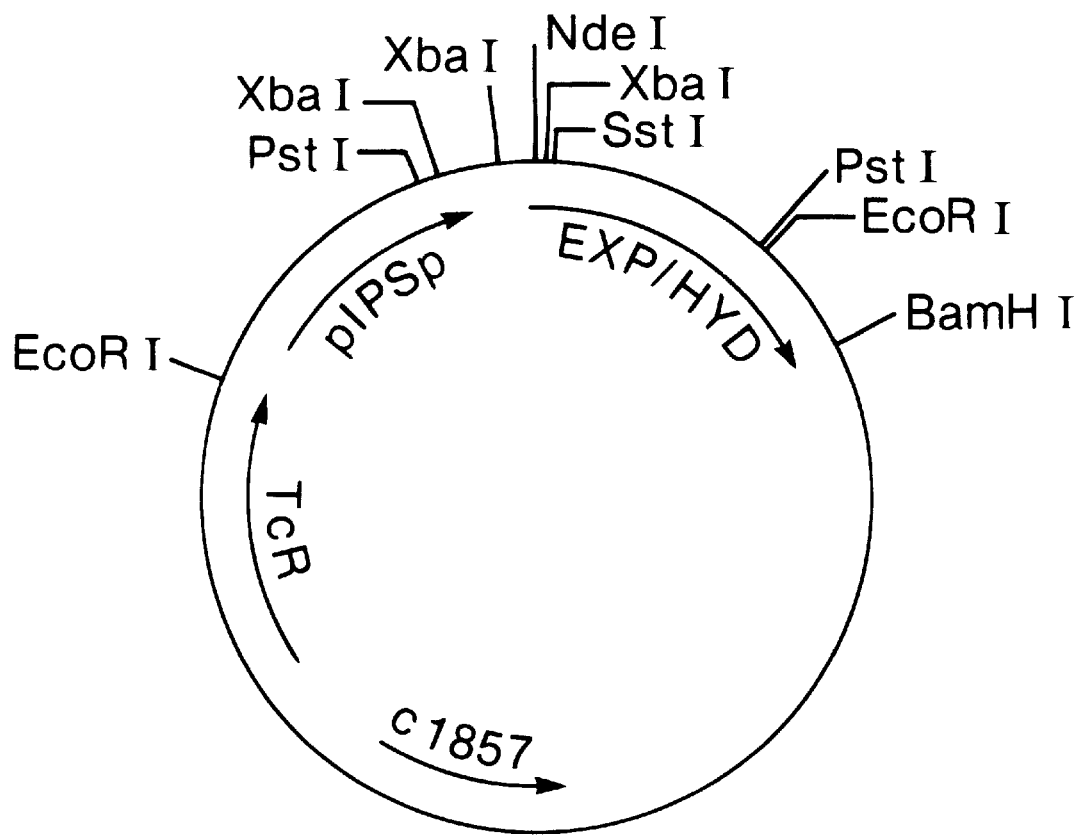
FIG. 30. Restriction site and function map of plasmid pPS60.

A Penicillium DACS/DAOCS expression vector without a selectable marker was constructed by inserting the ~1.0 kb BamHI, promoter-containing fragment of plasmid pPS53 into the BglII site of *E. coli* DACS/DAOCS expression vector pIT511 to yield plasmid pPS60 (FIG. 30), as described in Example 13. Plasmid pPS60 contains the Penicillium IPS promoter near, but not positioned optimally for expression of the DACS/DAOCS coding sequence. The proper alignment is achieved by first deleting two small XbaI restriction fragments from plasmid pPS60, creating plasmid pPS58 (FIG. 28), as described in Example 14. Then a synthetic linker is inserted into the XbaI site to create a more preferred alignment of the Penicillium IPS promoter and DACS/DAOCS coding sequence to yield plasmid pPS59, as described in Example 15. Plasmid pPS59 is useful for expressing DACS/DAOCS activity in cells in Penicillium and other cells in which the Penicillium IPS promoter functions.

Figure 32:
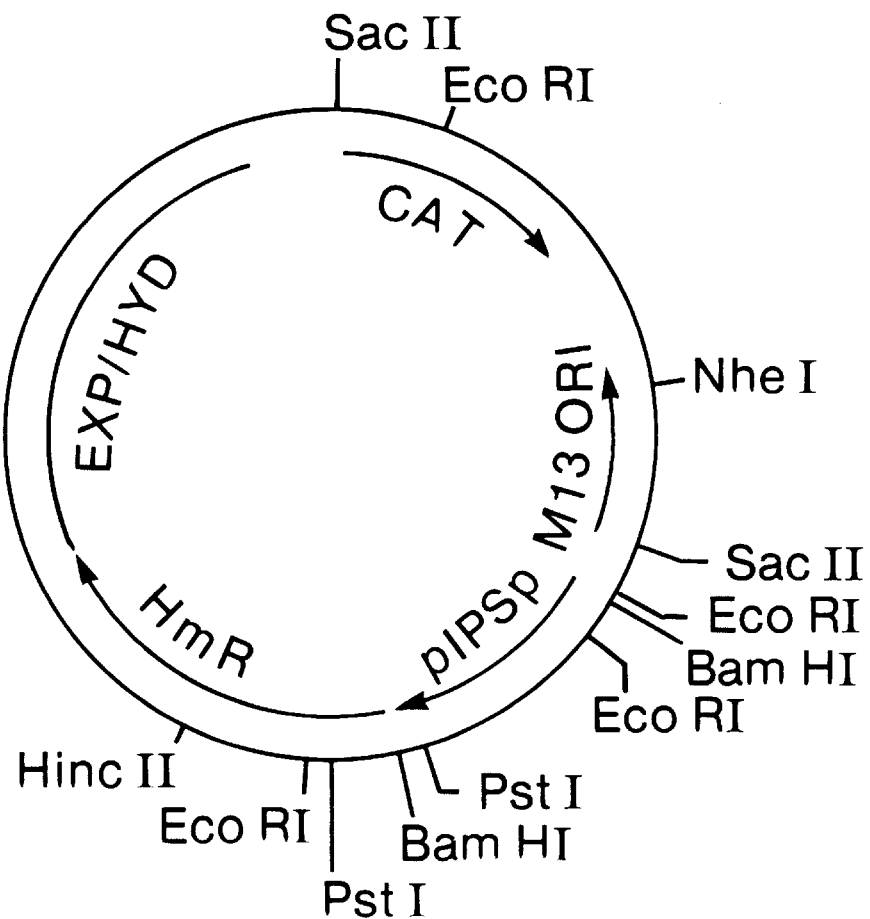
FIG. 32. Restriction site and function map of plasmid pPS62.

Plasmid pPS59 is also an intermediate for illustrative Penicillium DACS/DAOCS expression vectors pPS62 and pPS61. In both cases, an ~2.1 kb BamHI-NruI restriction fragment from plasmid pPS59, made blunt-ended with Klenow enzyme, is used as a source of the DACS/DAOCS coding sequence fused to the Penicillium IPS promoter. Plasmids pPS61 and pPS62 both contain selectable markers for Penicillium. Example 17 describes the fusion of the ~2.13 kb fragment of plasmid pPS59 with the HindIII-cleaved, Klenow-treated backbone of plasmid pPS57 to create plasmid pPS62 (FIG. 32). Plasmid pPS62 is a preferred vector for expressing DACS/DAOCS activity in Penicillium, especially *P. chrysogenum* host cells. Plasmid pPS62 is most useful in cells that can additionally be selected using the HmR gene on plasmid pPS62. Illustrative examples of this method for selecting Penicillium transformants are described in Example 18.

However, Penicillium strains are naturally somewhat resistant to hygromycin; optimal transformation conditions for using HmR as a selectable marker require the addition of hygromycin-sensitizing agents. A preferred method for selecting Penicillium transformants, which comprises an important aspect of the present invention, comprises (1) introducing a recombinant DNA vector comprising an acetamidase gene into a Penicillium host cell; and (2) culturing said host cell produced in step (1) in growth media that contains acetamide as the sole source of carbon or nitrogen. A preferred source of an illustrative acetamidase (amdS) gene, from *Aspergillus nidulans*, that can be used in the method is plasmid p3SR2 (NRRL B-18182).

Figure 21:
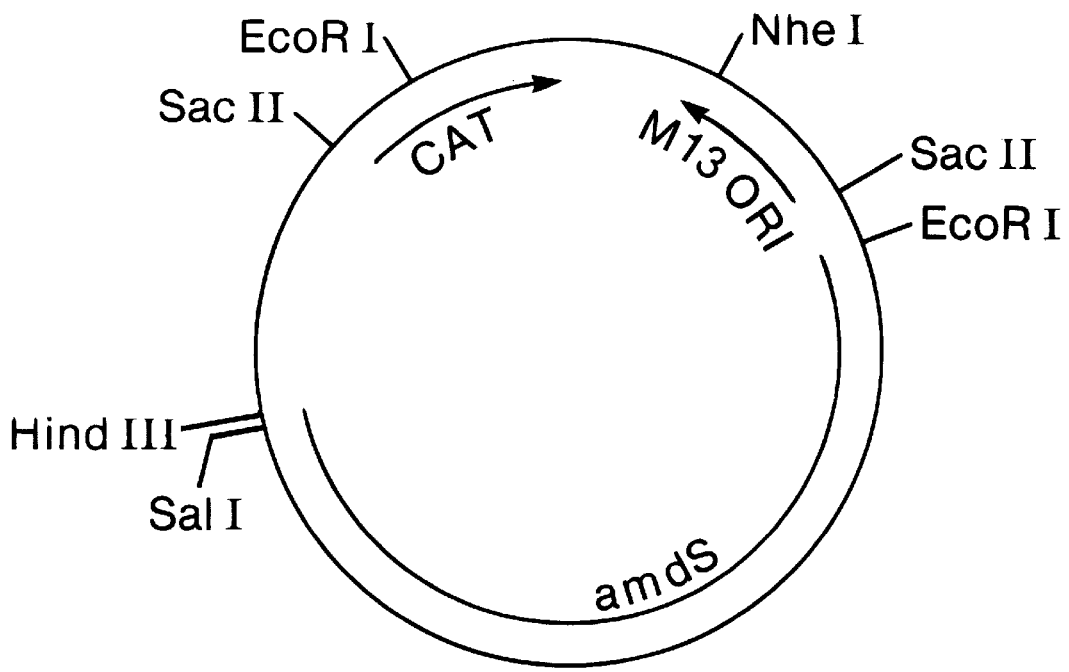
FIG. 21. Restriction site and function map of plasmid pPS51.
Figure 31:
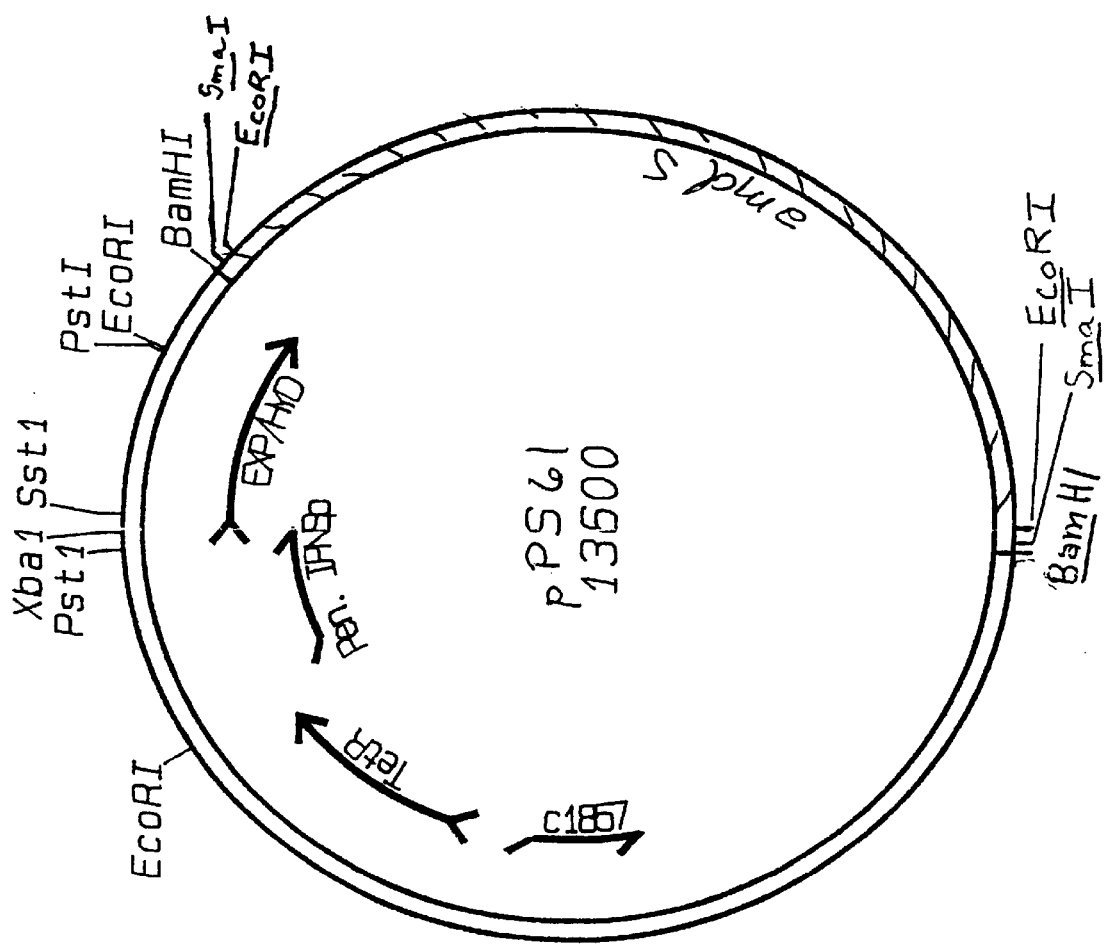
FIG. 31. Restriction site and function map of plasmid pPS61.

A useful intermediate vector of the invention, designated as pPS51 (FIG. 21), is composed of the amds gene from plasmid p3SR2 fused to the backbone of plasmid pMLC12, as described in Example 8. Plasmid pPS51 was linearized with HindIII, treated with Klenow, and ligated to the ~2.13 kb blunt-ended, hybrid DACS/DAOCS gene-containing fragment from plasmid pPS59 to create plasmid pPS61 (FIG. 31), as described in Example 16. Plasmid pPS61 is useful for expressing DACS/DAOCS activity in Penicillium, especially *P. chrysogenum*. Plasmid pPS61 is especially useful for transforming cells that can be subjected to growth on acetamide as a selection method. A description of this method for identifying Penicillium transformants using the amdS gene is described in Example 20.

Figure 22:
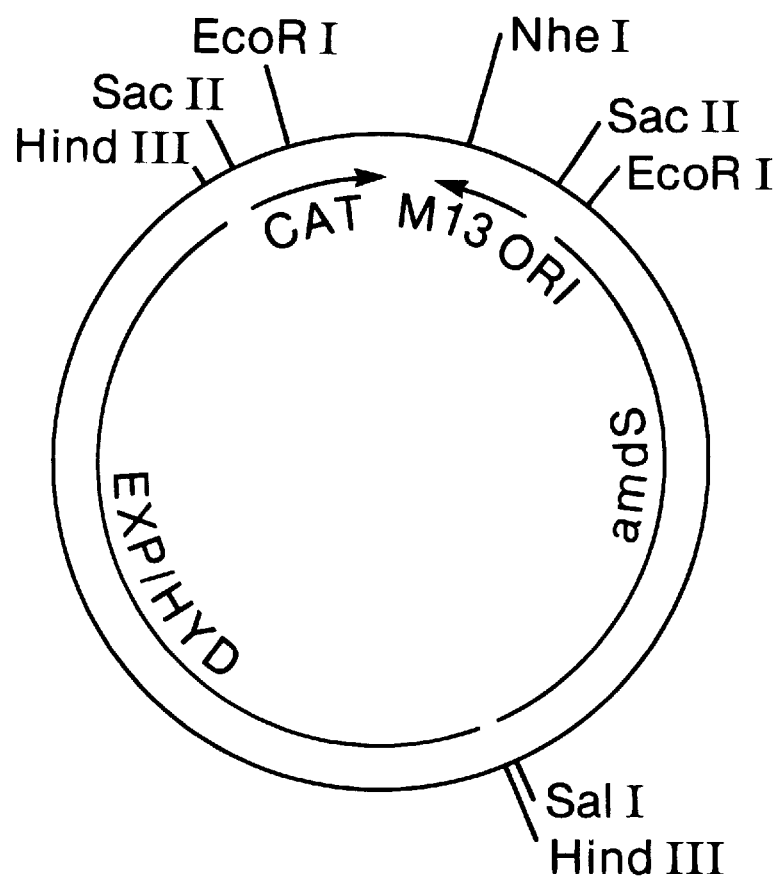
FIG. 22. Restriction site and function map of plasmid pPS52.

Plasmid pPS51 is used as a convenient source of the acetamidase gene in other constructions (FIG. 34). Example 9 describes the construction protocol for plasmid pPS52, which contains the DACS/DAOCS gene on an ~7 kb BamHI fragment (from plasmid pPS51) and a synthetic linker. Plasmid pPS52 (FIG. 22) is useful for expressing DACS/DAOCS activity, especially for cells in which both the Cephalosporium DACS/DAOCS promoter functions and the amdS can be used to select for transformants. Plasmid pPS52 can be used as an expression vector in either Cephalosporium or Penicillium.

Figure 24:
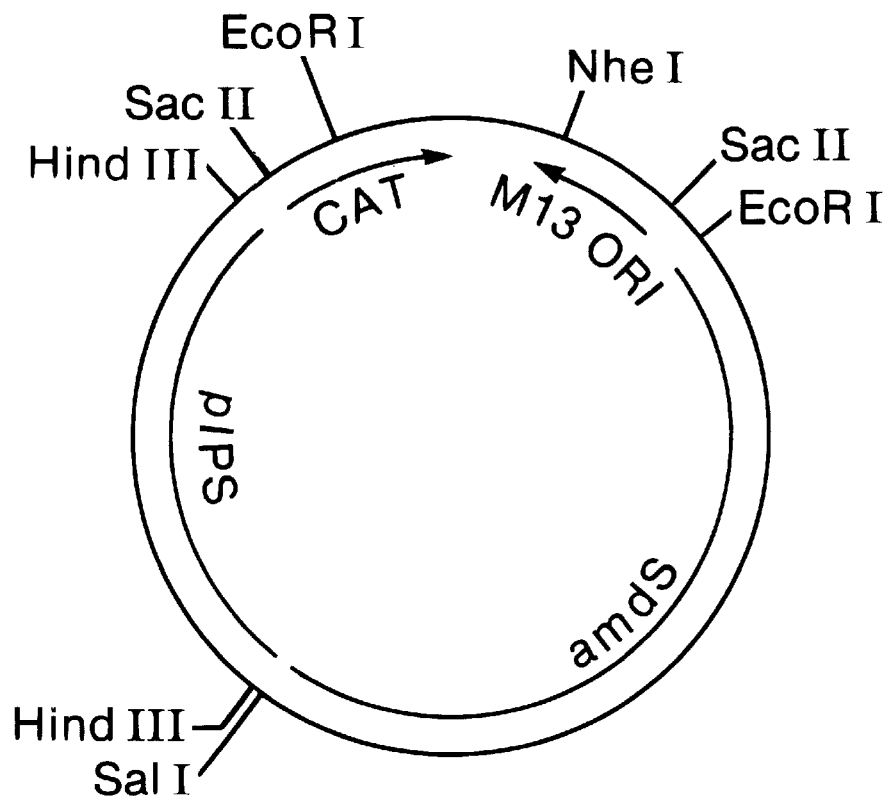
FIG. 24. Restriction site and function map of plasmid pPS54.

The amdS selectable marker can be incorporated into any expression vector. Illustrative vector pPS54 comprises the amdS gene from plasmid pPS51 and the Penicillium IPS gene. Plasmid pPS54 (FIG. 24) is a useful plasmid for expressing IPS activity, especially in cells in which both the Penicillium IPS promoter functions and the amdS gene can be used to select transformants, as described above. The construction protocol for plasmid pPS54 is described in Example 11.

The ability to transform Penicillium and the present availability of the IPS genes of both Penicillium and Cephalosporium (as described herein and in U.S. patent application Ser. Nos. 895,008, filed Aug. 8, 1986, and 801,523, filed Nov. 25, 1985, and incorporated herein by reference) as well as the DACS/DAOCS gene allow many useful combinations of genes and recipients. For example, the Penicillium IPS gene can be introduced into high producing strains of Penicillium to increase the titer of penicillins produced in a fermentation, as exemplified by the use of plasmid pPS54 and the methods of Examples 18, 19, and 20. Another example is the introduction of the DACS/DAOCS gene into Penicillium via the use of plasmids pIT503, pPS52, pPS56, pPS58, pPS59, pPS60, pPS61, or pPS62 and the methods of Examples 18, 19, and 20, thereby facilitating the unprecedented production of cephalosporins in Penicillium.

Several of the Penicillium expression plasmids are particularly useful when utilized in the methods of selecting transformants described in Examples 18–20. Plasmids p3SR2, pPS51, pPS52, pPS54, and pPS61 contain the amdS gene, and Penicillium cells taking up these plasmids can be selected using the acetamide selection procedure described in Examples 18 and 20. Plasmids pPS57 and pPS62 contain a hybrid hygromycin resistance-conferring gene that utilizes the pIPS promoter. Penicillium cells taking up these plasmids can be selected using the hygromycin B selection method described in Example 19.

A particularly useful aspect of the present invention is the in vivo conversion of penicillin G and penicillin V to the corresponding cephalosporins via the action of the DACS/DAOCS or a modified version thereof in Penicillium. The desired fermentation products, cephalosporin G and cephalosporin V, are organic extractable. The present invention comprises a method for making a cephalosporin in a Penicillium host cell. The method comprises transforming a Penicillium host cell with a recombinant DNA vector that comprises a gene that codes for the expression of DAOCS activity.

The invention described herein is not restricted to the coding sequence of the DACS/DAOCS gene. Because plasmid pIT503 comprises over 3 kb of the genomic DNA that was located upstream of the DACS/DAOCS-encoding DNA in the *Cephalosporium acremonium* genome, plasmid pIT503 necessarily comprises the promoter and translational activating sequence of the DACS/DAOCS gene. Most promoters and associated translational activating sequences are encoded upstream of the DNA to be activated. (Some rRNA-encoding DNA sequences are activated by promoters that are not located upstream of the coding sequence.) "Upstream" is a word used in the art of molecular biology and, in the present context, refers to DNA in the 5' direction from the 5' end of the coding strand of the DACS/DAOCS sequence.

Plasmids pIT503, pPS52, and pPS56 comprise the *Cephalosporium acremonium* promoter and translational activating sequence of the DACS/DAOCS gene. Because the *C.*

*acremonium* promoter and translational activating sequence located on plasmids pIT503, pPS52, and pPS56 can be used to drive expression of a wide variety of DNA sequences, this sequence comprises an important part of the present invention. Although the sequence data on the *C. acremonium* promoter and translational activating sequence is limited, the activating sequence is believed to be encoded on the ~440 bp SstI-HindIII restriction fragment located immediately upstream of and adjacent to the DACS/DAOCS coding sequence. Any restriction fragment that comprises the aforementioned ~440 bp SstI-HindIII restriction fragment necessarily comprises the *C. acremonium* promoter and translational activating sequence. Fragments smaller than the ~440 bp fragment can be examined for promoter activity by conventional methods.

There is sequence data on the *Cephalosporium acremonium* promoter and translational activating sequence encoded on plasmid pIT503. The sequence below is the DNA sequence that is upstream of the coding strand of the DACS/DAOCS gene present on plasmid pIT503 and represents the sequence of the ~440 bp SstI-HindIII restriction fragment. To further clarify how the activating sequence is oriented in plasmid pIT503, the sequence is illustrated with the HindIII cleavage site marked at the 5' (upstream) end and with the "ATG" that encodes the amino-terminal methionine of the DACS/DAOCS gene at the 3' end (the aforementioned SstI site is 60 bp into the coding sequence).

This invention also comprises the transcription termination sequence and other regulatory signals at the 3' end of the DACS/DAOCS gene. Plasmid pIT503, and derivatives such as plasmid pPS56, contain over a kilobase of the DNA downstream of the translation termination site of the DACS/DAOCS gene in the *Cephalosporium acremonium* genome. Part of this 3' regulatory DNA sequence is known and is depicted below. The 5'-TAG-3' is the translation termination sequence:

```
5'-TAG GGA ACC CGC CGA TCG AGT AAT AAA TCT
ACG GGA GTT TAA GAA GAA AAA TTG CCC TAT AAA TTG
CTA AAT TTT TAA AAC ACA AAG CAT GAG TGT CAA GAG
TTT CAA GTT TCA A-3'
```

This sequence, and larger sequences comprising the 3' regulatory sequences of the DACS/DAOCS gene, can be incorporated into recombinant DNA expression vectors.

The present invention is a pioneering invention in that it represents the first cloning and genetic engineering of a DNA sequence that encodes the DAOCS enzymatic activity, often called expandase activity, necessary to transform a penicillin into a cephalosporin. Many organisms other than *Cephalosporium acremonium* express a substantially similar, if not identical, expandase activity. The similarity of

```
DNA Sequence of the Cephalosporium acremonium DACS/DAOCS Promoter
and Translational Activating Sequence Encoded on Plasmid pIT503

HindIII
              10          20          30           40
5'-AAGCTTG TAC GGA GAA TTA AGG CTT GCA CGA TTC CAT GGC GGT CTC 50          60          70          80           90
GAC GAT CAG GGA CCA TGC ACG ATA CAT ATT CTC CTG CGA ACC AAG AAC 100         110         120         130          140
GAG AAG AGA ACT CGA TGG CTT CTT ATG ATT CGT TGA CAA AAC TTC ACA 150         160         170         180         190
AGA CAC TCG TGG GTT TAC AAT GCT ACA TTG ACG TGT GCG GCC AAG GCT 200         210         220         230
GAG GGG AAG CAG GGC GTC ACT TAC GGC TAA GTA GCA GTT GTC TAA AAA 240         250         260         270         280
GGA GTT CCT CGG CGT AAG CTA CGA GGT GGG GTT TGA GAT ATA TAT ATA 290         300         310         320         330
CCG CTT TGA CAA CGT TTC GTT CTC ACT GGG ATC TTG TGA ATC CTT AAA 340         350         360         370         380
TTC CTC TTG CAG AAC TTT CCT CCA CGC TAC TCC TCT CAA GTC ATC GCT 390         400
CAA AAC CAC AGC ATC AAC ATG-3'
                        MET
                        ↑→beginning of DACS/DAOCS protein coding
                        region (the coding sequence).
```

The *Cephalosporium acremonium* promoter and translational activating sequence can be used to drive expression of any DNA sequence. For example, fusion of the DACS/DAOCS promoter to the bacterial hygromycin B resistance-conferring gene will afford advantages and utility for hygromycin B selection in Cephalosporium. Such a hybrid HmR gene can be used as a selectable marker in Cephalosporium.

expandase activity in antibiotic-producing organisms of different genera results from a corresponding similarity of the amino acid sequence of the different expandases and of the DNA sequence encoding the expandase activity.

The present invention provides both an amino acid and a DNA sequence for an expandase enzyme, specifically the DAOC synthetase of *Cephalosporium acremonium*, and thus can be used to isolate expandase enzyme-encoding DNA from β-lactam-producing organisms. The present invention thus comprises any DAOCS-encoding DNA compound that can be isolated on the basis of its homology to any portion of the DACS/DAOCS coding sequence of *C. acremonium*. For instance, the present DNA sequences can be used to prepare labelled probes that can, in turn, be used to find expandase-encoding DNA sequences in the aforementioned 62-lactam-producing organisms. The high G and C content of the present DAOCS-encoding DNA, ~63%, makes the present DNA compounds especially useful for isolating DAOCS-encoding Streptomyces DNA, especially from *S. clavuligerus*. Streptomyces DNA is known to have high G and C content, often approaching 70%, so the high G and C content of the DNA of the present invention makes the present DNA compounds especially useful for isolating homologous *S. clavuligerus* or other streptomycetes DAOCS-encoding DNA sequences. This same homology of DNA sequence allows the DNA compounds of the invention to be used to identify compounds that encode DACS activity or both DACS and DAOCS activity. These homologous compounds comprise an important aspect of the present invention.

The following Examples are provided to further illustrate and exemplify, but do not limit the scope of, the present invention.

EXAMPLE 1
Culture of *E. coli* K12 JA221/pIT503 and Isolation of Plasmid pIT503

A lyophil of *E. coli* K12 JA221/pIT503 is obtained from the Northern Regional Research Laboratories, Peoria, Ill. under the accession number NRRL B-18170. The lyophil can be directly used as the "culture" in the process described below.

One liter of L broth (10 g tryptone, 10 g NaCl, and 5 g yeast extract per liter) containing 50 μg/ml ampicillin was inoculated with a culture of *E. coli* K12 JA221/pIT503 and incubated in a gyrotory incubator at 37° C. until the optical density at 590 nm (O.D.$_{.590}$) was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue.

The culture was centrifuged in a Sorvall GSA rotor (DuPont Co., Instrument Products, Biomedical Division, Newtown, Conn. 06470) at 6000 rpm for 5 minutes at 4° C. The resulting supernatant was discarded, and the cell pellet was washed in 40 ml of TES buffer (10 mM Tris-HCl, pH=7.5; 10 mM NaCl; and 1 mM EDTA) and then repelleted. The supernatant was discarded, and the cell pellet was frozen in a dry ice-ethanol bath and then thawed. The thawed cell pellet was resuspended in 10 ml of a solution of 25% sucrose and 50 mM EDTA. About 1 ml of a 5 mg/ml lysozyme solution; 3 ml of 0.25 M EDTA, pH=8.0; and 100 μl of 10 mg/ml RNAse A were added to and mixed with the solution and then incubated on ice for 15 minutes. Three ml of lysing solution (prepared by mixing 3 ml of 10% Triton-X 100; 75 ml of 0.25 M EDTA, pH=8.0; 15 ml of 1 M Tris-HCl, pH=8.0; and 7 ml of water) were added to the lysozyme-treated cells, mixed, and the resulting solution incubated on ice for another 15 minutes. The lysed cells were frozen in a dry ice-ethanol bath and then thawed.

The cellular debris was removed from the solution by centrifugation at 25,000 rpm for 40 minutes in an SW27 rotor (Beckman, 7360 N. Lincoln Ave., Lincolnwood, Ill. 60646). The supernatant was extracted with buffered phenol.

About 30.44 g of CsCl and ~1 ml of a 5 mg/ml ethidium bromide solution were added to the solution, which was then adjusted to a volume of 40 ml and decanted into a VTi50 ultracentrifuge tube (Beckman). The tube was sealed, and the solution was centrifuged in a VTi50 rotor at 42,000 rpm for ~16 hours. The resulting plasmid band, visualized with ultraviolet light, was isolated and then placed in a Ti75 tube and rotor (Beckman) and centrifuged at 50,000 rpm for 16 hours. Any necessary volume adjustments were made using TES containing 0.761 g/ml CsCl. The plasmid band was again isolated, extracted with salt-saturated isopropanol to remove the ethidium bromide, and diluted 1:3 with TES buffer. Two volumes of ethanol were added to the solution, which was then incubated at −20° C. overnight. The plasmid DNA was pelleted by centrifuging the solution in an SS34 rotor (Sorvall) for 15 minutes at 10,000 rpm.

The ~1 mg of plasmid pIT503 DNA obtained by this procedure was suspended in 1 ml of TE buffer (10 mM Tris-HCl, pH=8.0 and 1 mM EDTA) and stored at −20° C. A restriction site and function map of plasmid pIT503 is presented in FIG. 1 of the accompanying drawings.

EXAMPLE 2
Construction of Plasmid pIT507
A. Construction of Plasmid pKEN021 and Isolation of its ~5.1 kb XbaI-BamHI Restriction Fragment The isolation of the ~5.1 kb XbaI-BamHI restriction fragment of plasmid pKEN021 (106 in FIG. 4) is set forth in this Example section. Plasmid pKEN021 is a derivative of plasmid pKEN111 (101 in FIG. 2 and further described in Lee et al., 1981, J. Bact. 146: 861–866 and Zwiebel et al., 1981, J. Bact. 145: 654–656). Plasmid pKEN111 can be obtained from the Northern Regional Research Center (NRRL), Agricultural Research Service, Peoria, Ill. 61604, in *E. coli* CC620 under the accession number NRRL 15011. Plasmid pKEN111 has an ~2.8 kb EcoRI restriction fragment that contains the *E. coli* lpp gene (see Nakamura and Inouye, 1979, Cell 18: 1109–1117).

In plasmid pKEN021, the 650 bp EcoRI-SalI restriction fragment of plasmid pBR322 has been replaced by *E. coli* lpp gene sequences. The lpp gene sequences include a 462 bp AluI fragment located upstream from the first triplet of the lpp coding sequence. This 462 bp fragment contains the promoter, 5' untranslated region, and ribosome binding site. A unique XbaI restriction site is located within the ribosome binding site 16 bp before the translation-initiating methionine codon. A PvuII restriction site located 105 bp upstream from the translation termination codon of the lpp coding sequence was changed to a BamHI restriction site by the addition of a synthetic DNA linker (5'-CCGGATCCGG-3', Collaborative Research Inc., 128 Spring Street, Lexington, Mass. 02173). The coding sequence for the last thirty-five amino acids of lipoprotein, the translation termination signal, and the sequence corresponding to the 3' untranslated region of the messenger RNA follow the BamHI site. Plasmid pKEN021 also includes some 850 bp of extraneous sequences located downstream of the lpp gene in the *E. coli* chromosome. These sequences were included as a consequence of the methods and restriction enzyme sites used in the original isolation of the gene and in no way limit the invention.

Figure 2:
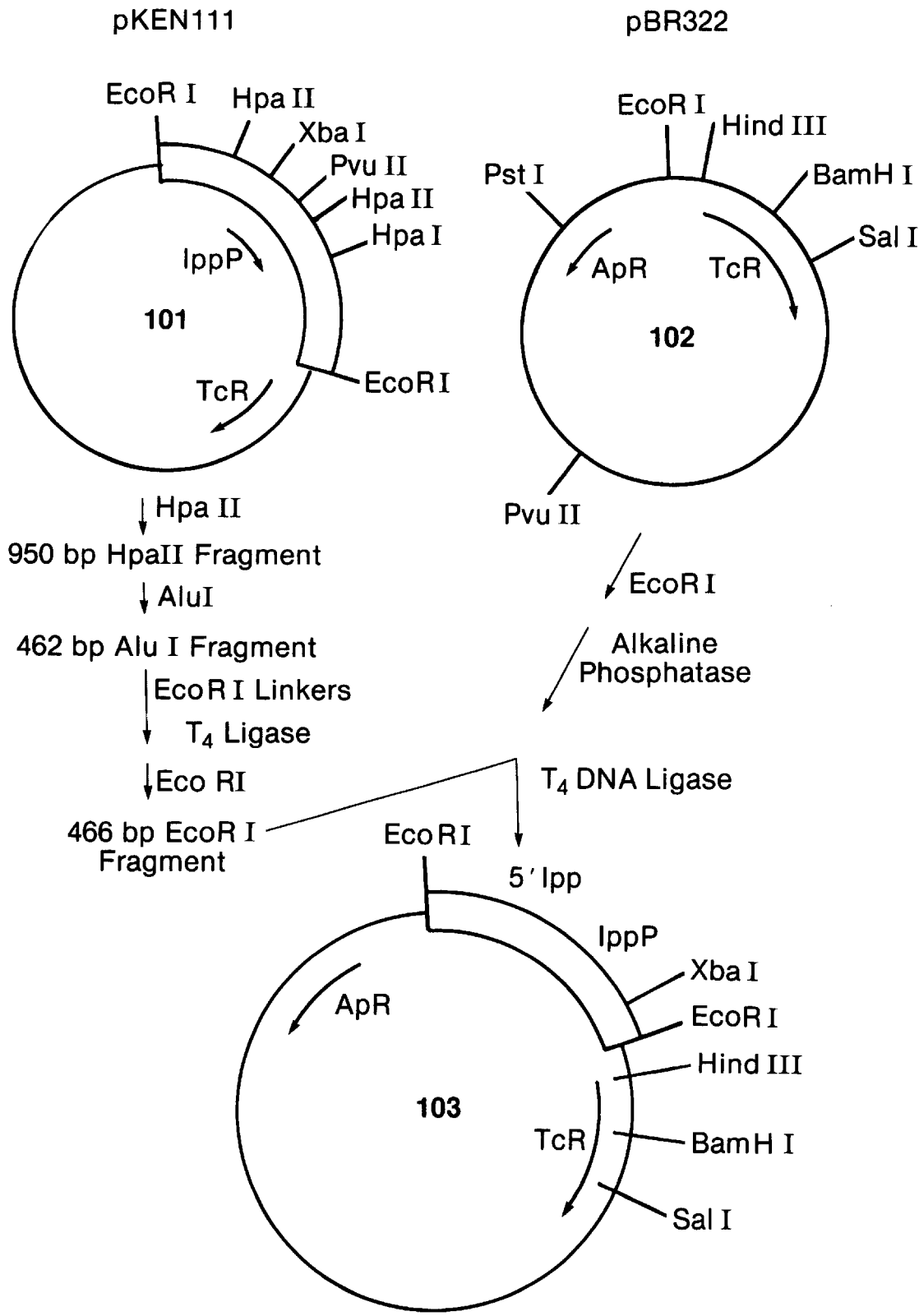
FIG. 2. Restriction site and function maps, derivitizations, and relationships of plasmids pKEN111 (101), pBR322 (102), and 103, intermediate plasmids in the construction of plasmid pCZR336.
Figure 3:
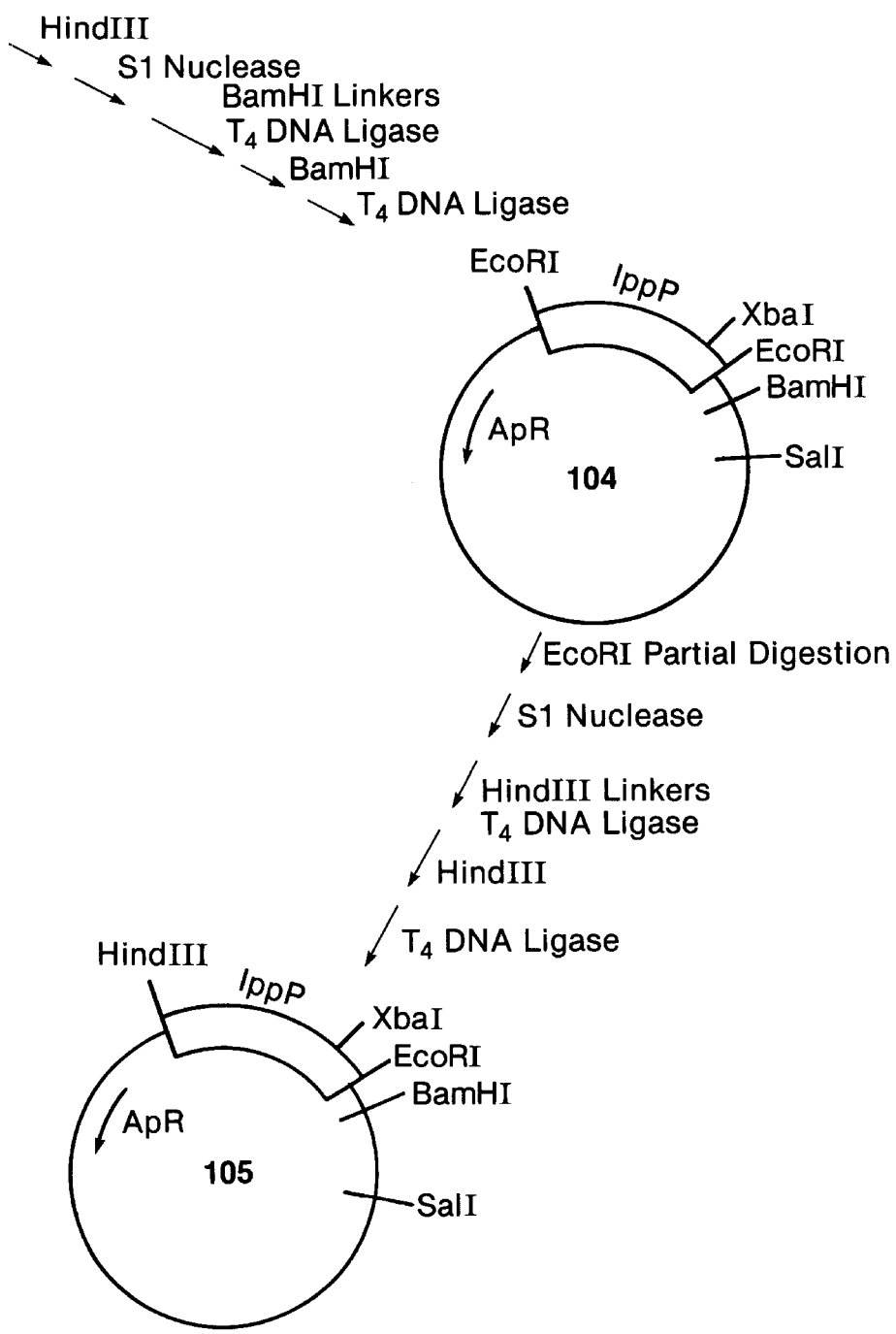
FIG. 3. Restriction site and function maps, derivitizations, and relationships of plasmids 103, 104, and 105, intermediate plasmids in the construction of plasmid pCZR336.
Figure 4:
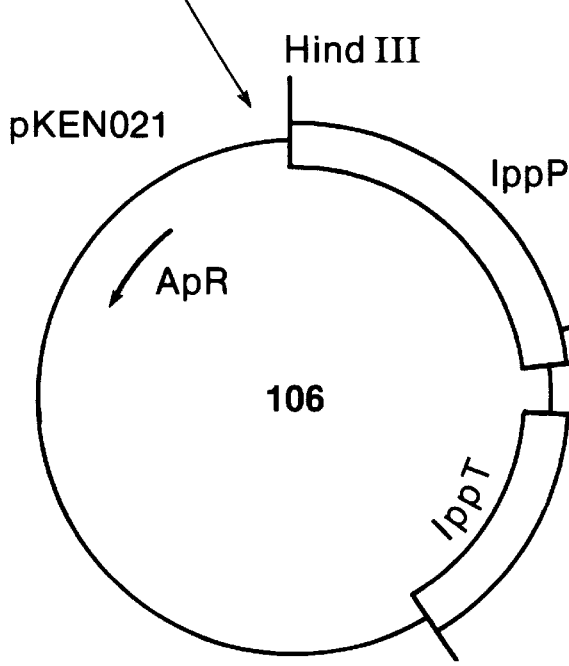
FIG. 4. Restriction site and function maps, derivitizations, and relationships of plasmids pKEN021 (106 and 107) and pKEN111 (101), intermediate plasmids in the construction of plasmid pCZR336.
Figure 4:
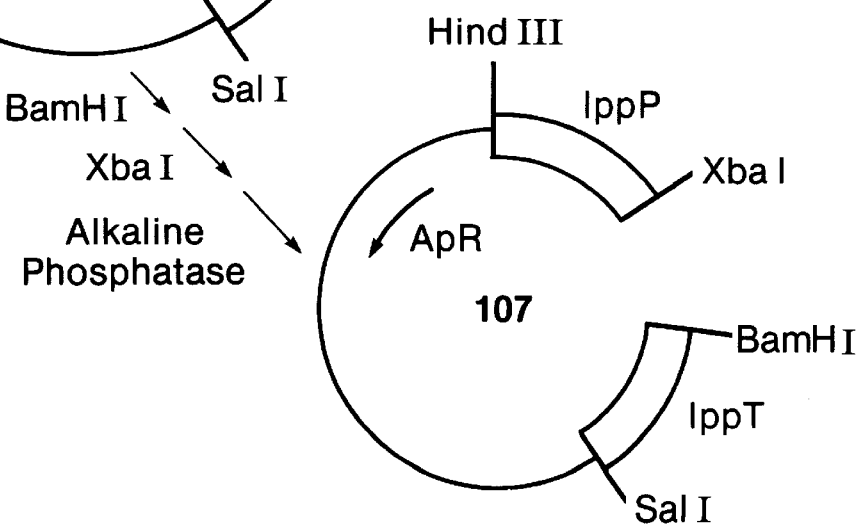

As depicted in FIGS. 2, 3, and 4, plasmid pKEN021 is derived from plasmid pKEN111 as follows. About 50 μg of plasmid pKEN111 (101 in FIG. 2) are digested with 25 units of HpaII restriction enzyme (unless otherwise indicated, restriction enzymes and unit definitions refer to those of New England Biolabs, 32 Tozer Road, Beverly, Mass. 01915) in 300 μl of 1×HpaI buffer (10 mM Tris.HCl, pH=7.4; 10 mM MgCl$_2$; 20 mM KCl; and 6 mM β-mercaptoethanol) at 37° C. for 2 hours. The mixture is extracted twice with 300 μl of a 50:50 mixture of phenol and chloroform, and the recovered aqueous phase is precipitated with 2.5 volumes of ethanol and 0.1 volume of 3 M sodium acetate (NaOAc). The DNA pellet is dissolved in 100 μl of electrophoresis buffer and fractionated on a 5% polyacrylamide gel (acrylamide:bis ratio is 29:1 in all polyacrylamide gels except where otherwise noted). The gel is stained in a solution containing 0.5 μg/ml of ethidium bromide, and the DNA bands are visualized under long wave-length ultraviolet (UV) light. A 950 bp HpaII restriction fragment is isolated and recovered from the gel by electroelution into a dialysis bag. After phenol/CHCl$_3$ extraction and ethanol precipitation, the recovered DNA (~2.5 μg) is dissolved in 25 μl of TEN (10 mM NaCl; 10 mM Tris.HCl, pH=7.4; and 1 mM sodium ethylene-dinitrilotetraacetate (EDTA)).

About 2 μg of the 950 bp HpaII fragment are digested with AluI restriction enzyme in 200 μof 1×AluI buffer (50 mM NaCl; 6 mM Tris.HCl, pH=7.6; 6 mM MgCl$_2$; and 6 mM β-mercaptoethanol) for 2 hours at 37° C. The DNA is fractionated on a 6% polyacrylamide gel and the 462 bp AluI fragment is recovered and purified as described above. The 462 bp AluI fragment (~1 μg) is dissolved in 10 μl of T4 DNA ligase buffer (66 mM Tris.HCl, pH=7.6; 10 mM MgCl$_2$; 10 mM dithiothreitol; and 0.4 mM ATP) containing 150 picomoles of phosphorylated EcoRI linker (5'-GGAATTCC-3', from Collaborative Research) and 2 units T4 DNA ligase. After incubation at 4° C. for 16 hours, the mixture is heated at 65° C. for 10 minutes and then diluted to 100 μl so as to have the composition of 1×EcoRI buffer (100 mM Tris.HCl, pH=7.2; 50 mM NaCl; 10 mM MgCl$_2$; and 6 mM β-mercaptoethanol) containing 40 units of EcoRI enzyme. After 2 hours at 37° C., the sample is extracted with phenol/CHCl$_3$ and precipitated with ethanol. The DNA is then dissolved in 20 μl of T4 DNA ligase buffer containing T4 DNA ligase and 0.1 μg of EcoRI-digested, alkaline phosphatase-treated plasmid pBR322 (102 in FIG. 2). After ligation at 4° C. for 16 hours, the resulting DNA is used to conventionally transform *E. coli* K12 HB101 (NRRL B-15626). Transformants are selected on agar plates containing 12 μg/ml of tetracycline and plasmids isolated from resistant colonies by the rapid alkaline extraction procedure described in Birnboim and Doly, 1979, Nucleic Acids Research 7: 1513–1523. A plasmid (103 in FIG. 2) containing a 466 bp XbaI-BamHI fragment is selected and used as the starting material for the step next described.

About 2 μg of this plasmid (103 in FIG. 3) are digested with 2 units of HindIII enzyme in 50 μl of 1×HindIII buffer (60 mM NaCl; 10 mM Tris.HCl, pH=7.4; 10 mM MgCl$_2$; and 6 mM β-mercaptoethanol) for 1 hour at 37° C. After the reaction mixture is extracted with phenol/CHCl$_3$ and precipitated with ethanol, the DNA is dissolved in 200 μl of 1×S1 nuclease buffer (300 mM NaCl; 30 mM NaOAc, pH=4.25; and 3 mM ZnCl$_2$) containing 200 units of S1 nuclease (Miles Laboratories, 30 W. 475, N. Aurora Road, Naperville, Ill. 60566). After 1 hour at 15° C., the reaction is stopped by extraction with phenol/CHCl$_3$ and the DNA precipitated with ethanol. The HindIII-digested, nuclease-treated DNA is dissolved in 10 μl of T4 DNA ligase buffer containing 20 picomoles of phosphorylated BamHI linkers (5'-CCGGATCCGG-3', from Collaborative Research) and 2 units of T4 DNA ligase. After 16 hours at 4° C., the reaction mixture is heated at 65° C. for 10 minutes to inactivate the ligase and then diluted to 100 μl to obtain the composition of 1×BamHI buffer (150 mM NaCl; 20 mM Tris.HCl, pH=8.0; 10 mM MgCl$_2$; and 6 mM β-mercaptoethanol) containing 20 units of BamHI enzyme. After 2 hours at 37° C., the mixture is purified on a 1% agarose gel. The gel is stained with ethidium bromide, and the larger fragment (~4.5 kb) is recovered by cutting the band from the gel, eluting the fragment after freezing the agarose slice, and then purifying by phenol/CHCl$_3$ extraction and ethanol precipitation. Alternatively, the desired fragment can be isolated from the agarose gel using NA45 membrane (Schleicher and Schuell, Keene N.H. 03431) according to the manufacturer's recommendations.

The recovered fragment has BamHI cohesive ends and is dissolved in 20 μl of T4 DNA ligase buffer containing T4 DNA ligase. After 16 hours at 4° C., the DNA is used to transform *E. coli* K12 HB101 (NRRL B-15626). Transformants are selected by screening for resistance to ampicillin (ApR) at 100 μg/ml and for sensitivity to tetracycline (TcS) at 10 μg/ml. Several plasmids, prepared by the previously described Birnboim procedure, from ApR, TcS colonies are examined for the absence of a HindIII site and presence of a single BamHI site. EcoRI, SalI sequential digestion yields two smaller fragments, 466 bp and 305 bp in size, and a much larger fragment. A plasmid (104 in FIG. 3) with these characteristics is selected and then modified to convert the EcoRI site, located upstream of the lpp promoter, to a HindIII restriction site.

This modification is accomplished by first partially digesting 2 μg of the plasmid (104 in FIG. 3) in 100 μl of 1×EcoRI buffer with restriction enzyme EcoRI. The reaction is stopped by heat inactivation at 65° C. and then, after phenol/CHCl$_3$ extraction of the reaction mixture, the DNA is ethanol precipitated. The DNA pellet is dissolved in 200 μl of 1×S1 nuclease buffer containing 1000 units/ml of S1 nuclease and incubated at 12° C. for 1 hour. The reaction is stopped by phenol/CHCl$_3$ extraction, and the DNA is precipitated with ethanol. The DNA pellet is resuspended in 10 μl of T4 DNA ligase buffer containing 20 picomoles of phosphorylated HindIII linker (5'-CCAAGCTTGG-3', from Collaborative Research) and 2 units of T4 DNA ligase. After 16 hours at 4° C., the mixture is heated for 10 minutes at 65° C., diluted to 150 μl to obtain the composition of 1×HindIII buffer containing 10 units of HindIII restriction enzyme, incubated for 2 hours at 37° C., and then fractionated on a 1% agarose gel. The largest band (equivalent to linear, full-length plasmid) is conventionally recovered, purified, dissolved in 20 μl of T4 ligase buffer containing T4 ligase, incubated 16 hours at 4° C., and used to transform *E. coli* HB101 (NRRL B-15626). The plasmid DNA of ApR transformants is analyzed by restriction enzyme analysis. A plasmid (105 in FIG. 3) with an ~500 bp EcoRI-HindIII fragment is selected. This plasmid is then used as the cloning vector for the 340 region of the lpp gene.

About 2 μg of this plasmid (105 in FIG. 4) are digested in 50 μl of 1×SalI buffer (150 mM NaCl; 6 mM Tris.HCl, pH=7.9; 6 mM MgCl$_2$; and 6 mM β-mercaptoethanol) with 2 units of SalI enzyme for 1 hour at 37° C. The SalI reaction mixture is then diluted to 150 μl to obtain the composition of 1×BamHI buffer containing 2 units of BamHI enzyme. After 1 hour at 37° C., about 2.5 units of alkaline phosphatase are added, and the mixture is incubated at 65° C. for 1 hour. The material is phenol/CHCl$_3$ extracted, ethanol precipitated, dissolved in TEN, and used as a cloning vector for the lpp 3' fragment.

To obtain the lpp 3' fragment, 10 μg of plasmid pKEN111 (101 in FIG. 2) are digested in 200 μl of 1×HpaI buffer containing 10 units of HpaI enzyme for 2 hours at 37° C. After phenol/CHCl$_3$ extraction and ethanol precipitation, the DNA is dissolved in 10 μl of T4 DNA ligase buffer containing 20 picomoles of phosphorylated SalI linker (5'-GGTCGACC-3', from Collaborative Research) and T4 DNA ligase and then incubated for 16 hours at 4° C. The ligase is inactivated by heating at 65° C. for 10 minutes. The resultant material is diluted to 100 µl to obtain the composition of 1×SalI buffer containing 10 units of SalI enzyme and incubated for 1 hour at 37° C. The reaction mixture is diluted to 300 µl to obtain the composition of 1×PvuII buffer (60 mM NaCl; 6 mM Tris.HCl, pH=7.5; 6 mM MgCl₂; and 6 mM β-mercaptoethanol) containing 10 units of PvuII enzyme. After 1 hour at 37° C., the DNA is fractionated on a 5% polyacrylamide gel. Approximately 0.5 µg of the 950 bp fragment is recovered, purified, and dissolved in TEN.

Two-tenths microgram of this fragment is diluted into 20 µl T4 DNA ligase buffer containing 20 picomoles of phosphorylated BamHI linker (5'-CCGGATCCGG-3', from Collaborative Research) and 2 units of T4 DNA ligase and then incubated for 16 hours at 4° C. The resultant DNA is then heated for 10 minutes at 65° C., diluted to 100 µl to obtain the composition of 1×BamHI buffer containing 20 units of BamHI enzyme, incubated at 37° C. for 2 hours, and then fractionated on a 5% polyacrylamide gel to remove excess linker molecules. The resulting 950 bp fragment with BamHI and SalI cohesive ends is conventionally purified and dissolved in 20 µl of T4 DNA ligase buffer containing 0.2 µg of the BamHI-SalI-digested plasmid 105 and T4 DNA ligase. After incubation for 16 hours at 4° C., the DNA is used to transform *E. coli* K12 HB101 (NRRL B-15626). Plasmids are prepared from ApR transformants and analyzed for the SalI-BamHI fragment. The desired plasmid (~5.2 kb) is designated pKEN021 (106 in FIG. 4).

Ten µg of plasmid pKEN021 were digested at 37° C. in 200 µl of BamHI buffer containing 10 units each of BamHI and XbaI enzyme for one hour at 37° C. The desired XbaI-BamHI-digested DNA was then treated with 2.5 units of alkaline phosphatase for 1.5 hours at 65° C., phenol/CHCl₃ extracted, collected by ethanol preciitation, and dissolved in 50 µl of TEN for future use (107 in FIG. 4).

B. Construction of Plasmid pNM575

Plasmid ptrpED50chGH800 (108 in FIG. 5), described in Martial et al., 1979, Science 205: 602–607, was used as the source of DNA containing a portion of the hGH coding sequence. This fragment can be constructed synthetically or obtained using recognized methodology, described by Goodman et al., 1979, Methods in Enzymology 68:75–90, by isolating mRNA coding for hGH from human pituitaries. The hGH portion of plasmid ptrpED50chGH800 contains a unique SmaI restriction site 6 bp downstream from the translation termination codon of the coding sequence. This site was changed to a BamHI site as described below.

About 6 µg of plasmid ptrpED50chGH800 were digested with 6 units of SmaI in 200 µl of 1×SmaI buffer (15 mM Tris.HCl, pH=8.0; 6 mM MgCl₂; 15 mM KCl; and 6 mM β-mercaptoethanol) for 1.5 hours at 37° C. After digestion was complete, phenol/CHCl₃ extraction was performed, and the DNA was recovered by ethanol precipitation and then dissolved in 24 µl of TEN. Forty picomoles of phosphorylated BamHI linker (Collaborative Research) were added to 0.5 µg (0.2 picomole of ends) of the above-digested plasmid in 16 µl of ligase buffer containing T4 DNA ligase. The mixture was incubated for 2 hours at 22° C., 16 hours at 4° C., and then 10 minutes at 65° C. BamHI cohesive termini were generated by conventional digestion with BamHI restriction enzyme. The enzyme cleaved the linker sequence as well as the BamHI site located at the beginning of the cloned hGH cDNA sequence. This digestion yielded a 691 bp fragment with cohesive BamHI ends, which was separated on a 6% polyacrylamide gel and then conventionally recovered.

Figure 5:
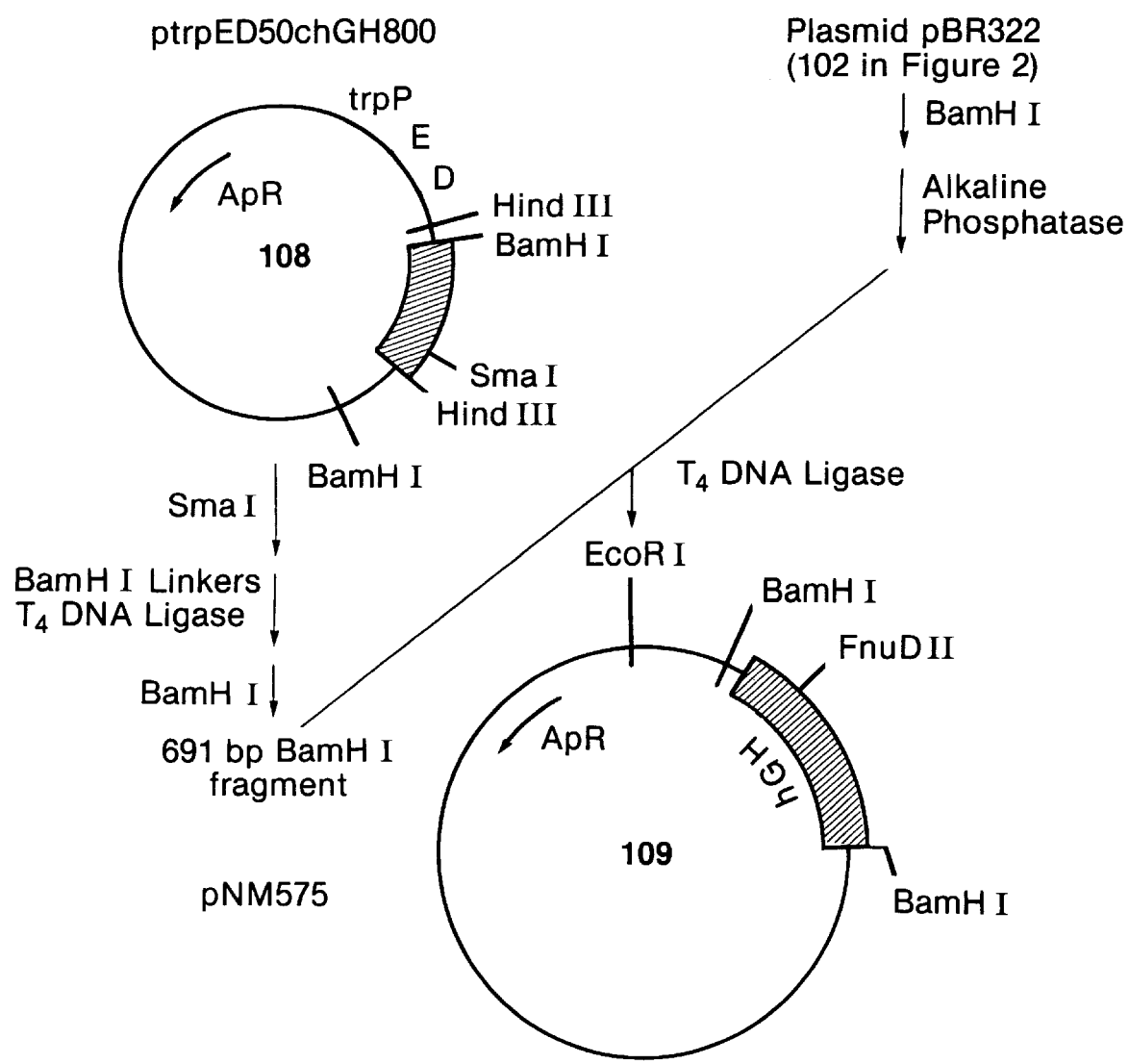
FIG. 5. Restriction site and function maps, derivitizations, and relationships of plasmids ptrpED50chGH800 (108), pBR322 (102), and pNM575 (109), intermediate plasmids in the construction of plasmid pCZR336.

The recovered DNA fragment was ligated with 0.2 µg of BamHI-digested and alkaline phosphatase-treated plasmid pBR322 (FIG. 5). After 16 hours at 4° C., the material was used to transform *E. coli* K12 JA221 (NRRL B-15014) in substantial accordance with the transformation procedure of Wensink et al., 1974, Cell 3:315–325. Transformants were selected on agar plates containing 100 µg/ml ampicillin, and plasmids were conventionally isolated and identified by restriction enzyme and gel electrophoretic analysis. Desired plasmids, designated as pNM575 (109 in FIG. 5), contain an ~700 bp BamHI fragment and were conventionally amplified (Example 1) for future use.

C. Construction of Plasmid p1101

Figure 6:
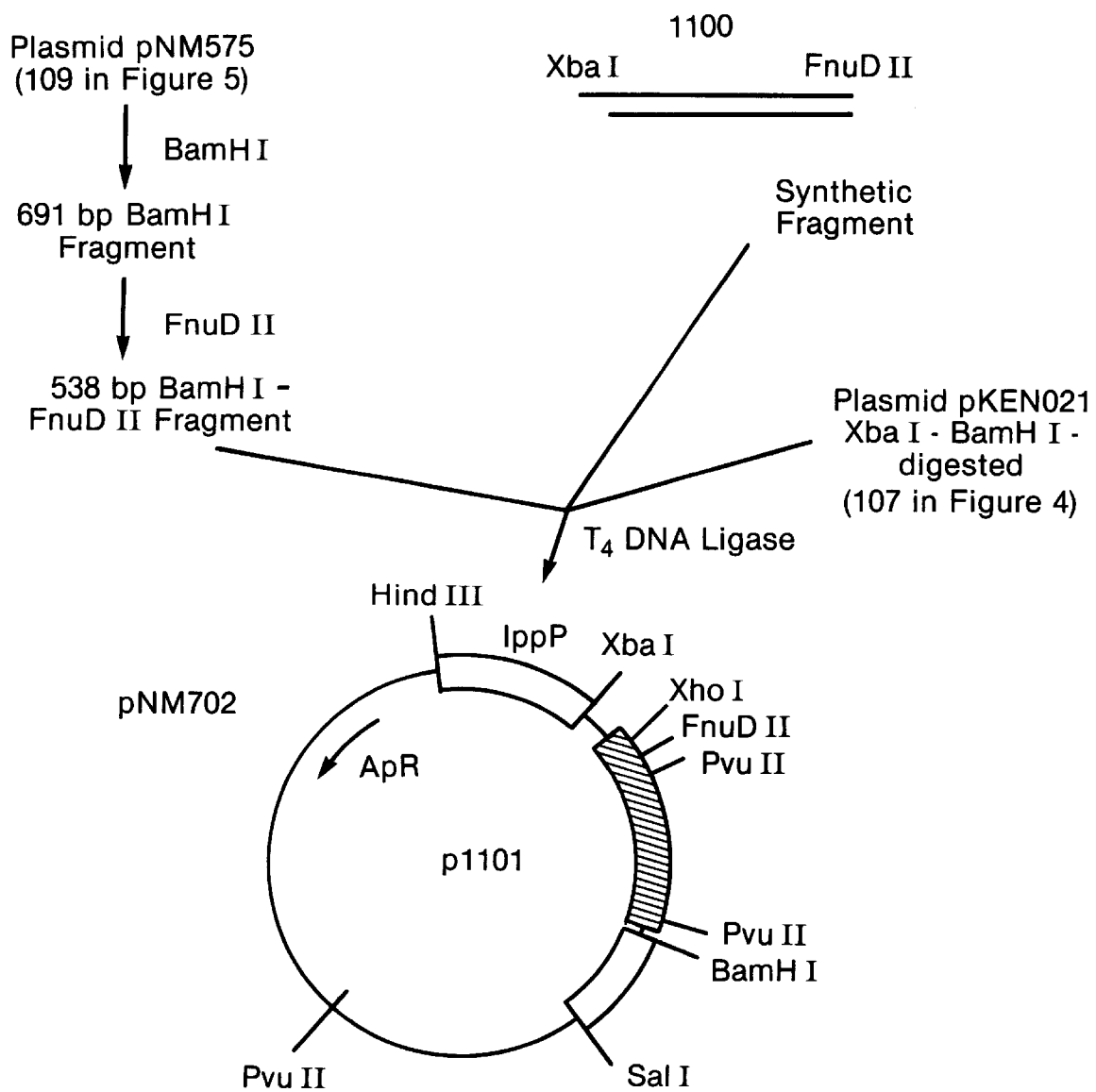
FIG. 6. Restriction site and function maps, derivitizations, and relationships of plasmids pNM575 (109), pKEN021 (107), and pNM702 (p1101), intermediate plasmids in the construction of plasmid pCZR336.

The coding sequence of mature hGH contains one FnuDII site that is ~47 bp from the first nucleotide of the translation initiation site. About 25 µg of plasmid pNM575 are digested in 250 µl of BamHI buffer with 25 units of BamHI enzyme at 37° C. for 1 hour (FIG. 6). The 691 bp BamHI fragment is conventionally isolated from a 6% polyacrylamide gel and purified. After purification, one third of the fragment (equivalent to 8 µg of plasmid) is digested in 100 µl of FnuDII buffer (6 mM NaCl; 6 mM Tris.HCl, pH=7.4; 6 mM MgCl₂; and 6 mM β-mercaptoethanol) with 2.5 units of FnuDII enzyme for 1.5 hours at 37° C. Electrophoresis on a 6% polyacrylamide gel and standard recovery procedures are used to isolate a 538 bp DNA fragment containing the coding sequence for the last 175 amino acids of hGH followed by a translation stop signal.

A double-stranded DNA fragment (1100 in FIG. 6) is synthesized by the phosphotriester method to join the lpp promoter region with the hGH coding region. The double stranded DNA fragment (1100 in FIG. 6) has the following sequence:

The fragment is prepared by recognized phosphotriester methodology by which the following segments are prepared: 1) 5'-CTAGAGGGTA-3'; 2) 5'-TTACATATGGATTTCC-3'; 3) 5'-CAACCATTCCCCTCTCGAGGC-3'; 4) 5'-TTTTTGACAACG-3'; 5) 5'-CTATGCTCCG-3'; 6) 5'-CGGAGCATAGCGTT-3'; 7) 5'-GTCAAAAAGCCT-3'; 8) 5'-CGAGAGGGGAAT-3'; 9) 5'-GGTTGGGAAATC-3'; and 10) 5'-CATATGTAATACCCT-3'. Using the above-prepared segments, the T4 ligase catalyzed joining reactions are performed stepwise as described below:

a) 5'-Unphosphorylated segment 1 is mixed with phosphorylated segments 2, 9, and 10 and subjected to the action of T4 ligase to form DNA duplex 1 (Brown et al., 1979, Methods in Enzymology 68:109–151). The duplex is isolated by preparative gel electrophoresis on 15% polyacrylamide.

b) 5'-unphosphorylated segment 6 is mixed with phosphorylated segments 3, 4, 5, 7, and 8 and subjected to the action of T4 DNA ligase to form DNA duplex 2.

The duplex is purified by 15% polyacrylamide gel electrophoresis.

c) The DNA duplexes 1 and 2 then are joined together by T4 ligase to form DNA duplex 1100 (FIG. 6), which is purified by 10% polyacrylamide gel electrophoresis. This DNA duplex then is enzymatically phosphorylated using T4 polynucleotide kinase and γ-$^{32}$P-ATP by following established procedure.

The expression plasmid p1101 is constructed by ligating 0.1 picomole (0.4 µg) of the XbaI-BamHI fragment of plasmid pKEN021 (107 in FIG. 4), 0.025 picomoles synthetic DNA fragment (1100 in FIG. 6), and 0.3 picomoles (0.08 µg) of the 538 bp fragment of plasmid pNM575 in 24 µl of ligation buffer using T4 DNA ligase. After incubation for 16 hours at 4° C., the mixture is used to transform *E. coli* JA221 (NRRL B-15014). Transformants are selected on agar plates containing 100 µg/ml ampicillin and are conventionally cultured as a preferred source of the desired expression plasmid p1101.

D. Construction of Plasmid p1103

The sequence of the hGH gene in plasmid p1101 contains an XhoI site beginning 24 bases downstream of the translation initiation site and an XbaI site in the 5' noncoding region. About 25 µg of plasmid p1101 are digested in 250 µl of BamHI buffer with 25 units of XbaI and 25 units of XhoI at 37° C. for 1 hour. The large fragment, which runs slightly faster than linear plasmid, is purified from an agarose gel as described in Example 2A.

A double stranded DNA fragment is synthesized by the phosphotriester method to incorporate a short open reading frame (cistron) in front of the hGH coding sequence. The double stranded DNA fragment has the following sequence:

The fragment is prepared by recognized phosphotriester methodology by which the following segments are prepared:
1) 5'-CTAGAGGGTATTAATAATGTATATTGATTTTAATAAGGAG-3';
2) 5'-GAATAATCATATGGATTTCCCAACCATTCCCCTC-3';
3) 5'-TCGAGAGGGGAATGGTTGGGAAATCCATATGATTATTCCTCCTT-3' and
4) 5'-ATTAAAATCAATATACATTATTAATACCCT-3'.

Figure 7:
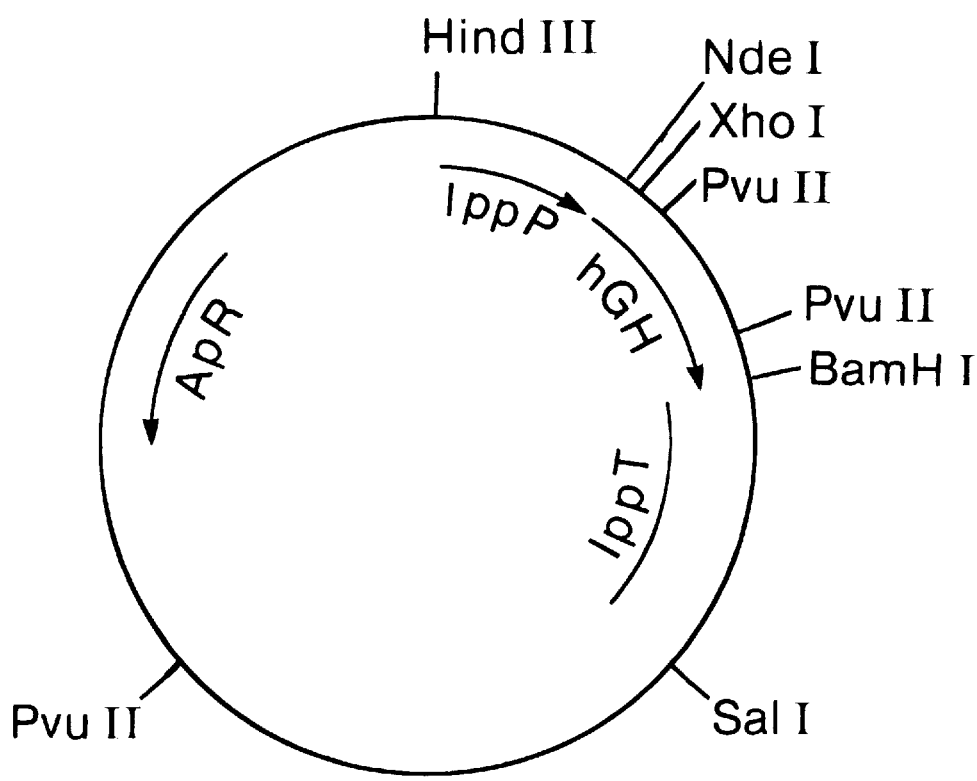
FIG. 7. Restriction site and function map of plasmid p1103, an intermediate plasmid in the construction of plasmid pCZR336.

Using the above-prepared segments, the T4-ligase catalyzed joining reactions are performed by mixing 5'-unphosphorylated segments 1 and 3 with 5'-phosphorylated segments 2 and 4 and subjecting the mixture to the action of T4 ligase. The resulting duplex is then purified by 10% polyacrylamide gel electrophoresis. This DNA duplex then is enzymatically phosphorylated using T4 polynucleotide kinase and γ-$^{32}$P-ATP by following established procedure. The hGH expression plasmid p1103 is constructed by ligating 0.1 picomoles (0.4 µg) of the XbaI-XhoI fragment of plasmid p1101 to 0.025 picomoles of the synthetic DNA fragment in 24 µl ligation buffer using T4 DNA ligase. After incubation for 16 hours at 4° C., the mixture is used to transform *E. coli* JA221 (NRRL B-15014). Transformants are selected on agar plates containing 100 µg/ml ampicillin and are conventionally cultured as a preferred source of the desired expression plasmid p1103 (FIG. 7).

E. Construction of *E. coli* K12 RV308/pL110A

Plasmid pL110 is disclosed in Examples 1–11 of U.S. patent application Ser. No. 769,221, filed Aug. 26, 1985, attorney docket number X-6638, incorporated herein by reference. A restriction site and function map of plasmid pL110 is presented in FIG. 8 of the accompanying drawings.

About 1 µg of plasmid pL110 DNA was digested with restriction enzyme NdeI in 20 µl total volume containing 2 µl of 10×high-salt buffer (1.0 M NaCl; 0.50 M Tris.HCl, pH=7.5; 0.10 M MgCl$_2$; and 10 mM dithio-threitol) and 3 units of NdeI enzyme for 1 hour at 37° C. The reaction mixture was extracted with phenol/chloroform and the DNA precipitated with ethanol. The NdeI-digested plasmid pL110 DNA was dissolved in 50 µl of 1×Klenow buffer (40 mM KPO$_4$, pH=7.5; 6.6 mM MgCl$_2$; 1.0 mM 2-mercaptoethanol; 33 µM dATP; 33 µM dCTP; 33 µM dGTP; and 33 µM TTP). Two µl (~10 units, New England Biolabs) of the large fragment of *E. coli* DNA polymerase I, known as Klenow, were added to and mixed with the DNA, and the resulting reaction was incubated at 16° C. for 1 hour. The reaction was terminated by phenol extraction and the DNA conventionally purified. The NdeI-digested, Klenow-treated DNA was then ligated with T4 DNA ligase at 4° C. for 16 hours. The resulting DNA was used to conventionally transform *E. coli* K12 strain RV308 (NRRL B-15624). Transformants were selected on L-agar plates containing 100 µg/ml ampicillin and plasmids isolated from resistant colonies by the rapid alkaline extraction procedure described by Birnboim and Doly. A plasmid (pL110A in FIG. 8) lacking an NdeI site was selected.

F. Construction of Phage pL110B by Site-Specific Mutagenesis

Figure 8:
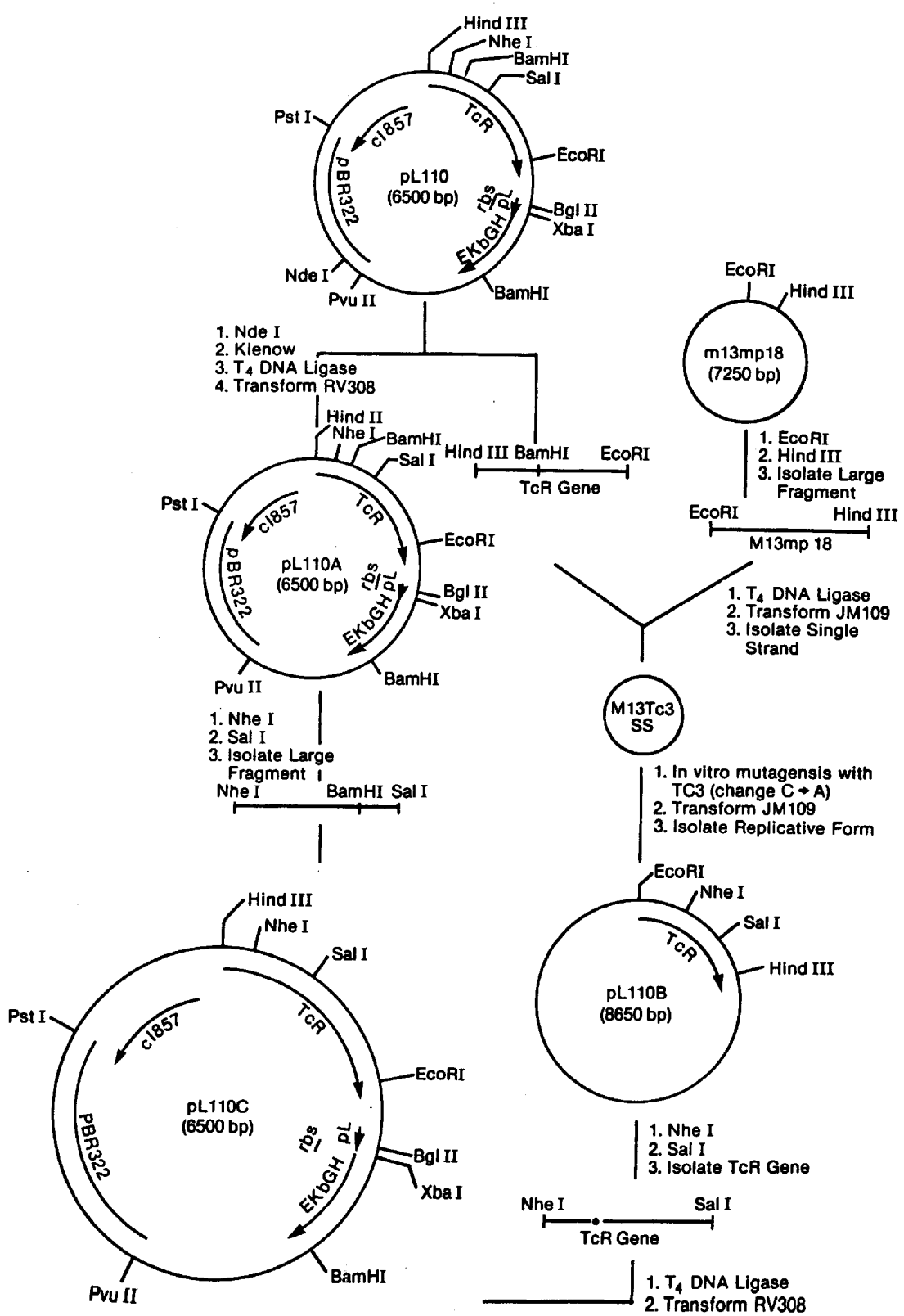
FIG. 8. Restriction site and function maps, derivitizations, and relationships of plasmids pL110, pL110A, and pL110C and bacteriophages m13mp18, m13Tc3, and pL110B, intermediate vectors in the construction of plasmid pCZR336.

The protocol for eliminating the BamHI site in the tetracycline resistance-conferring gene by site-specific mutagenesis is shown on the right hand side of FIG. 8 of the accompanying drawings.

F(i) Construction of Phage M13Tc3

Plasmid pL110 served as the source of the tetracycline resistance-conferring gene. About 50 µg of plasmid pL110 in 50 µl of TE buffer were added to 25 µl of 10×HindIII buffer and 170 µl of H$_2$O. About 5 µl (~50 units) of restriction enzyme HindIII were added to the solution of plasmid pL110 DNA, and the resulting reaction was incubated at 37° C. for 2 hours. About 13 µl of 2 M Tris.HCl, pH=7.4, and 5 µl (~50 units) of restriction enzyme EcoRI were added to the HindIII-digested plasmid pL110 DNA, and the reaction was incubated for 2 more hours at 37° C. The reaction was stopped by extracting the reaction mixture with TE-saturated phenol; the phenol was removed by chloroform extractions. The EcoRI-HindIII-digested plasmid pL110 DNA was then collected by precipitation and centrifugation, loaded into a 1% agarose gel, and the large ~4.3 kb EcoRI-HindIII restriction fragment was isolated and purified.

About 5 µg of phage m13mp18 (New England Biolabs) were dissolved in 50 µl of TE buffer and then digested with HindIII and EcoRI as described above. The HindIII-EcoRI-cut phage M13mp18 DNA was purified as described for pL110 except that an ~7.25 kb restriction fragment was isolated and purified.

About 100 nanograms of the ~4.3 kb HindIII-EcoRI fragment of plasmid pL110 were mixed with about 100 nanograms of the ~7.25 kb HindIII-EcoRI fragment of phage M13mp18, 2 μl of 10×ligase buffer, 1 μl (~100 units) of T4 DNA ligase, and 14 μl of H$_2$O. The ligation reaction was incubated at 15° C. for 1.5 hours; the ligated DNA constituted the desired phage m13Tc3 DNA. A restriction site and function map of phage m13Tc3 is presented in FIG. 8 of the accompanying drawings.

One ml of an overnight culture of *E. coli* K12 JM109 (*E. coli* K12 JM101, available from New England Biolabs, can be used instead of *E. coli* K12 JM109) was used to inoculate 50 ml of L broth, and the resulting culture was incubated at 37° C. with aeration until the O.D.$_{660}$ was between 0.3 and 0.4. The cells were resuspended in 25 ml of 10 mM NaCl, incubated on ice for 10 minutes, and collected by centrifugation. The cells were resuspended in 1.25 ml of 75 mM CaCl$_2$; a 200 μl aliquot of the cells was removed, added to 10 μl of the ligated DNA prepared above, and incubated on ice for about 40 minutes. The cell-DNA mixture was then incubated at 42° C. for 2 minutes, and varying aliquots (1, 10, and 100 μl) were removed and added to 3 ml of top agar (L broth with 0.5% agar kept molten at 45° C.) that also contained 50 μl of 2% X-Gal, 50 μl of 100 mM IPTG, and 200 μl of *E. coli* K12 JM109 in logarithmic growth phase. The cell-top agar mixture was then plated on L-agar plates containing 40 μg/ml X-Gal (5-bromo-4-chloro-3-indolyl-β-D-thiogalactoside) and 0.1 mM IPTG (isopropyl-β-D-thiogalactoside), and the plates were incubated at 37° C. overnight.

The following morning, several clear, as opposed to blue, plaques were individually used to inoculate 2 ml of L broth, and the resulting cultures were incubated at 37° C. with aeration for 2 hours. The absence of blue color indicates the desired DNA insertion occurred. Then, the cultures were centrifuged, and 200 μl of the resulting supernatant were added to 10 ml cultures (O.D.$_{550}$=0.5) of *E. coli* K12 JM109 growing at 37° C. with aeration. These cultures were incubated for another 30 minutes at 37° C.; then, the cells were pelleted by centrifugation and used to prepare the replicative-form of the recombinant phage they contained. Double-stranded, replicative form phage DNA was isolated from the cells using a scaled-down version of the procedure described in Example 1. Transformants containing phage m13Tc3 DNA were identified by restriction enzyme analysis of their phage DNA.

F(ii) Preparation of Single-Stranded Phage m13Tc3 DNA

One and one-half ml of an overnight culture of *E. coli* K12 JM109/m13Tc3 were centrifuged, and 100 μl of the phage m13Tc3-containing supernatant were used to inoculate a 25 ml culture of *E. coli* JM109 at an O.D.$_{660}$ of about 0.4–0.5. The culture was incubated for 6 hours at 37° C. with aeration, at which time the culture was centrifuged and the resulting supernatant, about 20 ml, transferred to a new tube. About 2 ml of a solution containing 20% polyethylene glycol (PEG) 6000 and 14.6% NaCl were added to the supernatant, which was then incubated on ice for 20 minutes.

The supernatant was centrifuged for 25 minutes at 7000 rpm, and the resulting pellet, which contained single-stranded phage m13Tc3 DNA, was resuspended in 500 μl of TE buffer. The DNA solution was extracted twice with TE-saturated phenol and twice with chloroform. The single-stranded DNA was then precipitated using NaOAc and ethanol and centrifuged. The resulting pellet was washed with 70% ethanol, dried, and then dissolved in 60 μl of H$_2$O.

F(iii) Mutagenesis

The single-stranded DNA fragment used in the mutagenesis was synthesized on an automated DNA synthesizer. The fragment has the sequence, 5'-CCCGTCCTGTGGATACTCTACGCCGA-3', and is homologous to the region surrounding the BamHI site (5'-GGATCC-3') in the tetracycline resistance-conferring gene from plasmid pBR322, except that the A residue second from the 5' end (or third from the 3' end) is a C in plasmid pBR322. This change does not alter the amino acid composition of the tetracycline resistance-conferring protein but eliminates the BamHI site.

About 10 picomoles of the mutagenic primer and the M13 universal primer (Bethesda Research Laboratories (BRL), P.O. Box 6009, Gaithersburg, Md. 20760) were individually treated with 10 units (BRL) of T4 polynucleotide kinase in 20 μl of 1×kinase buffer (60 mM Tris-HCl, pH=7.8; 15 mM 2-mercaptoethanol; 10 mM MgCl$_2$; and 0.41 μM ATP) for 30 minutes at 37° C. The kinase-treated DNAs were used in the mutagenesis procedure described below.

The annealing reaction was carried out mixing together 300 nanograms (1.2 μl) of single-stranded phage m13Tc3, 1 picomole (2 μl) of the universal primer, 1 picomole (2 μl) of the mutagenic primer, 2 μl of 10×annealing buffer (100 mM Tris-HCl, pH=7.5; 1 mM EDTA and 500 mM NaCl), and 12.8 μl of H$_2$O. The reaction was incubated at 80° C. for 2 minutes, at 50° C. for 5 minutes, and then allowed to cool to room temperature.

The extension reaction was carried out by adding 5 μl of 10×extension buffer (500 mM Tris-HCl, pH=8; 1 mM EDTA; and 120 mM MgCl$_2$); 5 μl of 2 mM dATP; 1 μl of a solution 6 mM in each of dGTP, TTP, and dCTP; 1 μl (~2 units, Pharmacia P-L Biochemicals, 800 Centennial Avenue, Piscataway, N.J. 08854) of Klenow enzyme; 1 μl (100 units) of T4 DNA ligase; and 17 μl of H$_2$O to the mixture of annealed DNA. The extension reaction was incubated at room temperature for 1 hour, then at 37° C. for 2.5 hours, and then overnight at 4° C.

The reaction was stopped by two extractions with TE-saturated phenol, which were followed by two extractions with CHCl$_3$. The DNA was precipitated with ethanol and NaOAc. The DNA was collected by centrifugation and resuspended in 50 μl of H$_2$O, and 6 μl of 10×S1 buffer were then added to the solution of DNA.

The solution of DNA was split equally into three tubes. About 200 units (Miles Laboratories) of S1 nuclease were added to two of the tubes. One S1 reaction was incubated at room temperature for 5 minutes, the other for 10 minutes. The reactions were stopped by extracting the reaction mixture twice with TE-saturated phenol. The phenol extractions were followed by two extractions with chloroform; then, the DNA was precipitated from the reaction mixture with NaOAc and ethanol. The untreated sample of DNA served as a negative control. The S1-treated samples were kept separate from each other throughout the remainder of the procedure but gave similar results.

The DNA pellets were resuspended in 20 μl of H$_2$O, and 10 μl of the resulting solution were used to transform *E. coli* K12 JM109 (*E. coli* K12 JM101 could also be used) in accordance with the procedure used during the construction of phage m13Tc3, except that no IPTG or X-Gal was added to the plates.

Double-stranded replicative form DNA from about 48 plaques was isolated as described above and screened for the presence of a BamHI restriction site. Isolates without a BamHI site were further screened by preparing single-stranded DNA as described above. The single-stranded DNA was sequenced using the dideoxy sequencing method (J. H. Smith, 1980, Methods in Enzymology 65: 560–580). The desired isolate was designated pL110B (FIG. 8).

G. Construction of Plasmid pL110C

About 50 μg of the replicative form of phage pL110B DNA were digested in 250 μl of 1×NheI buffer (50 mM NaCl; 6 mM Tris.HCl, pH=7.5; 6 mM MgCl$_2$; and 6 mM β-mercaptoethanol) containing ~50 units of NheI restriction enzyme at 37° C. for 2 hours. Five μl of 5 M NaCl were then added to the NheI-digested phage pL110B DNA, followed by 5 μl (~50 units) of SalI restriction enzyme. Digestion was continued for 2 hours at 37° C. The desired ~422 bp NheI-SalI fragment containing the mutated region of the tetracycline resistance-conferring gene was then isolated from an acrylamide gel.

Plasmid pL110A DNA was digested with NheI and SalI under identical conditions, except that plasmid pL110A was substituted for phage pL110B. The ~6.1 kb NheI-SalI restriction fragment of plasmid pL110A was purified from agarose.

The desired plasmid pL110C was constructed by ligating together 100 nanograms each of the NheI-SalI fragments of pL110A (~6.1 kb) and pL110B (~422 bp) using conventional procedures. The desired plasmid pL110C confers tetracycline resistance to 10 μg/ml tetracycline in *E. coli* but lacks a BamHI site in the tetracycline resistance-conferring gene.

H. Construction of Plasmid pCZR111

Figure 9:
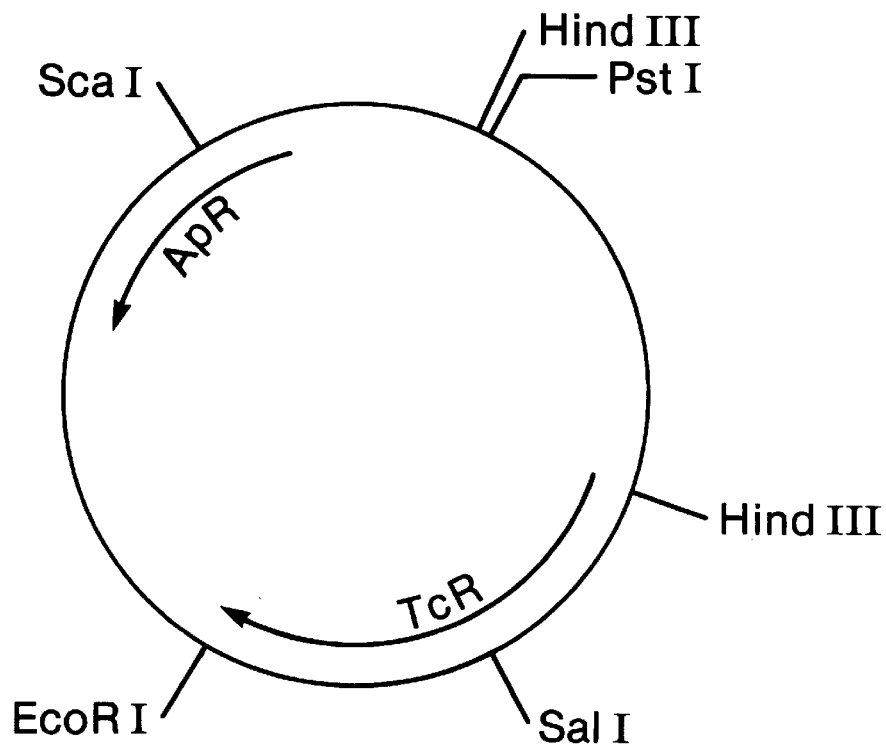
FIG. 9. Restriction site and function map of plasmid pIT160.

Plasmid pCZR111 (available from the NRRL under accession number NRRL B-18249) can be constructed by ligating an ~3.5 kb EcoRI-PstI restriction fragment of plasmid pL110C (containing an intact bGH coding sequence) to the ~3 kb EcoRI-PstI restriction fragment of plasmid pIT160. Plasmid pIT160 contains an ~3.0 kb EcoRI-PstI restriction fragment derived from plasmid pL110C inserted into EcoRI-PstI-digested plasmid pUC18 (New England Biolabs). This 3.0 kb fragment contains the tetracycline resistance-conferring gene of plasmid pL110C, except that the ClaI site has been removed. A restriction site and function map of pIT160 is presented in FIG. 9 of the accompanying drawings. Plasmid pIT160 can be obtained from *E. coli* K12 JM109/pIT160, available from the NRRL under accession number NRRL B-18185, in substantial accordance with the procedure of Example 1. Plasmid pIT160 confers resistance to 10 μg/ml tetracycline and lacks a ClaI restriction site. The tetracycline resistance-conferring gene of plasmid pIT160 can be purified on a PstI-EcoRI restriction fragment for use in the construction of plasmid pCZR111.

Figure 10:
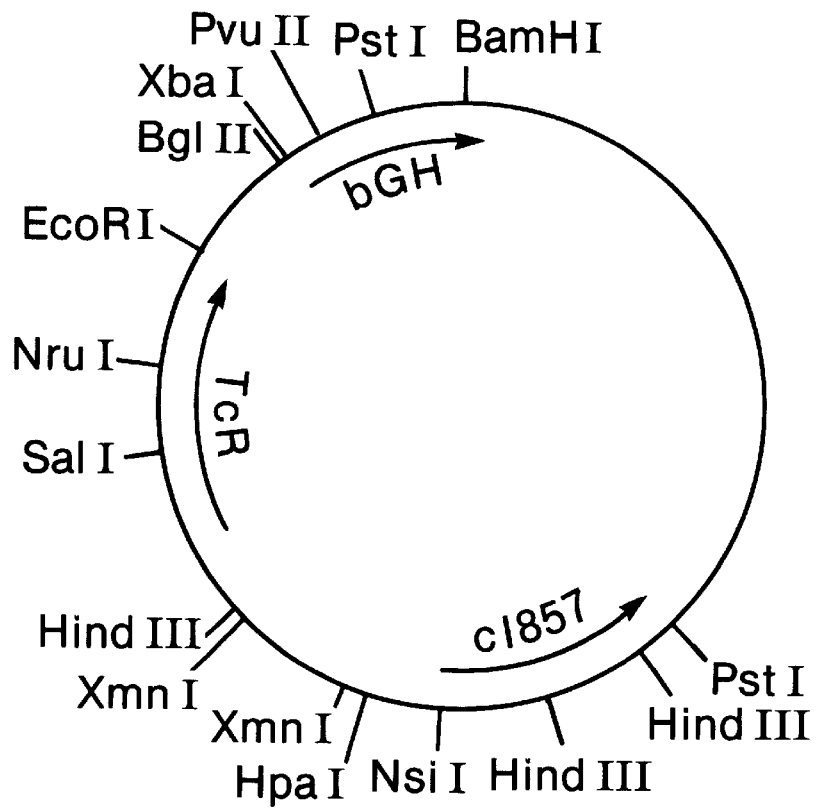
FIG. 10. Restriction site and function map of plasmid pCZR111.

About 50 μg of plasmid pL110C DNA (Example 2G) are incubated in 250 μl total volume of 1×EcoRI buffer containing 10 μl (~50 units) of EcoRI for 2 hours at 37° C. Then, 1 μl (~5 units) of PstI restriction enzyme is added, and incubation is continued at 37° C. Aliquots are removed about every five minutes and extracted with phenol/CHCl$_3$. The aliquots are pooled, and the mixture is electrophoresed on an agarose gel. The desired ~3.5 kb EcoRI-PstI fragment contains the intact bGH gene and includes an internal PstI site (not cut during the partial PstI digestion). The desired fragment is separated from the undesired fragments: an ~2.5 kb PstI-PstI fragment that contains only part of the bGH gene; an ~3 kb EcoRI-PstI fragment that contains the tetracycline resistance-conferring gene; and an ~6.5 kb EcoRI fragment (undigested by PstI). The ~3.5 kb PstI-EcoRI fragment is purified and ligated to the ~3 kb PstI-EcoRI fragment of plasmid pIT160. The ligated DNA is used to transform *E. coli* K12 JM109, and the desired plasmid, designated pCZR111 and shown in FIG. 10 of the accompanying drawings, is isolated from the transformants and characterized using conventional procedures.

I. Construction of Plasmid pCZR336

Plasmid pCZR336 is an hGH expression vector constructed from the XbaI-BamHI backbone of plasmid pCZR111 (Example 2H) and the two-cistron, hGH construction from plasmid p1103 (Example 2D and FIG. 7). About 50 μg of plasmid p1103 are incubated in 250 μl of 1×high-salt buffer containing ~50 units each of BamHI and XbaI restriction enzyme for 2 hours at 37° C. The ~650 bp XbaI-BamHI fragment containing the first cistron and hGH coding sequence gene is isolated and purified from an acrylamide gel. About 50 μg of plasmid pCZR111 (Example 2H) are also digested with XbaI and BamHI enzymes, and the large XbaI-BamHI fragment is purified from agarose. The two XbaI-BamHI restriction fragments are ligated together, and the ligated DNA is used to transform *E. coli* K12 RV308 (NRRL B-15624) using conventional procedures. The desired plasmid pCZR336 (FIG. 11) is identified from among the transformants by plasmid isolation followed by restriction enzyme analysis.

J. Construction of Plasmid p1104

Plasmid pCZR336 is an expression vector that utilizes the λpL promoter. To join the DACS/DAOCS to the λpL promoter in plasmid pCZR336, it was necessary to utilize a synthetic DNA linker. This linker joins the NdeI site of plasmid pCZR336 to the SstI site in the DACS/DAOCS coding sequence and has the structure depicted below:

This linker was synthesized on an automated DNA synthesizer as two separate single strands using conventional procedures. This linker has several differences from the native Cephalosporium sequence, none of which affect the protein encoded by the resulting coding sequence. These changes include: 1) creation of an NdeI site containing the translation initiation site; 2) a C to A change in the third position of codon 10, which remains a leucine codon as CTC and CTA are equivalent, to create an XbaI site; and 3) a C to T change in the third position of the fifth codon, which remains a valine codon as GTC and GTT are equivalent.

To facilitate future cloning efforts, the linker is first cloned into plasmid pUC19 (New England Biolabs). About 5 μg of plasmid pUC19 are dissolved in 50 μl of 1×SstI buffer (50 mM NaCl; 50 mM Tris.HCl, pH=7.5; and 10 mM MgCl$_2$) containing ~10 units of SstI enzyme (BRL). The reaction is incubated for 2 hours at 37° C. The NaCl concentration of the reaction mixture is then increased to 150 mM by adding 1 μl of 5 M NaCl. About 2 μl (10 units) of NdeI enzyme are added and the mixture incubated another 2 hours at 37° C. The DNA is then precipitated and collected by centrifugation.

Figure 13:
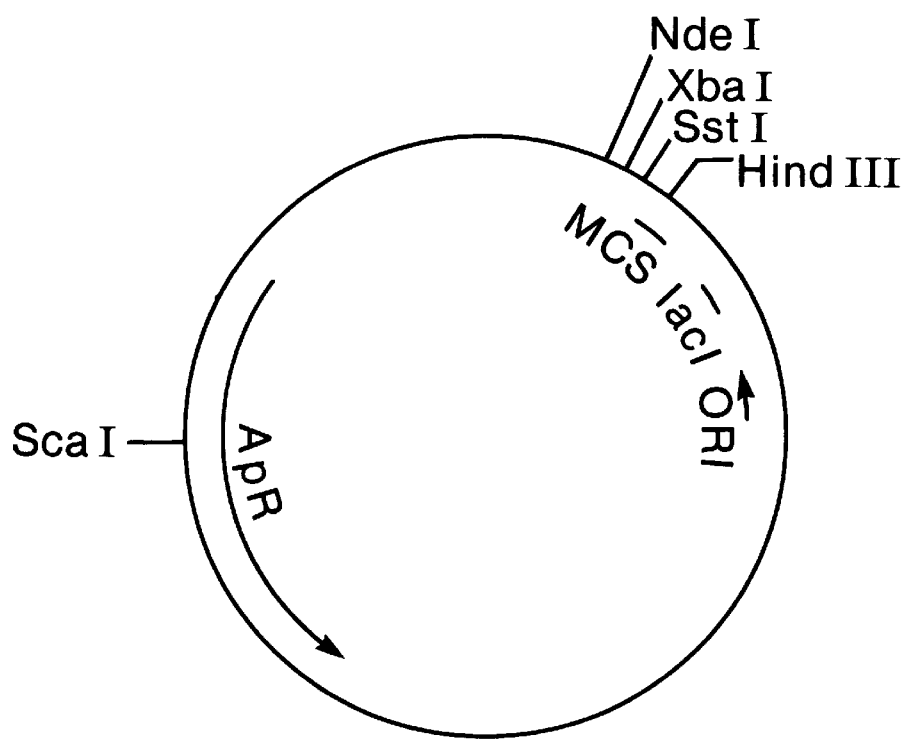
FIG. 13. Restriction site and function map of plasmid p1104.

About 100 nanograms of the SstI-NdeI-digested plasmid pUC19 are mixed with 1 picomole of the synthetic linker in ligase buffer with T4 DNA ligase. The ligated DNA is used to transform *E. coli* K12 JM109 cells, and aliquots of the mixture are plated on L-agar (L broth with 15 grams per liter agar) plates containing 100 μg/ml of ampicillin, 40 μg/ml of X-gal, and 40 μg/ml of IPTG. The plates are incubated at 37° C. overnight. Colonies that contain a plasmid without an insert, such as E. coli K12 JM109/pUC19, appear blue on these plates. Colonies that contain a plasmid with an insert, such as E. coli K12 JM109/p1104, are white. Several white colonies are selected and screened by restriction analysis of their plasmid DNA for the presence of the ~60 bp NdeI-SstI fragment with the same sequence as the synthetic fragment above. A representative isolate of the desired construction is designated plasmid p1104 (FIG. 13).

K. Final Construction of Plasmid pIT507

Plasmid pIT507 is constructed by ligating the DACS/DAOCS coding sequence-containing SstI-BamHI fragment of plasmid pIT503 to the NdeI-SstI insert of plasmid p1104 and to the NdeI-BamHI-cleaved backbone of plasmid pCZR336. The ~2.2 kb SstI-BamHI restriction fragment of plasmid pIT503 (Example 1) is obtained by complete digestion with BamHI and partial digestion with SstI (another SstI site is located ~50 bp from the BamHI site in the desired ~2.2 kb fragment).

About 50 μg of plasmid pIT503 are dissolved in 250 μl of 1×SstI buffer containing ~50 units of BamHI and the reaction mixture is placed at 37° C. for 2 hours. Then, one μl (~10 units) of SstI enzyme is added, and the reaction is allowed to proceed at 37° C. Aliquots are removed every 5 minutes, quenched by phenol/CHCl$_3$, and the DNA precipitated and pelleted by centrifugation. The ~2.2 kb SstI-BamHI fragment containing the majority of the expandase/hydroxylase coding sequence is isolated and purified from a 7% acrylamide gel.

About 50 μg of plasmid pCZR336 DNA (Example 2I) are suspended in 250 μl of high-salt buffer containing about 50 units each of NdeI and BamHI restriction enzyme, and the mixture is placed at 37° C. for 2 hours. The ~5.8 kb NdeI-BamHI restriction fragment of plasmid pCZR336, which lacks the hGH coding sequence, is then isolated from an agarose gel.

About 100 μg of plasmid p1104 (Example 2J) are suspended in 500 μl of 1×SstI buffer containing about 100 units of SstI enzyme, and the reaction mixture is placed at 37° C. for 2 hours. The concentration of NaCl is then increased from 50 mM to 150 mM by adding 10 μl of 5 M NaCl. About 20 μl (~100 units) of NdeI enzyme are added, and the mixture is incubated an additional 2 hours at 37° C. The desired ~60 bp NdeI-SstI fragment is purified from a 15% acrylamide gel.

About 100 nanograms of the ~5.8 kb NdeI-BamHI fragment of plasmid pCZR336, ~100 nanograms of the ~2.2 kb SstI-BamHI fragment of plasmid pIT503, and ~50 nanograms of the ~60 bp SstI-NdeI fragment of plasmid p1104 are ligated together with T4 DNA ligase. The ligated DNA is used to transform E. coli K12 JM109 cells using conventional procedures, except that the cells were grown at 30° C. instead of 37° C. (to prevent transcription from λpL). The ligated DNA is mixed with 100 μl of competent JM109 cells (commercially available from Stratagene Corp., 3770 Tansy Street, San Diego, Calif. 92121), incubated at 4° C. for one hour, then incubated for 1 minute at 42° C., and then diluted with 2 ml of fresh L broth and incubated at room temperature (without shaking) for one hour. Aliquots are plated on L-agar plates containing 10 μg/ml tetracycline. The plates are incubated at 30° C. The E. coli K12 JM109/pIT507 transformants are identified by restriction enzyme analysis of their plasmid DNA. A restriction site and function map of plasmid pIT507 is presented in FIG. 11 of the accompanying drawings.

EXAMPLE 3

Assay of E. coli -produced DACS/DAOCS Activity

A. Culture of E. coli K12 JM109/pIT507 for Expression of DACS/DAOCS Activity

An E. coli K12 JM109/pIT507 transformant (Example 2K) was grown at 30° C. overnight in 500 ml of L broth (containing 10 μg/ml of tetracycline) at 250 rpm in a gyrotory incubator. The cells were diluted 1:10 by adding 100 ml of the overnight culture to 900 ml of fresh medium containing 10 μg/ml tetracycline in a 2.8 L Fernbach flask and incubated a further hour at 30° C. under the same growth conditions. The temperature of the air shaker was then raised to 42° C. and incubation continued for an additional 6.5 hours. The cI857 temperature-sensitive repressor of the lambda pL promoter, positioned to drive DACS/DAOCS expression on plasmid pIT507, is inactivated at 42° C. and so allows for expression of DACS/DAOCS. After induction, the cells were harvested by centrifugation and used as a preferred source of E. coli-produced DACS/DAOCS activity.

B. Demonstration of Expandase and Hydroxylase Activities in the E. coli K12 JM109/pIT507 Cells Grown at 42° C.

Expandase/hydroxylase activity was determined essentially as disclosed in U.S. patent application Ser. No. 905,601, filed Sep. 10, 1986, attorney docket number X-6961, incorporated herein by reference. About 14 g (wet weight) of E. coli K12 JM109/pIT507 cells, prepared as described in Example 3A, were resuspended in Tris-GEDA buffer (15 mM Tris.HCl, pH=7.5; 10% glycerol; 10% ethanol; 10 mM dithiothreitol; and 10 mM ascorbate) to a total volume of 20 ml. The cells were disrupted by sonication at a temperature of 4° C. or below by three 30-second bursts at full power. During sonication, multiple additions of phenylmethylsulfonyl fluoride (PMSF) were made until the final concentration was 2 mM. DNAse and magnesium sulfate were added to achieve concentrations of 1 μg/ml and 2 mM, respectively. The sonicated suspension was centrifuged at 40,000×g for 30 minutes. The supernatant provided a crude extract of the DACS/DAOCS enzyme.

The crude extract, in a volume of 13 ml, was loaded onto a 50 ml DEAE-Trisacryl column previously equilibrated with 15 mM Tris-GEDA, pH=7.5. The column was washed with 4 column volumes of 15 mM Tris-GEDA buffer, and then a linear gradient of 0.015 mM Tris-GEDA to 0.3 mM Tris-GEDA was applied. Five ml fractions were collected at a flow rate of 15 ml/hour. The enzyme was eluted as one major activity peak; the DAOCS (expandase) and the DACS (hydroxylase) activities eluted with the same retention time.

The enzymatic activities were determined using an HPLC-based assay. The expandase-catalyzed reaction is conducted for 15 minutes at 30° C. with 0.28 mM penicillin N, 0.60 mM α-ketoglutarate (α-KG), 0.06 mM ferrous sulfate, 0.67 mM ascorbate, 1.00 mM dithiothreitol, 0.05 mM ATP, and 0.0003–0.003 units of the enzyme in 1 ml of 50 mM Tris.HCl, pH=7.5. The hydroxylase-catalyzed reaction is conducted at 36° C. in the same medium with deacetoxycephalosporin C at a concentration of 0.05 mM instead of penicillin N.

The enzymatic reactions were interrupted by the addition of 1 ml of ethyl alcohol. The precipitate is separated by centrifugation at 4,000×g for 5 minutes. The supernatant containing the enzyme reaction products is assayed by HPLC as follows. The expandase activity is determined by monitoring formation of both DAOC and DAC from penicillin N because of the apparent bifunctionality of the enzyme. The hydroxylase activity is determined by monitoring the formation of DAC from DAOC.

Aliquots (20 to 100 µl) of the supernatant solutions are assayed for DAOC and DAC by HPLC using external standards. A preferred HPLC system comprises the components: Model 721 system controller, Model 730 data module, Model 510EF pumps, Model 710B Waters Intelligent Sample Processor, and a Lambda-Max Model 481 LC spectrophotometer (Waters Assoc., Milfor, Mass.). DAC and DAOC are preferably separated by a radially-packed, compressed microBondpak-NH4 column (0.8×10 cm) (Waters Assoc.) with a mobile phase of 2% acetic acid; 0.4% methyl alcohol; 6–7% acetonitrile; 87–92% water; and pH=3.8. The flow rate is 1.5–2.0 ml/min, and detection is at 260 nm (cephalosporin chromophore). The assays are reproducible with 2% deviations for duplicate analyses of both the expandase and the hydroxylase catalyzed reactions. For expandase assays, quantitation for DAC (in addition to that of DAOC) is corrected for penicillin N due to coelution. The results of the assay are summarized below.

Figure 15:
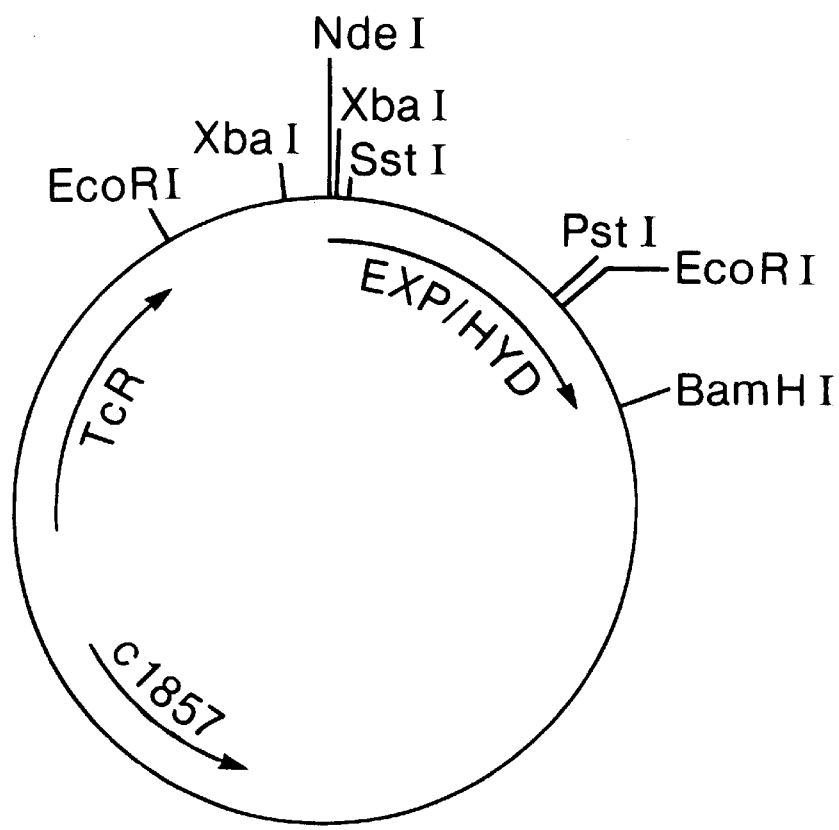
FIG. 15. Restriction site and function map of plasmid pIT511.

About 50 µg of plasmid p1105 are dissolved in 250 µl of 1×high-salt buffer containing about 50 units each of NdeI and BamHI restriction enzyme, and the mixture is incubated for 2 hours at 37° C. The ~1.1 kb NdeI-BamHI fragment is purified from an acrylamide gel. About 100 nanograms of this purified fragment are mixed with 100 nanograms of the large NdeI-BamHI fragment of plasmid pCZR336 (Example 2K), and the mixture is ligated and transformed into *E. coli* K12 JM109. The desired *E. coli* K12 JM109/pIT511 transformants are identified by restriction enzyme analysis of their plasmid DNA. A restriction site and function map of plasmid pIT511 is presented in FIG. 15 of the accompanying drawings. *E. coli* K12 JM109/pIT511 cells can be used as a source of DACS/DAOCS activity in accordance with the procedure described in Example 3.

EXAMPLE 5
Construction of Plasmid pIT512

Amino acid residues can be added or deleted from the DACS/DAOCS gene product via genetic modification. An Partial Purification of DAOCS and DACS from 14 g of *E. coli* K12 JM109/pIT511

| Step | protein, mg | DACS Activity milliU[1] | DACS Specific Activity milliU/mg protein | DAOCS Activity milliU | DAOCS Specific Activity milliU/mg | DAOCS Fold, Purification | DACS/ DAOCS Recovery |
|---|---|---|---|---|---|---|---|
| Crude, extract | 588 | N.D.[2] | N.D. | 2570 | 4.5 | ≡1 | ≡100% |
| DEAE-Trisacryl | 30 | 49.7 | 1.7 | 456 | 15.2 | 3.5 | 18 |

[1]milliU = nanomoles product found per min per ml extract
[2]Not determined

EXAMPLE 4
Construction of Plasmid pIT511

Plasmid pIT507 (Example 2K) contains ~1.4 kb of the Cephalosporium genomic DNA located downstream of the translation termination site for the DACS/DAOCS coding sequence. To reduce the amount of this downstream DNA, all but ~120 bp of this DNA was eliminated by utilizing an XbaI restriction site located downstream of the translation stop codon located at the end of the DACS/DAOCS coding sequence.

About 10 µg of plasmid pIT503 (Example 1) are digested with XbaI restriction enzyme in 50 µl of 1×SstI buffer containing ~10 units of XbaI restriction enzyme at 37° C. for 2 hours. The 4 bp, 5' extension left by XbaI cleavage is filled in by the action of Klenow enzyme, the large fragment of DNA polymerase. The DNA is then digested with 10 units of SstI in 50 µl of 1×SstI buffer at 37° C. for 2 hours. The ~1.12 kb SstI-XbaI (filled-in) fragment is then conventionally purified on an acrylamide gel.

About 10 µg of plasmid p1104 (Example 2J) are suspended in 50 µl of 1×SstI buffer with about 10 units each of SstI and BamHI restriction enzyme, and the mixture is incubated for 2 hours at 37° C. The BamHI 5' extensions are filled-in with Klenow enzyme.

Figure 14:
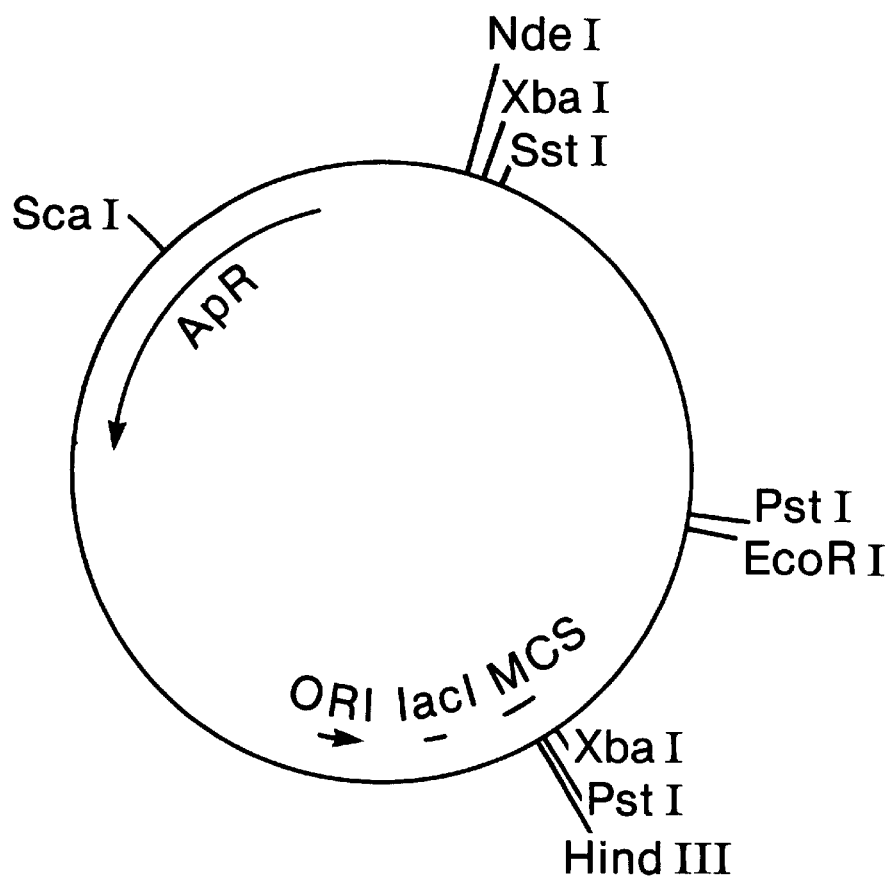
FIG. 14. Restriction site and function map of plasmid p1105.

About 100 nanograms of the XbaI(filled-in)-SstI fragment of plasmid pIT503 are mixed with 100 nanograms of BamHI (filled in)-SstI-digested plasmid p1104, and the mixture is ligated and then transformed into *E. coli* K12 JM109. The desired construction, designated plasmid p1105 (FIG. 14) is isolated from the transformants and identified by restriction enzyme analysis. Plasmid p1105 is especially useful, because the fusion of filled-in XbaI and BamHI ends, as is achieved during the construction of plasmid p1105, reconstructs the BamHI site (although the XbaI site is destroyed).

illustrative example is the removal of 30 base pairs, encoding 10 amino acids, from the coding sequence for the amino terminus of DACS/DAOCS.

About 10 µg of plasmid p1105 are dissolved in 50 µl of 1×SstI buffer containing ~10 units each of SstI and XbaI enzyme. The mixture is incubated at 37° C. for 2 hours. The SstI-XbaI-digested plasmid p1105 DNA was treated with T4 polymerase to remove the 3' overhangs from the SstI cleavage and to fill in the 5' extension from the XbaI cleavage. The XbaI-SstI-digested DNA was precipitated, centrifuged, and the DNA pellet resuspended in 5 µl of water. About 1 µl of 10×T4 polymerase buffer (666.6 mM potassium acetate; 330 mM Tris.acetate, pH=7.8; and 100 mM MgOAc), 1 µl of 5 mM dithiothreitol, 1 µl of 1 mg/ml bovine serum albumin (DNA grade, BRL), and 2 µl of a solution 75 mM in each of the four deoxynucleotides were added to the solution of DNA. The mixture is allowed to warm to 37° C. with a short (about 2 minutes) incubation. Then, ~5 units of T4 polymerase are added to the solution, and the mixture is incubated a further 10 minutes at 37° C.

Figure 16:
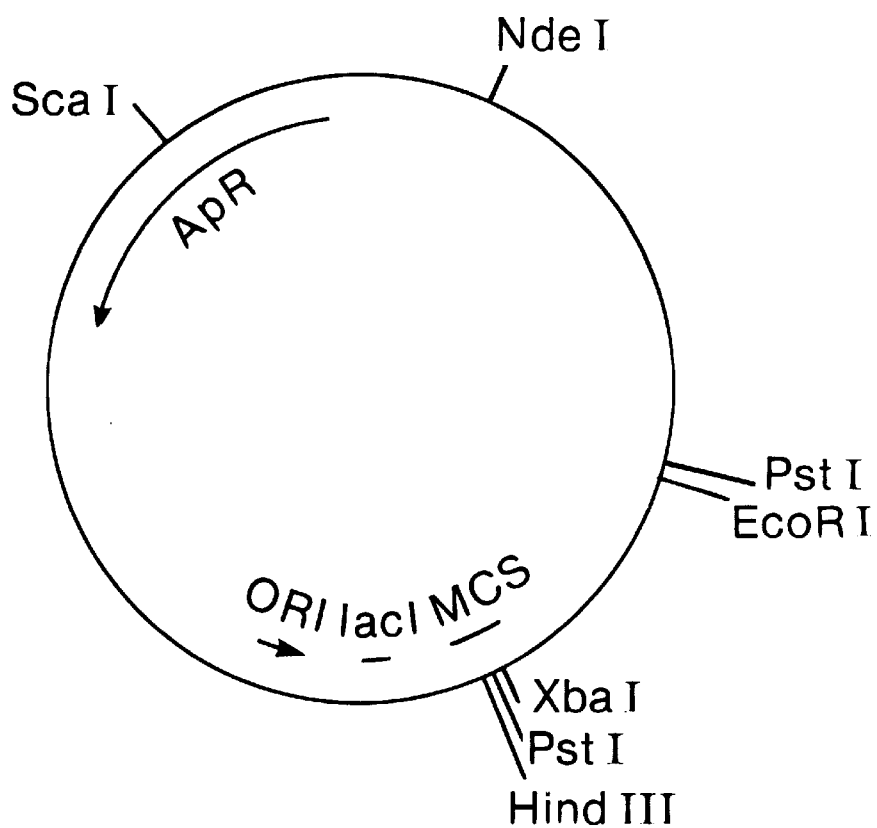
FIG. 16. Restriction site and function map of plasmid p1106.

The DNA was then self-ligated and used to transform *E. coli* K12 JM109. The desired *E. coli* K12 JM109/p1106 transformants are identified by restriction enzyme analysis of their plasmid DNA. A restriction site and function map of plasmid p1106 is presented in FIG. 16 of the accompanying drawings. The expandase/hydroxylase (DACS/DAOCS) gene product encoded by the coding sequence on plasmid p1106 lacks amino acid residues 11 through 20, inclusive, as compared to the wild type, and amino acid residue 11 of the mutant is a glutamic acid residue, whereas corresponding amino acid residue 21 of the wild type is an aspartic acid residue. Otherwise, the DACS/DAOCS coding sequences on plasmids p1105 and p1106 are identical.

Figure 17:
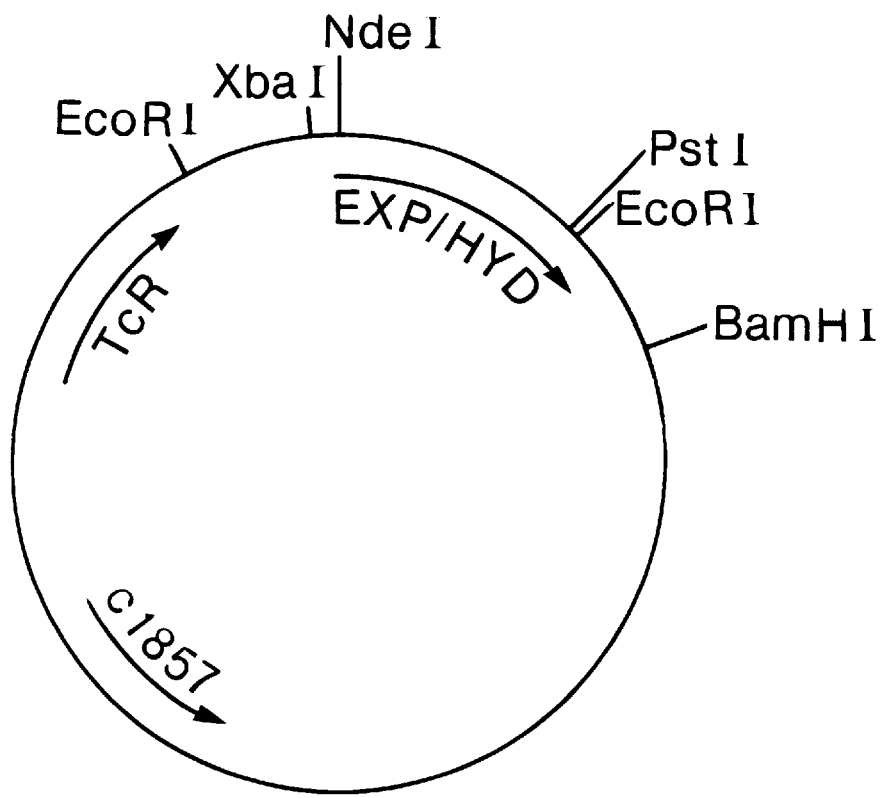
FIG. 17. Restriction site and function map of plasmid pIT512.

The ~1.1 kb NdeI-BamHI fragment of p1106 is cloned into the large NdeI-BamHI restriction fragment of plasmid pCZR336 to yield plasmid pIT512 (FIG. 17). Plasmid pIT512 drives expression of a mutant form of DACS/DAOCS in *E. coli* host cells.

EXAMPLE 6
Construction of Plasmid pIT513

Besides insertion and deletion mutations, the amino acid composition and sequence of the DACS/DAOCS gene product can be altered by base pair changes in the protein coding region. One way of accomplishing this is to use site-directed mutagenesis, as outlined below. This example describes the replacement of a cysteine residue (residue 100 in the wild-type DACS/DAOCS coding sequence) with a serine residue.

The general method for site directed mutagenesis is described in Example 2F. The gene of interest is first cloned into an m13 phage to provide a convenient source of single-stranded DNA. About 5 μg of M13mp18 DNA (New England Biolabs) are incubated in 50 μl of 1×SstI buffer containing ~10 units of BamHI enzyme for 2 hours at 37° C.

About 50 μg of plasmid pIT511 (Example 4) are incubated in 250 μl of 1×SstI buffer containing 50 units each of BamHI and BglII enzyme for 2 hours at 37° C. The BglII site is in the 5' noncoding region upstream of the translation start codon of the DACS/DAOCS coding sequence on expression vector pIT511, and the BamHI site is about 100 bp downstream of the translation stop codon. The ~1.1 kb BamHI-BglII fragment of plasmid pIT511 is conventionally purified from acrylamide.

About 100 nanograms of the BamHI-digested phage M13mp18 DNA are added to 100 nanograms of the purified BamHI-BglII fragment of plasmid pIT511. The mixture is ligated and transformed into *E. coli* K12 JM109. The plasmid resulting from the desired insertion has the fragment oriented so that the 5' end of the DACS/DAOCS coding sequence (the BglII site) is nearest the lacZ gene fragment and the 3' end of the coding sequence (the BamHI site) is nearest the lacI gene on the M13 vector. The proper isolate is designated mIT113.

The mutagenic primer used for this experiment is synthesized and has the sequence:

5'-TCGGACTACTCGACGAGCTACTCCATGGGCATC-3'

The desired derivative of mIT113 containing the above sequence instead of the wild type sequence is identified and characterized as described in Example 2F and is designated mIT114. Identification of the desired isolate is aided by the creation of a new AluI restriction site in the properly mutagenized gene.

About 10 μg of phage mIT114 DNA are dissolved in 50 μl of 1×high-salt buffer containing about 10 units each of BamHI and NdeI enzyme, and the mixture is incubated at 37° C. for 2 hours. The ~1.1 kb NdeI-BamHI fragment is isolated from an acrylamide gel using conventional procedures, mixed with NdeI-BamHI-cleaved plasmid pCZR336, ligated, and transformed into *E. coli* K12 JM109. The desired *E. coli* K12 JM109/pIT513 transformant is identified by restriction enzyme analysis of its plasmid DNA. Plasmid pIT513 drives expression of a mutant derivative of DACS/DAOCS, which has a serine residue replacing the cysteine residue at position 100 in the wild-type sequence. *E. coli* K12 JM109/pIT513 is a preferred source of this mutant protein.

EXAMPLE 7
Construction of Plasmids pPS56 and pPS55

Plasmid pPS56 is a *Cephalosporium acremonium* expression vector that confers hygromycin B resistance and contains the *C. acremonium* DACS/DAOCS gene. Plasmid pPS56 was constructed using plasmid pMLC12 (NRRL B-18097), plasmid pIT503 (Example 1A), and plasmid pPS34. Plasmid pPS34 is disclosed in U.S. patent application Ser. No. 895,008, filed Aug. 8, 1986, incorporated herein by reference.

A. Construction of Intermediate Plasmid pPS55

About 5 μg of plasmid pMLC12 (FIG. 19 and NRRL B-18097) were dissolved in 5 μl of 10×HindIII buffer and 40 μl of water. About 5 μl (~50 units) of restriction enzyme HindIII were added to the solution of DNA, and the resulting reaction was incubated at 37° C. for two hours. The reaction was terminated by extraction with buffered phenol, which was followed by extraction with chloroform. The HindIII-digested pMLC12 plasmid DNA was precipitated by adjusting the NaCl concentration to 0.25 M, adding two volumes of cold ethanol, and chilling at −70° C. for 10 minutes. The HindIII-digested pMLC12 plasmid DNA was collected by centrifugation and resuspended in 5 μl of water.

The ~2.3 kb HindIII restriction fragment of plasmid pPS34 contains the *Cephalosporium acremonium* isopenicillin N synthetase promoter attached to the coding sequence of a hygromycin B phosphotransferase gene, which confers resistance to hygromycin B, from *Escherichia coli*. About 10 μg of plasmid pPS34 (FIG. 20) were digested with restriction enzyme HindIII at 37° C. for two hours. The reaction mixture was then loaded into a 0.8% agarose gel, and the desired ~2.3 kb HindIII restriction that comprises the promoter from the *Cephalosporium acremonium* IPS gene attached to and in frame with the hygromycin resistance-conferring coding sequence was isolated. About 1 μg of the desired fragment was recovered and suspended in 5 μl of water.

One μl of the HindIII-digested plasmid pMLC12 DNA was added to 4 μl of the ~2.3 kb HindIII restriction fragment of plasmid pPS34, together with 2 μl 10×of ligase buffer, 2 μl of T4 DNA ligase, and 11 μl of water. The resulting ligation reaction was incubated at 15° C. overnight. The ligated DNA constituted the desired plasmid pPS55 and other related ligation products.

This ligation mixture was used to transform *E. coli* K12 JM109 (Pharmacia P-L Biochemicals). The cells were grown to an O.D.$_{590}$ of ~0.5 absorbance units. The culture was chilled on ice for ten minutes, and the cells were collected by centrifugation. The cell pellet was resuspended in 25 ml of cold, 100 mM CaCl$_2$ and then incubated on ice for 25 minutes. The cells were once again pelleted by centrifugation, and the pellet was resuspended in 2.5 ml of cold 100 mM CaCl$_2$ and incubated on ice overnight.

Two hundred μl of this cell suspension were mixed with the ligated DNA prepared above and incubated on ice for 20 minutes. At the end of this period, the cells were placed in a water bath at 42° C. for 2 minutes and then returned to the ice for an additional 10 minutes. The cells were collected by centrifugation and resuspended in one ml of L broth and incubated at 37° C. for 2 hours.

Aliquots of the cell mixture were plated on L-agar plates containing 25 μg/ml of chloramphenicol, 40 μg/ml of X-gal, and 40 μg/ml of IPTG. The plates were incubated at 37° C. overnight. Colonies that contain a plasmid without an insert, such as *E. coli* K12 JM109/pMLC12, appear blue on these plates. Colonies that contain a plasmid with an insert, such as *E. coli* K12 JM109/pPS55, are white on these plates. Several white colonies were selected and screened by restriction analysis of their plasmid DNA for the presence of the ~2.3 kb HindIII restriction fragment containing the *Cephalosporium acremonium* IPS promoter attached to the hygromycin resistance-conferring coding sequence. A large scale preparation of plasmid pPS55 (FIG. 25) was made in substantial accordance with the teaching in Example 1. Plasmids containing the ~2.3 kb HindIII fragment in the reverse orientation from that in pPS55 would function equally as well as pPS55 and are within the scope of this invention.

B. Final Construction of Plasmid pPS56

The ~7.0 kb BamHI restriction fragment of plasmid pIT503 contains the *Cephalosporium acremonium* DACS/DAOCS gene. About 20 µg of plasmid pIT503 (Example 1) were dissolved in 5 µl of 10×BamHI buffer and 40 µl of water. About 5 µl (~50 units) of restriction enzyme BamHI were added to the solution of DNA, and the resulting reaction was incubated at 37° C. for two hours. The reaction mixture was then loaded into a 0.8% preparative agarose gel, and the desired ~7.0 kb BamHI restriction fragment that comprises the DACS/DAOCS gene was isolated. About 3 µg of the desired fragment were recovered and suspended in 5 µl of water.

About 15 µg of plasmid pPS55 (Example 7A) were dissolved in 5 µl of 10×BamHI buffer and 40 µl of water. About 5 µl (approximately 50 units) of restriction enzyme BamHI were added to the solution of DNA, and the resulting reaction was incubated at 37° C. for 3 minutes. The reaction was terminated by extraction with buffered phenol, which was followed by extraction with chloroform. The partially BamHI-digested plasmid pPS55 DNA was loaded into a 0.8% agarose preparative gel, and the desired ~5.0 kb linearized form was isolated. About 3 µg of the BamHI-linearized plasmid pPS55 DNA was recovered. The linearized molecules represented approximately equal amounts of the two possible linear forms of plasmid pPS55 resulting from partial digestion with BamHI. The undesired molecule is the linear form produced by cleavage at the BamHI site within the hygromycin B phosphotransferase (HmR) gene. The desired molecule was formed by BamHI cleavage between the CAT and HmR genes of plasmid pPS55.

One µl of the BamHI-digested plasmid pPS55 DNA was added to about 4 µl of the ~7.0 kb BamHI restriction fragment of plasmid pIT503, together with 2 µl of 10×ligase buffer, 2 µl of T4 DNA ligase, and 11 µl of water. The resulting ligation reaction was incubated at 15° C. overnight. The ligated DNA constituted the desired plasmid pPS56 and other related ligation products.

This ligation mixture was used to transform *E. coli* K12 C600 (ATCC 33524). Aliquots of the transformed cell mixture were plated on L-agar plates containing 25 µg/ml chloramphenicol. The plates were incubated at 37° C. overnight. Colonies that contained a plasmid without an insert, such as *E. coli* K12 C600/pPS55, were distinguished from colonies that contained a plasmid with an insert, such as *E. coli* K12 C600/pPS56, in substantial accordance with the method of Eckardt (Eckardt, T., 1978, A rapid method for the identification of plasmid DNA in bacteria. Plasmid 1:584–588). Several plasmids were identified that contained inserts and were further screened by restriction analysis for the presence of the ~7.0 kb BamHI restriction fragment containing the *Cephalosporium acremonium* DACS/DAOCS gene inserted into the appropriate BamHI site to yield plasmid pPS56. A large scale preparation of plasmid pPS56 (FIG. 26) was made in substantial accordance with the teaching in Example 1. Plasmids containing the ~7.0 kb BamHI fragment in the reverse orientation from that in pPS56 would function equally as well as pPS56 and are within the scope of this invention. In addition, the HmR gene-containing fragment may be derived from plasmids that have the fragment in the opposite orientation from that of pPS55.

EXAMPLE 8

Construction of Plasmid pPS51

About 15 µg of plasmid pMLC12 DNA (NRRL B-18097) were dissolved in 5 µl of 10×EcoRI buffer and 40 µl of water. About 5 µl (~50 units) of restriction enzyme EcoRI were added to the solution of DNA, and the resulting reaction was incubated at 37° C. for 3 minutes to produce a partial digestion. The reaction was terminated by extraction with buffered phenol, which was followed by extraction with chloroform. Plasmid pMLC12 contains two EcoRI restriction sites. The desired partial cleavage of the EcoRI site was to occur within the lacZα fragment and not within the CAT gene. This EcoRI digestion produced a mixture of plasmid pMLC12 DNA molecules: uncut; cut at the undesired location; cut at the desired location; and cut at both locations, producing fragments smaller than the full-length ~2.7 kb molecules. The EcoRI-digested plasmid pMLC12 DNA was precipitated, collected by centrifugation, dissolved in 50 µl of TE buffer, and loaded onto a 0.8% preparative agarose gel. The full length linear molecules (i.e., ~2.7 kb) were isolated.

The partially EcoRI-digested plasmid pMLC12 DNA was dissolved in 5 µl of 10×SalI buffer and 40 µl of water. About 5 µl (~50 units) of restriction enzyme SalI were added to the EcoRI-linearized plasmid pMLC12 DNA, and the resulting reaction was incubated at 37° C. for two hours. The unique SalI restriction site in plasmid pMLC12 is located 24 base pairs from the EcoRI site within the lacZα fragment of plasmid pMLC12. Thus, complete SalI digestion of the partially EcoRI-digested plasmid pMLC12 DNA produced four DNA fragments: one ~2.7 kb, the desired molecule; one ~24 bp in length; one ~0.6 kb; and one ~1.9 kb. The DNA molecules were size-fractionated on a 0.8% agarose gel. The nearly full-length, ~2.7 kb linear molecules were isolated.

Figure 18:
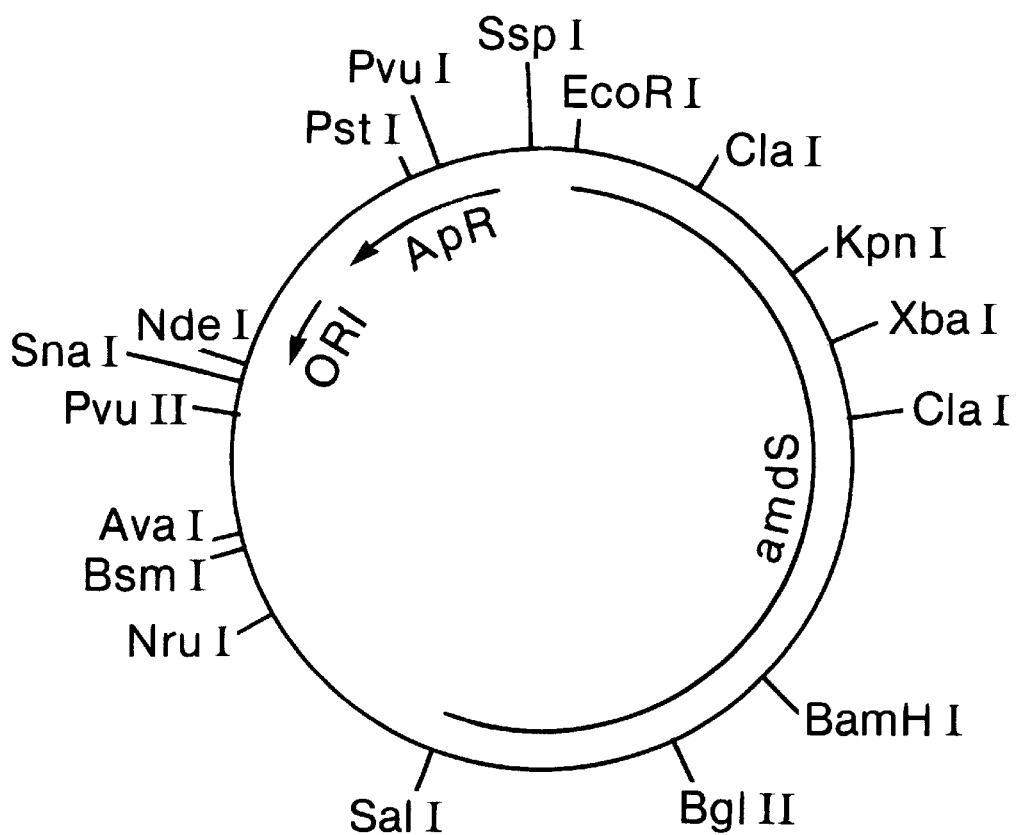
FIG. 18. Restriction site and function map of plasmid p3SR2.

The acetamidase gene of *Aspergillus nidulans* can be isolated on an ~5.0 kb EcoRI-SalI restriction fragment of plasmid p3SR2. About 10 µg of plasmid p3SR2 (FIG. 18 and NRRL B-18182) were dissolved in 5 µl of 10×EcoRI buffer and 40 µl of water. About 5 µl (~50 units) of restriction enzyme EcoRI were added to the solution of DNA, and the resulting reaction was incubated at 37° C. for two hours. The reaction was terminated by extraction with buffered phenol, which was followed by extraction with chloroform. The EcoRI-digested p3SR2 plasmid DNA was precipitated, collected by centrifugation, and resuspended in 5 µl of 10×SalI buffer and 40 µl of water. About 5 µl (~50 units) of restriction enzyme SalI were added to the solution of DNA, and the resulting reaction was incubated at 37° C. for two hours. The two DNA fragments generated in these digestions were size-fractionated on a 0.8% preparative agarose gel. One ~4.3 kb fragment comprised pBR322 DNA and the other ~5.0 kb fragment comprised the acetamidase (amdS) gene from *Aspergillus nidulans*. The ~5.0 kb EcoRI-SalI fragment was isolated. About 3 µg of the ~5.0 kb EcoRI-SalI fragment were recovered and suspended in 5 µl of water.

One µl of the EcoRI-SalI-digested plasmid pMLC12 DNA was added to about 4 µl of the ~5.0 kb EcoRI-SalI restriction fragment of plasmid p3SR2, together with 2 µl of 10×ligase buffer, 2 µl of T4 DNA ligase, and 11 µl of water. The resulting ligation reaction was incubated at 15° C. overnight. The ligated DNA constituted the desired plasmid pPS51 and other related ligation products.

This ligation mixture was used to transform *E. coli* K12 C600 (ATCC 33524). Aliquots of the transformed cell mixture were plated on L-agar plates containing 25 µg/ml of chloramphenicol. The plates were incubated at 37° C. overnight. Colonies that contained a plasmid without an insert, such as *E. coli* K12 C600/pMLC12 were distinguished from colonies that contained a plasmid with an insert, such as *E. coli* K12 C600/pPS51, in substantial accordance with the method of Eckardt. A colony was identified that contained a plasmid with an insert. Plasmid DNA from this colony was screened by restriction analysis for the presence of the ~5.0 kb EcoRI-SalI restriction fragment containing the *Aspergillus nidulans* amdS gene and had the correct structure for the desired plasmid pPS51. A large scale plasmid preparation of plasmid pPS51 was made in substantial accordance with the teaching in Example 1. A restriction site and function map of plasmid pPS51 is presented in FIG. 21 of the accompanying drawings.

EXAMPLE 9
Construction of plasmid pPS52

About 5 µg of plasmid pPS51 DNA (Example 8) were dissolved in 5 µl of 10×HindIII buffer and 40 µl of water. About 5 µl (~50 units) of restriction enzyme HindIII were added to the solution of DNA, and the resulting reaction was incubated at 37° C. for two hours. The reaction was terminated by extraction with buffered phenol, which was followed by extraction with chloroform. The HindIII-digested plasmid pPS51 DNA was precipitated, collected by centrifugation, and resuspended in 5 µl of water.

The single-strands of the following linker were synthesized using an automated DNA synthesizer:

About 75 picomoles of each single strand of the linker were individually dissolved in 22.5 µl of water and 2.5 µl of ligase buffer. About 1 µl (10 units) of T4 DNA kinase (BRL) was added to each solution of single-stranded DNA molecules, and the reactions were incubated at 37° C. for 30 minutes. Following the kinase reaction, the reaction mixtures were incubated at 70° C. for 15 minutes to inactivate the kinase. Then, to anneal the single-stranded DNA molecules to form the linker, the two reaction mixtures were pooled, incubated at 65° C. for 10 minutes, incubated at room temperature for approximately 2 hours, and then incubated at 4° C. overnight.

One µl of the HindIII-digested plasmid pPS51 DNA was added to 4 µl of the ~7.0 kb BamHI restriction fragment of plasmid pIT503 (Example 7B) and 10 µl of the annealed linker. About 4 µl of 10×ligase buffer, 2 µl of T4 DNA ligase, and 29 µl of water were added to the mixture of DNA, and the resulting reaction was incubated at 4° C. overnight. The ligated DNA constituted the desired plasmid pPS52.

The ligated DNA was used to transform *E. coli* K12 C600 (ATCC 33524). Aliquots of the transformed cell mixture were plated on L-agar plates containing 25 µg chloramphenicol. The plates were incubated at 37° C. overnight. Colonies that contained a plasmid without an insert, such as *E. coli* K12 C600/pPS51, were distinguished from colonies that contained a plasmid with an insert, such as *E. coli* K12 C600/pPS52, in substantial accordance with the method of Eckardt. Several colonies were identified that had been transformed by plasmids containing inserts. Those colonies with inserts in their plasmid DNA were screened by restriction analysis of their plasmid DNA for the presence of the ~7.0 kb BamHI restriction fragment containing the *Cephalosporium acremonium* DACS/DAOCS gene inserted into the HindIII site located between the CAT and amdS genes of plasmid pPS51. A large scale preparation of plasmid pPS52 was made in substantial accordance with the teaching in Example 1. A restriction site and function map of plasmid pPS52 is presented in FIG. 22 of the accompanying drawings. Plasmids containing the ~7.0 kb BamHI fragment in the reverse orientation from that in pPS52 would function equally as well as pPS52 and are within the scope of this invention.

EXAMPLE 10
Construction of Plasmid pPS53

About 5 µg of pMLC12 plasmid DNA (NRRL B-18097) were dissolved in 5 µl of 10×BamHI buffer and 40 µl of water. About 5 µl (~50 units) of restriction enzyme BamHI were added to the solution of DNA, and the resulting reaction was incubated at 37° C. for two hours. The reaction was terminated by extraction with buffered phenol, which was followed by extraction with chloroform. The BamHI-digested plasmid pMLC12 DNA was precipitated, collected by centrifugation, and resuspended in 5 µl of water.

The promoter of the *Penicillium chrysogenum* isopenicillin N synthetase gene can be isolated on an ~1.0 kb NcoI restriction fragment of plasmid pLC1. About 10 µg of plasmid pLC1 (NRRL B-18181) were dissolved in 5 µl of 10×NcoI buffer (1.5 M NaCl; 60 mM Tris-HCl, pH=7.9; 60 mM MgCl$_2$; and 1 mg/ml BSA) and 40 µl of water. About 5 µl (~50 units) of restriction enzyme NcoI were added to the solution of DNA, and the resulting reaction was incubated at 37° C. for two hours. The reaction mixture was then loaded onto a 0.8% agarose gel, and the desired ~1.0 kb NcoI restriction fragment that comprises the promoter from the *Penicillium chrysogenum* IPS gene was isolated. About 2 µg of the desired fragment were recovered and dissolved in 5 µl of water.

The single-strands of the following linker were synthesized using an automated DNA synthesizer:

Each single strand of the linker was treated with T4 DNA kinase and then annealed to form the intact linker.

One µl of the BamHI-digested plasmid pMLC12 DNA was added to 4 µl of the ~1.0 kb NcoI restriction fragment of plasmid pLC1 and 10 µl of the annealed linker described above. About 4 µl of 10×ligase buffer, 2 µl of T4 DNA ligase, and 29 µl of water were added to the mixture of DNA, and the resulting reaction was incubated at 4° C. overnight. The ligated DNA constituted the desired plasmid pPS53.

The ligated DNA was used to transform *E. coli* K12 JM109. Aliquots of the transformed cell mixture were plated on L-agar plates containing 25 µg/ml chloramphenicol, 40 µg/ml X-gal, and 40 µg/ml IPTG. The plates were incubated at 37° C. overnight. Colonies that contain a plasmid without an insert, such as *E. coli* K12 JM109/pMLC12, appear blue on these plates. Colonies that contain a plasmid with an insert, such as *E. coli* K12 JM109/pPS53, are white on these plates. Several white colonies were selected and screened by restriction analysis of their plasmid DNA for the presence of the ~1.0 kb restriction fragment containing the promoter of the *Penicillium chrysogenum* isopenicillin N synthetase gene now bounded by BamHI restriction sites. A large scale preparation of plasmid pPS53 was made in substantial accordance with the teaching in Example 1. A restriction site and function map of plasmid pPS53 is presented in FIG. 23 of the accompanying drawings. Plasmids containing the ~1.0 kb NcoI fragment with the flanking BamHI linkers in the reverse orientation from that of pPS53 function equally as well as pPS53 and are within the scope of this invention.

EXAMPLE 11
Construction of Plasmid pPS54

The *Penicillium chrysogenum* isopenicillin N synthetase gene can be isolated on an ~3.3 kb HindIII restriction fragment from plasmid pLC2. About 10 μg of plasmid pLC2 (ATCC 53334) were dissolved in 5 μl of 10×HindIII buffer and 40 μl of water. About 5 μl (~50 units) of restriction enzyme HindIII were added to the solution of DNA, and the resulting reaction was incubated at 37° C. for two hours. The reaction mixture was then loaded into a 0.8% agarose gel, and the desired ~3.3 kb HindIII restriction fragment that comprises the IPS gene from *P. chrysogenum* was isolated. About 1 μg of the desired fragment was recovered and suspended in 5 μl of water.

One μl of HindIII-digested plasmid pPS51 DNA (Example 9) was added to 4 μl of the ~3.3 kb HindIII restriction fragment of plasmid pLC2, together with 2 μl of 10×ligase buffer, 2 μl of T4 DNA ligase, and 11 μl of water. The resulting ligation reaction was incubated at 15° C. overnight. The ligated DNA constituted the desired plasmid pPS54 and other related ligation products.

The ligation mixture was used to transform *E. coli* K12 C600 (ATCC 33524). Aliquots of the transformed cell mixture were plated on L-agar plates containing 25 μg/ml of chloramphenicol. The plates were incubated at 37° C. overnight. Colonies that contained a plasmid without an insert, such as *E. coli* K12 C600/pPS51, were distinguished from those that did contain an insert, such as *E. coli* K12 C600/pPS54, in substantial accordance with the method of Eckardt. Several colonies were identified that contained plasmids with inserts. Those plasmids with inserts were screened by restriction enzyme analysis for the presence of the ~3.3 kb HindIII fragment of plasmid pLC2. A large scale preparation of plasmid pPS54 was made in substantial accordance with the teaching in Example 1. A restriction site and function map of plasmid pPS54 is presented in FIG. 24 of the accompanying drawings. Plasmids containing the ~3.3 kb HindIII fragment in the reverse orientation from that in pPS54 function equally as well as pPS54 and are within the scope of this invention.

EXAMPLE 12
Construction of Plasmid pPS57

About 10 μg of plasmid pPS55 were dissolved in 5 μl of 10×BamHI buffer and 40 μl of water. About 5 μl (~50 units) of restriction enzyme BamHI were added to the solution of DNA, and the resulting reaction was incubated at 37° C. for two hours. The reaction mixture was then loaded into a 0.8% agarose gel, and the desired ~4.3 kb BamHI restriction fragment that comprises the coding sequence of the HmR gene was isolated. About 1 μg of the desired fragment was recovered and suspended in 5 μl of water.

The ~1.0 kb BamHI fragment from plasmid pPS53 contains the promoter of the *Penicillium chrysogenum* isopenicillin N synthetase gene was isolated by dissolving 10 μg of plasmid pPS53 in 5 μl of 10×BamHI buffer and 40 μl of water. About 5 μl (~50 units) of restriction enzyme BamHI were added to the solution of DNA, and the resulting reaction was incubated at 37° C. for two hours. The reaction mixture was then loaded into a 0.8% agarose gel, and the desired ~1.0 kb BamHI restriction fragment was isolated. About 1 μg of the desired fragment was recovered and suspended in 5 μl of water.

One μl of the ~4.3 kb BamHI fragment of plasmid pPS55 was added to about 4 μl of the ~1.0 kb BamHI restriction fragment of plasmid pPS53, together with 2 μl of 10×ligase buffer, 2 μl of T4 DNA ligase, and 11 μl of water. The resulting ligation reaction was incubated at 15° C. overnight. The ligated DNA constituted the desired plasmid pPS57 and other related ligation products.

This ligation mixture was used to transform *E. coli* K12 C600 (ATCC 33524). Aliquots of the transformed cell mixture were plated on L-agar plates containing 25 μg/ml of chloramphenicol. The plates were incubated at 37° C. overnight. Colonies that contained a plasmid without an insert were distinguished from colonies that contained plasmid pPS57 in substantial accordance with the method of Eckardt. Several colonies were identified that contained plasmids with inserts. These plasmids were screened by restriction analysis for the presence of the ~1.0 kb BamHI restriction fragment comprising the promoter of the *Penicillium chrysogenum* IPS gene positioned to drive expression of HmR. A large scale preparation of plasmid pPS57 was made in substantial accordance with the teaching in Example 1. A restriction site and function map of plasmid pPS57 is presented in FIG. 27 of the accompanying drawings.

EXAMPLE 13
Construction of Plasmid pPS60

About 5 μg of plasmid pIT511 (Example 4) were dissolved in 5 μl of 10×BglII buffer (1.0 M NaCl; 100 mM Tris-HCl, pH=7.4; 100 mM MgCl$_2$; 100 mM 2-mercaptoethanol; and 1 mg/ml BSA) and 40 μl of water. About 5 μl (~50 units) of restriction enzyme BglII were added to the solution of DNA, and the resulting reaction was incubated at 37° C. for two hours. The reaction was terminated by extraction with buffered phenol, which was followed by extraction with chloroform. The BglII-digested plasmid pIT511 DNA was precipitated, collected by centrifugation, and resuspended in 5 μl of water.

One μl of the BglII-digested plasmid pIT511 DNA was added to about 4 μl of the ~1.0 kb BamHI restriction fragment of plasmid pPS53 (Example 10), together with 2 μl of 10×ligase buffer, 2 μl of T4 DNA ligase, and 11 μl of water. The resulting ligation reaction was incubated at 15° C. overnight. The ligated DNA constituted the desired plasmid pPS60 and other related ligation products.

The ligated DNA was used to transform *E. coli* K12 C600 (ATCC 33524). Aliquots of the transformed cell mixture were plated on L-agar plates containing 15 μg/ml of tetracycline. The plates were incubated at 30° C. overnight. Colonies that contained a plasmid without an insert, such as *E. coli* K12 C600/pIT511, were distinguished from colonies that contained a plasmid with an insert, such as *E. coli* K12 C600/pPS60, in substantial accordance with the method of Eckardt. Several colonies were identified that contained plasmids with inserts. Those plasmids with inserts were screened by restriction analysis for the presence of the restriction fragment containing the promoter of the *Penicillium chrysogenum* IPS gene in the desired orientation as illustrated for pPS60. A large scale preparation of plasmid pPS60 was made in substantial accordance with the teaching in Example 1. A restriction site and function map of plasmid pPS60 is presented in FIG. 30 of the accompanying drawings.

EXAMPLE 14
Construction of Plasmid pPS58

About 5 μg of plasmid pPS60 (Example 13) were dissolved in 5 μl of 10×XbaI buffer (500 mM NaCl; 60 mM Tris-HCl, pH=7.9; 60 mM MgCl$_2$; and 1 mg/ml BSA) and 40 μl of water. About 5 μl (~50 units) of restriction enzyme XbaI were added to the solution of DNA, and the resulting reaction was incubated at 37° C. for two hours. The XbaI-digestion of pPS60 plasmid DNA produced three fragments of DNA; one ~7.9 kb fragment and two smaller fragments (under 300 bp). The digestion reaction was loaded onto a 0.8% preparative agarose gel. The ~7.9 kb fragment was isolated, and about 3 µg were recovered and suspended in 5 µl of water.

Approximately 0.5 µg of the ~7.9 kb XbaI restriction fragment of plasmid pPS60 was dissolved in 10 µl of 10×ligase buffer, 4 µl of T4 DNA ligase, and 86 µl of water. The resulting ligation reaction was incubated at 15° C. overnight. The ligated DNA constituted the desired plasmid pPS58.

The ligated DNA was used to transform *E. coli* K12 C600 (ATCC 33524). Aliquots of the transformed cell mixture were plated on L-agar plates containing 15 µg/ml of tetracycline. The plates were incubated at 30° C. overnight. Several TcR colonies were recovered and their plasmid DNA analyzed by restriction enzyme analysis for the absence of the two small XbaI fragments characteristic of plasmid pPS60. A large scale preparation of plasmid pPS58 was made in substantial accordance with the teaching in Example 1. A restriction site and function map of plasmid pPS58 is presented in FIG. 28 of the accompanying drawings.

EXAMPLE 15
Construction of Plasmid pPS59

About 5 µg of plasmid pPS58 DNA (Example 14) were dissolved in 5 µl of 10×XbaI buffer and 40 µl of water. About 5 µl (~50 units) of restriction enzyme XbaI were added to the solution of DNA, and the resulting reaction was incubated at 37° C. for two hours. The reaction was terminated by extraction with buffered phenol, which was followed by extraction with chloroform. The XbaI-digested plasmid pPS58 DNA was precipitated, collected by centrifugation, and resuspended in 5 µl of water.

The single-strands of the following linker were synthesized using an automated DNA synthesizer:

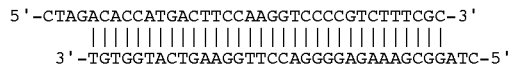

Each single strand of the linker was individually treated with T4 DNA kinase and then annealed to form the intact linker.

One µl of the XbaI-digested plasmid pPS58 DNA was added to 10 µl of the annealed linker. About 4 µl of 10×ligase buffer, 2 µl of T4 DNA ligase, and 29 µl of water were added to the mixture of DNA, and the resulting reaction was incubated at 4° C. overnight. The ligated DNA constituted the desired plasmid pPS59.

Figure 29:
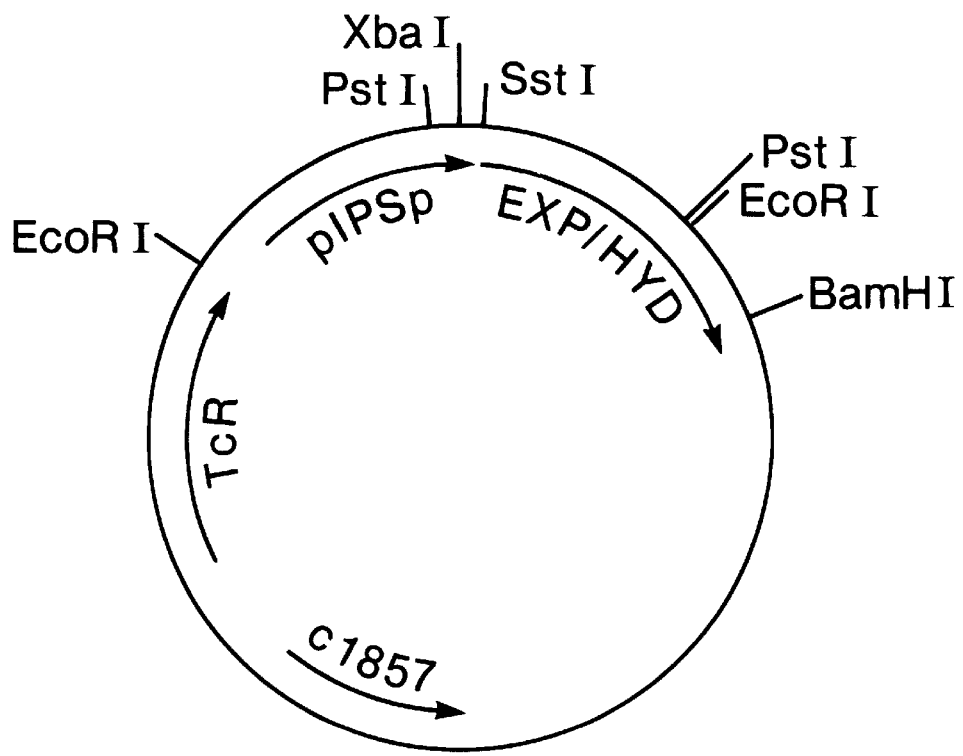
FIG. 29. Restriction site and function map of plasmid pPS59.

This ligated DNA was used to transform *E. coli* K12 C600 (ATCC 33524). Aliquots of the transformed cell mixture were plated on L-agar plates containing 15 µg/ml of tetracycline. The plates were incubated at 37° C. overnight. Colonies that contained a plasmid without an insert, such as *E. coli* K12 C600/pPS58, were distinguished from colonies that contained a plasmid with an insert, such as *E. coli* K12 C600/pPS59, by restriction enzyme analysis of their plasmid DNA for the presence of the linker molecule. A large scale plasmid preparation was made in accordance with the procedure of Example 1 from a transformant containing plasmid pPS59 with the linker present in the desired orientation. A restriction site and function map of plasmid pPS59 is presented in FIG. 29 of the accompanying drawings.

EXAMPLE 16
Construction of Plasmid pPS61

About 5 µg of plasmid pPS51 DNA (Example 8) were dissolved in 25 µl of EcoRI reaction buffer. This reaction mixture was incubated at 37° C. for 2 hours. The reaction was terminated by extraction with buffered phenol, which was followed by extraction with chloroform. The EcoRI-digested DNA was precipitated, collected by centrifugation, and resuspended in 5 µl of water.

The EcoRI-digested DNA was then loaded onto a 1.0% agarose gel. The ~5.6 kb EcoRI fragment containing the amdS gene was isolated from the ethidium bromide-stained gel in substantial accordance with Example 2.

About 5 µg of plasmid pPS59 (Example 15) were dissolved in 5 µl of 10×BamHI buffer and 40 µl of water. About 5 µl (~50 units) of restriction enzyme BamHI were added to the solution of DNA, and the resulting reaction was incubated at 37° C. for two hours. BamHI digestion of plasmid pPS59 DNA produces a single linear ~8.0 kb fragment. The reaction was terminated by extraction with buffered phenol and then with chloroform. The BamHI-digested plasmid pPS59 DNA was precipitated and collected by centrifugation.

One µl of the EcoRI-digested plasmid pPS51 DNA was added to 5 µl of the ~8.0 kb BamHI fragment and 1 µl of a kinased and annealed oligonucleotide linker

```
(5'-GACTCCCGGG-3'
    3'-GGGCCCTTAA-5', available from New England
Biolabs).
```

About 2 µl of 10×ligase buffer, 2 µl of T4 DNA ligase, and 11 µl of water were added to the mixture of DNA, and the resulting reaction was incubated at 15° C. overnight. The ligated DNA constituted the desired plasmid pPS61.

The ligated DNA was used to transform *E. coli* K12 C600 (ATCC 33524). Aliquots of the transformed cell mixture were plated on L-agar plates containing 15 µg/ml of tetracycline. The plates were incubated at 37° C. overnight. Colonies that contained a plasmid without an insert, such as *E. coli* K12 C600/pPS59, were distinguished from colonies that contained a plasmid with an insert, such as *E. coli* K12 C600/pPS61, in substantial accordance with the method of Eckardt. Several colonies were identified that contained plasmids with inserts. These plasmids with inserts were screened by restriction enzyme analysis for the presence of the desired ~5.6 kb EcoRI restriction fragment. A large scale preparation of plasmid pPS61 was made in substantial accordance with the teaching in Example 1. A restriction site and function map of plasmid pPS61 is presented in FIG. 31 of the accompanying drawings. Plasmids containing the fragment ~5.6 kb EcoRI fragment with the attached linkers in the reverse orientation from that in pPS61 function equally as well as pPS61 and are within the scope of this invention.

EXAMPLE 17
Construction of Plasmid pPS62

About 5 µg of plasmid pPS57 (Example 12) were dissolved in 5 µl of 10×HindIII buffer and 40 µl of water. About 5 µl (~50 units) of restriction enzyme HindIII were added to the solution of DNA, and the resulting reaction was incubated at 37° C. for two hours. The reaction mixture was then extracted with buffered phenol and with chloroform. HindIII-digestion of plasmid pPS57 produces a single, linear ~5.3 kb fragment. The HindIII-digested plasmid pPS57 DNA was precipitated and collected by centrifugation.

The HindIII-digested plasmid pPS57 DNA was dissolved in a 25 µl reaction mixture containing Klenow reaction buffer, all four of the dNTPs (dATP, TTP, dGTP, and dCTP), and 2 units of the Klenow fragment of DNA polymerase I. The reaction mixture was incubated at 22° C. for 30 minutes.

The reaction mixture was then extracted with buffered phenol and then with chloroform. The HindIII-digested, Klenow-treated plasmid pPS57 DNA was precipitated, collected by centrifugation, and resuspended in 5 μl of water.

One μl of HindIII-digested, Klenow-treated plasmid pPS57 DNA was added to 5 μl of the ~2.1 kb fragment isolated from pPS59 as described above. About 2 μl of 10×ligase buffer, 2 μl of T4 DNA ligase, and 12 μl of water were added to the mixture of DNA, and the resulting reaction was incubated at 15° C. overnight. The ligated DNA constituted the desired plasmid pPS59.

The ligated DNA was used to transform *E. coli* K12 C600 (ATCC 33524). Aliquots of the transformed cell mixture were plated on L-agar plates containing 25 μg/ml chloramphenicol. The plates were incubated at 37° C. overnight. Colonies that contained a plasmid without an insert, such as *E. coli* K12 C600/pPS57, were distinguished from colonies that contained a plasmid with an insert, such as *E. coli* K12 C600/pPS62, in substantial accordance with the method of Eckardt. Several colonies were identified that contained plasmids with inserts. These plasmids with inserts were screened by restriction analysis for the presence of the restriction fragment containing the desired ~2.1 kb insert. A large scale preparation of plasmid pPS62 was made in substantial accordance with the teaching in Example 1. A restriction site and function map of plasmid pPS62 is presented in FIG. 32 of the accompanying drawings. Plasmids containing the ~2.1 kb NruI fragment in the reverse orientation from that in pPS62 function equally as well as pPS62 and are within the scope of this invention.

EXAMPLE 18
Genetic Transformation of *Penicillium chrysogenum* with Plasmids p3SR2, pPS52 and pPS54

A. *Penicillium chrysogenum* Strains

The preferred Penicillium strain for transformation is obtained from the American Type Culture Collection, Rockville, Md. 20852, under the accession number ATCC 9480. Other *Penicillium chrysogenum* strains or any commercial strains derived from ATCC 9480 by mutation, selection, or genetic breeding for the purpose of improved production of penicillin G or penicillin V are also suitable for use in preparing transformants with the vectors and plasmids of the present invention.

B. Preparation of Uniform Inoculum for Cell Culture

To transform *Penicillium chrysogenum* cells efficiently, it is necessary to remove the cell walls to form stable protoplasts. In the preparation of such protoplasts it is advantageous to begin with a uniform inoculum. Otherwise, preparation of cells in culture is not reproducible and time is lost by attempts to prepare *P. chrysogenum* protoplasts from unsuitable or inadequate amounts of cells.

An ampoule of vegetative cells (~109 colony forming units in 1.0 ml of preservation menstrum: 5% lactose, 10% glycerol, and 0.1% Tween 80), either lyophilized or taken from liquid nitrogen storage and thawed at room temperature, are diluted in 1.0 ml of sterile saline. About 0.1 ml of this suspension is used to inoculate each of approximately 10 slants of sporulation medium: Lactose, 15.0 g/L; corn steep liquor, 2.5 g/L; peptone, 5.0 g/L; NaCl, 4.0 g/L; $MgSO_4 \cdot 7H_2O$, 0.5 g/L; $KH_2PO_4$, 0.6 g/L; $FeCl_3 \cdot 6H_2O$, 0.005 g/L; $CuSO_4 \cdot 5H_2O$, 0.002 g/L; adjust to pH=7.0; agar, 30.0 g/L; and autoclave 20 minutes at 120 psi.

Each slant [15 cm×2.5 cm] contains 25 ml of solidified medium. Inoculum, spread evenly over the surface of the agar slant, is allowed to grow at 25° C. until a confluent lawn of mycelium is present and sporulated (1 week for most strains). The growth from 1 slant is suspended in 10 ml of sterile aqueous culture medium, and the suspension is transferred to 106 ml of aqueous culture medium. The flask containing the suspended cells is placed on a gyrotory shaker and incubated at 25° C. for 18 hours at 285 rpm with a 1 inch throw.

Aqueous culture medium was prepared as follows: 100 ml of solution A (Sucrose, 36 g/L; L-asparagine, 7.5 g/L; $KH_2PO_4$, 15 g/L; $K_2HPO_4$, 21 g/L; $NaSO_4$, 0.75 g/L, $MgSO_4 \cdot 7H_2O$, 0.18 g/L; $CaCl_2$, 0.06 g/L; salts solution, 1 ml/L; and natural pH) are dispensed into a 500 ml shake flask; the flask is covered with a commercial closure and autoclaved at 121° C. for 20 minutes. Two ml of solution B (Glucose, 108 g/L) and 4 ml of solution C (Sucrose, 25 g/L; corn steep liquor (4% w/v nitrogen), 12.5 ml; ammonium acetate, 5.5 g/L; $CaCO_3$, 5 g/L; pH adjusted to 6.5 with KOH; and autoclaved at 121° C. for 20 minutes) are then added to solution A to prepare the aqueous culture medium.

C. Preparation of Penicillium protoplasts

Cells from a 24 hour culture are harvested by suction filtration (Whatman #1 paper in a Buchner funnel) and suspended in buffer (0.01 M Tris(hydroxy-methyl) aminomethane hydrochloride; 0.01 M $MgSO_4$; 0.01 M dithiothreitol; 1.00 M KCl; and pH=7.0 with HCl). Sufficient buffer is added to obtain a final cell concentration of 1 g of cell mass per 50 ml of buffer. The cell suspension is placed on a gyrotory water bath shaker in a 250 ml shake flask and incubated at 29–30° C. for 10 minutes at 140 rpm with a 1 inch throw. Dithiothreitol-treated cells are collected by centrifugation and then resuspended in 50 ml of enzyme solution (10 mg/ml Novozym, Novo Industri A/B Bagsvaerd, Denmark; 0.01 M Tris(hydroxymethyl)aminomethane hydrochloride; 0.01 M $MgSO_4$; 0.01 M dithiothreitol; 1.00 M KCl; and pH=5.8 with HCl) in a 250 ml shake flask. This cell suspension is placed on a gyrotory water-bath shaker and incubated at 29–30° C. for 15 minutes at 140 rpm with a 1 inch throw. Enzyme-treated cells are centrifuged at 1240×g for 6 min, and the resulting pellet is resuspended in buffer (0.01 M Tris(hydroxymethyl)aminomethane hydrochloride; 0.01 M $MgSO_4$; 1.00 M KCl; and pH=7.0 with HCl). The suspension was first centrifuged at 950×g for 6 minutes. The resulting pellet is resuspended in the same buffer, and the suspension is centrifuged at 700×g for 6 minutes. The resulting pellet is resuspended in 5 ml of the same buffer. This suspension contains primarily large protoplasts and osmotically fragile cells that retain some cell wall structure. Compared to the small protoplasts removed by the above procedure, the percentage of protoplasts able to regenerate cell walls and percentage of viable osmotically stable cells is higher for the large protoplasts and osmotically fragile cells in the final suspension. The suspension of cells is diluted with buffer to a concentration of $\sim 2 \times 10^8$ cells/ml.

D. Transformation Procedure

For each transforming plasmid, an ~0.1 ml suspension of osmotically fragile *Penicillium chrysogenum* cells (approximately $2 \times 10^7$ cells) is supplemented with 10 μl of 50 mM $CaCl_2$, 25 μg of plasmid DNA in 5–15 μl of TE buffer, and 0.9 ml of a solution of freshly dissolved polyethylene glycol 4000 (Baker, 40% weight/volume in osmotically stabilized buffer). The mixture is vortexed, allowed to stand for 10 minutes at room temperature, centrifuged at 700×g for 2 minutes, and vortexed again. Two aliquots of 0.5 ml each are then spread on the surface of osmotically stabilized acetamide medium (1.7 g/L Yeast Nitrogen Base without amino acids and ammonium sulfate; 125 g/L sucrose, 0.738 g/L acetamide; 1.27 g/L $CaCl_2$; and 22 g/L Noble agar). To measure the total number of viable cells present in transformation mixtures, aliquots from the transformation mixture are plated on medium in which the acetamide is replaced with an equimolar amount of ammonium sulfate. Seven to ten days after transformation, transformant colonies of sufficient size to subculture are present on the acetamide medium. Abortive transformants are easily distinguished from stable transformants, because abortive transformants fail to grow upon subculture to fresh acetamide medium. Cells transformed with a plasmid containing the acetamidase gene form visible colonies in four to five days after transformation.

E. Analysis of *Penicillium chrysogenum*/p3SR2, *P. chrysogenum*/pPS52, and *P. chrysogenum*/pPS54 Transformants

*Penicillium chrysogenum*/p3SR2, *P. chrysogenum*/pPS52, and *P. chrysogenum*/pPS54 transformants express an acetamidase activity not detected in extracts of the untransformed recipient P. chrysogenum strain (e.g., ATCC 9480). This activity results in the ability of the transformed strains to grow using the ammonia released by acetamide hydrolysis when no other nitrogen sources are available. The ability of the transformants to grow on acetamide as sole nitrogen source indicates the functionality of the *Aspergillus nidulans* acetamidase gene in *P. chrysogenum*.

Stable transformants carry the transforming DNA in their high molecular weight DNA. Probes, e.g., plasmid pBR322 or fragments of Aspergillus DNA that contain the acetamidase gene, hybridize to the high molecular weight DNA from these transformants even after multiple passage on non-selective medium (ammonia as nitrogen source). The transforming phenotype (ability to grow on acetamide as sole nitrogen source) is also maintained by the transformants after passage on non-selective medium.

Plasmids containing the acetamidase gene are particularly useful as vectors for inserting genes into *Penicillium chrysogenum,* because no special recipient strain, such as an auxotroph, need be constructed, owing to the natural inability of *P. chrysogenum* to grow on acetamide as sole nitrogen source. Transformation systems based on complementation of auxotrophic markers by a gene in the transforming plasmid do not share this advantage. Frequently, pleiotropic mutations are associated with the introduction of an auxotrophic marker into a *P. chrysogenum* strain highly developed for penicillin production. Such mutations usually result in lower penicillin production (MacDonald et al., 1963, J. Gen. Microbiol. 33: 365–374).

Plasmid pPS54 contains the *Penicillium chrysogenum* IPS gene. Plasmid pPS54 and derivatives of plasmid pPS54 that differ by replacement of the promoter of the *Aspergillus nidulans* acetamidase gene with the promoter from the the *P. chrysogenum* IPS gene can be used to generate Penicillium strains with higher penicillin V titers than their untransformed parents, owing to the greater production of IPS in the transformants. IPS functions in the biosynthetic pathway to penicillin V. The relative effectiveness of the plasmids in constructing overproducing strains for IPS and penicillin V depends on the parent plasmid: derivatives of plasmid pPS54 that differ from plasmid pPS54 by replacement of the promoter of the *A. nidulans* acetamidase gene with the promoter from the the *P. chrysogenum* IPS gene can produce transformants at higher frequency than does plasmid pPS54.

EXAMPLE 19

Genetic Transformation of *Penicillium chrysogenum* with Plasmids pPS55 and pPS57

A. Preparation of Penicillium protoplasts

Preparation of the *Penicillium chrysogenum* protoplasts is the same as that described in Example 18.

B. Transformation Procedure

For each transforming plasmid, an ~0.1 ml suspension of osmotically fragile *Penicillium chrysogenum* cells (approximately $2\times10^7$ cells) is supplemented with 10 µl of 50 mM $CaCl_2$; 25 µg of plasmid DNA in 5–15 µl of TE buffer, and a solution of freshly dissolved polyethylene glycol 4000 (Baker, 40% weight/volume in osmotically stabilized buffer). The mixture is vortexed, allowed to stand for 10 minutes at room temperature, centrifuged at 700×g for 2 minutes, and vortexed again. Two aliquots of 0.5 ml each are then delivered to and spread on the surface of osmotically stabilized base medium (yeast nitrogen base without amino acids (Difco), 1.7 g/L; ammonium sulfate, 2 g/L; sucrose, 125 g/L; $CdCl_2$, 3 mM; trifluoroperizine, 250–500 µM; Noble agar, 22 g/L). After the petri plates are incubated at 15° C. for 24 hours, 4 ml of liquified Noble agar (0.50% w/v at 42° C.) containing 1.0 M KCl and enough hygromycin B to achieve a final plate concentration of 250–500 µg/ml are added to each petri dish. After the overlay has solidified, the petri plates are incubated at 25° C. in a humidified chamber. To measure the total of viable cells present in the transformation mixture, aliquots from the transformation mixture are plated on base medium with no overlays. Fourteen to twenty one days after transformation, transformant colonies of sufficient size to subculture are present on selective medium (base medium with hygromycin B overlay). Abortive transformants are easily distinguished from stable transformants, because abortive transformants fail to grow upon subculture to base medium supplemented with 250–500 µg/ml of hygromycin B. Cells transformed with a plasmid containing the hybrid HmR gene (utilizing the pIPSp promoter) form visible colonies in seven to ten days after transformation. The presence of trifluoroperizine and cadmium chloride in the base medium increases the sensitivity of *P. chrysogenum* cells to hygromycin B.

C. Analysis of *Penicillium chrysogenum*/pPS55 and *P. chrysogenum*/pPS57 Transformants

*Penicillium chrysogenum*/pPS55 and *P. chrysogenum*/pPS57 express a hygromycin B phosphotransferase activity not detected in extracts of untransformed *P. chrysogenum* (e.g., ATCC 9480). This activity results in the ability of the transformed strains to grow in the presence of toxic concentrations of hygromycin B (with entry of hygromycin B into the fungal cells facilitated by exposure to cadmium ion and trifluoroperizine [TFP]). The ability of the transformants to grow in the presence of toxic concentrations of hygromycin B (potentiated by cadmium and TFP) indicates that the hybrid HmR gene functions gene in *P. chrysogenum.* The higher transformation frequencies obtained with plasmid pPS57, as compared to plasmid pPS55, indicate that the promoter and 5' regulatory sequences of the *P. chrysogenum* IPS work better in *P. chrysogenum* than do the promoter and 5' regulatory sequences of the *Cephalosporium acremonium* IPS gene, present in the hybrid HmR genes carried by plasmid pPS55.

Stable *Penicillium chrysogenum*/pPS55 and *P. chrysogenum*/pPS57 transformants carry the transforming DNA in their high molecular weight DNA. Probes that contain no *P. chrysogenum* DNA but do contain sequences in common with the transforming DNA of plasmids pPS55 and pPS57 hybridize to the high molecular weight DNA from *P. chrysogenum*/pPS55 and *P. chrysogenum*/pPS57 transformants, even when the DNA is analyzed after the transformants are grown on non-selective medium (no hygromycin B present). The transforming phenotype (ability to grow in the presence of concentrations of hygromycin B that kill the untransformed recipient *P. chrysogenum* strain) is maintained after passage on non-selective medium.

Plasmids containing the hybrid HmR genes are particularly useful as vectors for inserting genes into Penicillium, especially *P. chrysogenum,* because no special recipient strain, such as an auxotroph, need be constructed, owing to the natural inability of Penicillium to grow in the presence of hygromycin B and compounds that enhance the susceptibility of Penicillium to hygromycin B, i.e., cadmium ion and trifluoroperizine as described above.

Derivatives of plasmids pPS55 and pPS57 that contain the *P. chrysogenum* IPS gene can be used to generate strains with penicillin V titres superior to their untransformed parents owing to the greater production of IPS in the transformants.

EXAMPLE 20
Genetic Transformation of *Penicillium chrysogenum* with Plasmids pPS62 and pPS61
A. Transformation Procedure Preparation of inoculum for cell culture, preparation of *Penicillium chrysogenum* protoplasts, and the tranformation procedures for using plasmid pPS62 or pPS61 to transform *P. chrysogenum* are the same as those described in Examples 18 and 19. Plasmid pPS62 contains the HmR gene as a selectable marker; plasmid pPS61 contains the amdS gene as a selectable marker.

B. Analysis of *Penicillium chrysogenum*/pPS62 and *P. chrysogenum*/pPS61 Transformants Stable *Penicillium chrysogenum*/pSP62 and *P. chrysogenum*/pPS61 transformants carry the transforming DNA in their high molecular weight DNA. The transforming phenotype is maintained after passage on non-selective medium.

Plasmids pPS62 and pPS61 contain a hybrid DACS/DAOCS gene constructed by splicing the promoter from the *Penicillium chrysogenum* IPS gene to the coding sequence of the *Cephalosporium acremonium* DACS/DAOCS gene. The native and hybrid genes each code for the synthesis of both deacetoxycephalosporin C synthetase (expandase) and deacetylcephalosporin C synthetase (hydroxylase). The enzyme activities are defined, respectively, by the catalysis of penicillin N to deaceatoxycephalosporin C (expandase) and deacetoxycephalosporin C to deacetylcephalosporin C (hydroxylase). Extracts of *P. chrysogenum*/pPS61 and *P. chrysogenum*/pPS62 transformants exhibit expandase and hydroxylase activities. These activities are not found in extracts of the untransformed *P. chrysogenum* strains. The promoter and the translational activating sequence from the *P. chrysogenum* IPS gene present in the hybrid DACS/DAOCS gene of plasmids pPS61 and pPS62 function in *P. chrysogenum* to allow expression of expandase and hydroxylase activities in *P. chrysogenum*.

*Penicillium chrysogenum*/pPS61 and *P. chrysogenum*/pPS62 transformants are useful as intermediates in the construction of *P. chrysogenum* strains that produce cephalosporins. Intermediate strains of *P. chrysogenum* that produce expandase or expandase and hydroxylase can be treated with mutagens and mutagenized cells selected for ability to produce cephalosporins. Alternatively, derivatives of plasmids pPS61 or pPS62 that contain a modified expandase/hydroxylase gene that encodes an expandase that converts penicillin V to cephalosporin V, but lacks information necessary to encode hydroxylase, can be produced. The modified gene is made by in vitro mutagenesis of the cloned *C. acremonium* expandase/hydroxylase coding sequence in *E. coli*. The derivative plasmids that carry the modified DACS/DAOCS gene are used to transform *P. chrysogenum* as desribed above. Such transformants produce cephalosporin V when precursed with phenoxyacetic acid and are useful because they produce cephalosporin V in high yield. Cephalosporin V is readily and inexpensively extracted into organic solvents at low pH, thereby facilitating its isolation. Cephalosporin V, so produced, represents a useful intermediate for conversion to inexpensive, high-quality 7-ACA for use in the manufacture of semisynthetic cephalosporins.

EXAMPLE 21
Genetic Transformation of *Cephalosporium acremonium* with Plasmid pPS56
A. *Cephalosporium acremonium* Strains The preferred Cephalosporium strain for transformation is obtained from the American Type Culture Collection under the accession number ATCC 11550. Other Cephalosporium strains or any commercial strains derived from ATCC 11550 by mutation, selection, or genetic breeding for the purpose of improved production of cephalosporin C are also suitable for use in preparing transformants with the vectors and plasmids of the present invention.

B. Preparation of Inoculum for Cell Culture

To transform *Cephalosporium acremonium* cells efficiently, it is necessary to remove the cell walls to form stable protoplasts. In the preparation of such protoplasts, it is highly advantageous to begin with a uniform inoculum. Otherwise, preparation of cells in culture is not reproducible, and time is lost by attempts to prepare *C. acremonium* protoplasts from unsuitable or inadequate amounts of cells.

C. Preparation of Uniform Inoculum for Cell Culture

An ampoule of spores (approximately $10^9$ conidia in 1.5 ml of preservation menstrum: 5% lactose, 10% glycerol, and 0.1% Tween 80), either lyophilized or taken from liquid nitrogen storage and thawed at room temperature, are diluted in 5 ml of sterile saline. About 0.1 ml of this suspension is used to inoculate each of approximately 50 slants containing 20 ml of Trypticase Soy Agar (BBL) medium. Before inoculation, the medium is allowed to dry until surface moisture is no longer visible. Inoculated slants are incubated for about four days at 25° C. About 10 ml of preservation menstrum are added to the mycelial growth that covers the surface of the medium in each slant. The slants are vortexed to suspend the conidia, and the conidial suspension from each slant is pooled and 10 ml aliquots frozen at −80° C. The frozen conidial suspension slowly loses viability and should not be used after about three months of storage at −80° C.

D. Growth of Cells for Preparation of Protoplasts

Approximately 106 ml of aqueous medium in a 500 ml shake flask are inoculated with cells from the 10 ml of frozen conidial suspension. Cells are obtained by centrifugation (10 min×2600 rpm) and then directly suspended in the aqueous culture medium. Decantation of the supernatant is necessary prior to suspension, because the lactose and glycerol adversely affect the growth of cells. The flask containing the suspended cells is placed on a gyrotory water-bath shaker and incubated at 29–30° C. for 24 hours at 285 rpm with a 1 inch throw. The recommended temperature of 29–30° C. in the culturing step is especially preferred for preparing transformable protoplasts, but lower temperatures of about 25° C. are also suitable. Those familiar with the art will recognize that 29–30° C. is different from the temperature (25° C.) preferred for culturing *Cephalosporium acremonium* for purposes of antibiotic production.

E. Preparation of Protoplasts

Cells from a 24 hour culture are harvested by suction filtration (Whatman #1 paper in a Buchner funnel) and suspended in an osmotically stabilized buffer (0.8 M NaCl; 0.1 M $MgSO_4$; and 10 mM $NaH_2PO_4$, pH=7.0) to which the reducing agent dithiothreitol has been added to a concentration of 0.05 M. Sufficient buffer is added to obtain a final cell concentration of 1 g (weighed after suction filtration) of cell mass per 20 ml of buffer. The cell suspension is placed on a gyrotory water-bath shaker in a 50 ml flask and incubated at 29–30° C. for 10 minutes at 140 rpm with a 1 inch throw. Alternatively, 2-mercaptoethanol, at a final concentration of 140 mM, may be used as a reducing agent. Dithiothreitol-treated cells are harvested by centrifugation and resuspended in an enzyme solution (10 mg/ml Novozym 234 from Novo Biolabs, Bagsvaerd, Denmark; 0.8 M NaCl; 0.1 M $MgSO_4$; 10 mM $NaH_2PO_4$; and pH=5.8) in a 250 ml Erlenmeyer flask. The final cell concentration is 1 g of treated cell mass per 10 ml of enzyme solution. The cell suspension is then placed on a gyrotory water-bath shaker at 29–30° C. for 15–30 minutes at 120 rpm with a 1 inch throw. At the end of this period, the protoplast suspension is transferred to a disposable centrifuge tube and vortexed for 2–3 seconds to liberate protoplasts still associated with mycelial fragments. This digestion procedure produces a heterogenous population of protoplasts with respect to size. The largest protoplasts regenerate cell walls and transform at a higher frequency than smaller protoplasts. A population of protoplasts enriched for large protoplasts is harvested by centrifugation at 100×g for 2 minutes in a table-top clinical centrifuge. The supernatant is discarded, and the pelleted protoplasts are washed by resuspension in the osmotically stabilized buffer (pH=7.0) and harvested by centrifugation (550×g for 6 minutes). The washing procedure is repeated two times. The washed protoplasts are resuspended in a sufficient amount of 0.8 M NaCl to achieve a concentration of 2 to $3 \times 10^9$ protoplasts per ml, by hemacytometer count.

F. Transformation Procedure

For each plasmid to be transformed, a 0.1 ml suspension containing 1 to $5 \times 10^7$ protoplasts of Cephalosporium in 0.8 M NaCl and 80 mM $CaCl_2$, is used. About 20 μg of plasmid and polyethylene glycol 4000 are added, as described in Example 18, to the suspension of protoplasts to achieve a transformation mixture volume of 1.1 ml. The mixture is incubated for 10 minutes at room temperature and then centrifuged at 100×g for 5 minutes. The protoplasts are then vortexed back into suspension in the same liquid. Aliquots (0.1 ml) are delivered to the surface of Trypticase-Soy Agar medium (BBL) that has been enriched with 10.8% sucrose to osmotically stabilize the protoplasts. After incubation of the petri plates at 15° C. for 24 hours, 4 ml of liquified agar (0.41% w/v, at 42° C.) containing 0.8 M NaCl and sufficient hygromycin B to achieve a final concentration of 100 μg/ml are added to each petri plate. C. acremonium strains exhibiting slow growth rates due to extensive mutagenesis are subjected to a reduced level of hygromycin B during the selection procedure (i.e., 10 μg/ml final concentration). After the overlay has solidified, the petri plates are incubated at 25° C. in a humidified chamber. Transformant colonies of sufficient size to subculture are present after four to five days incubation; however, slower growing transformants may take as long as 8 days to develop. Abortive transformants are easily distinguished from stable transformants, because abortive transformants fail to grow upon subculture to fresh medium containing the original selective level of hygromycin B.

G. Analysis of Cephalosporium acremonium/pPS56 Transformants

Stable Cephalosporium acremonium/pPS56 transformants carry the transforming DNA in their high molecular weight DNA. The transforming phenotype of such transformants (the ability to grow in the presence of concentrations of hygromycin B that kill the untransformed recipient C. acremonium strain) is maintained after growth on non-selective medium.

Plasmid pPS56 is particularly effective in inserting multiple copies of the DACS/DAOCS gene into the Cephalosporium acremonium high molecular weight DNA, because it contains a hybrid HmR gene that functions as a dominant selectable marker in C. acremonium. No special recipient strains, such as auxotrophs, need to be used as parent strains in transformations employing pPS56, owing to the natural inability of C. acremonium to grow in the presence of hygromycin B as specified above. No additives, e.g., cadmium ion or trifluoroperizine, need be added to enhance sensitivity of C. acremonium to hygromycin B.

Plasmid pPS56 can be used to generate strains of Cephalosporium acremonium with cephalosporin C titers higher than untransformed strains, due to extra copies of the DAOCS/DACS gene. The extra gene copies cause higher DAOCS/DACS activities, which promote increased synthesis of cephalosporin C. Strains of C. acremonium producing large amounts of cephalosporin C and significant amounts of penicillin N are particularly useful parent strains for transformations employing plasmid pPS56 to obtain transformants that more efficiently convert penicillin N into cephalosporin C. The desired C. acremonium/pPS56 transformants bear the transforming DNA as inserts in regions neutral with respect to growth and antibiotic production so that only the effect of increased DAOCS and DACS on cephalosporin C synthesis occurs. C. acremonium/pPS56 transformants with improved cephalosporin C production are useful in the manufacture of clinically significant cephalosporin antibiotics, such as cephalothin sodium, cefamandole nafate, and cefazolin sodium.

The CAT gene present on plasmid pPS56 is an important facet of the utility of plasmid pPS56 in transformations designed to create strains that exhibit increased cephalosporin C production. Large amounts of the plasmid may be conveniently obtained from E. coli transformed with plasmid pPS56 and selected for resistance to chloramphenicol. In addition, the CAT gene product is suitable for obtaining Cephalosporium acremonium transformants that overproduce β-lactam antibiotics. Although bacterial regulatory signals are usually not expressed in eucaryotic cells, there have been reports of low level expression of some bacterial genes, in particular β-lactamase genes, in eucaryotic cells. Unlike β-lactamases, the CAT gene product does not destroy β-lactam antibiotics. Hence the use of the CAT gene as a selectable marker is preferred.

We claim:

1. A recombinant DNA sequence that encodes a Cephalosporium deacetoxycephalosporin C synthetase/hydroxylase polypeptide of the structure:

$H_2N$-MET THR SER LYS VAL PRO VAL PHE ARG LEU ASP ASP

LEU LYS SER GLY LYS VAL LEU THR GLU LEU ALA GLU ALA

VAL THR THR LYS GLY ILE PHE TYR LEU THR GLU SER GLY

LEU VAL ASP ASP ASP HIS THR SER ALA ARG GLU THR CYS

VAL ASP PHE PHE LYS ASN GLY SER GLU GLU GLU LYS ARG

ALA VAL THR LEU ALA ASP ARG ASN ALA ARG ARG GLY PHE

SER ALA LEU GLU TRP GLU SER THR ALA VAL VAL THR GLU

THR GLY LYS TYR SER ASP TYR SER THR CYS TYR SER MET

GLY ILE GLY GLY ASN LET PHE PRO ASN ARG GLY PHE GLU

```
ASP VAL TRP GLN ASP TYR PHE ASP ARG MET TYR GLY ALA

ALA LYS ASP VAL ALA ARG ALA VAL LEU ASN SER VAL GLY

ALA PRO LEU ALA GLY GLU ASP ILE ASP ASP PHE VAL GLU

CYS ASP PRO LEU LEU ARG LEU ARG TYR PHE PRO GLU VAL

PRO GLU ASP ARG VAL ALA GLU GLU GLU PRO LEU ARG MET

GLY PRO HIS TYR ASP LEU SER THR ILE THR LEU VAL HIS

GLN THR ALA CYS ALA ASN GLY PHE VAL SER LEU GLN CYS

GLU VAL ASP GLY GLU PHE VAL ASP LEU PRO THR LEU PRO

GLY ALA MET VAL VAL PHE CYS GLY ALA VAL GLY THR LEU

ALA THR GLY GLY LYS VAL LYS ALA PRO LYS HIA ARG VAL

LYS SER PRO GLY ARG ASP GLN ARG VAL GLY SER SER ARG

THR SER SER VAL PHE PHE LEU ARG PRO LYS PRO ASP PHE

SER PHE ASN VAL GLN GLN SER ARG GLU TRP GLY PHE ASN

VAL ARG ILE PRO SER GLU ARG THR THR PHE ARG GLU TRP

LEU GLY GLY ASN TYR VAL ASN MET ARG ARG ASP LYS PRO

ALA ALA ALA GLU ALA ALA VAL PRO ALA ALA ALA PRO VAL

SER THR ALA ALA PRO ILE ALA THR-COOH
``` wherein ALA is an alanine residue, ARG is an arginine residue, ASN is an asparagine residue, ASP is an aspartic acid residue, CYS is a cysteine residue, GLN is a glutamine residue, GLU is a glutamic acid residue, GLY is a glycine residue, HIS is a histidine residue, ILE is an isoleucine residue, LEU is a leucine residue, LYS is a lysine residue, MET is a methionine residue, PHE is a phenylalanine residue, PRO is a proline residue, SER is a serine residue, THR is a threonine residue, TRP is a tryptophan residue, TYR is a tyrosine residue, and VAL is a valine residue.

2. The recombinant DNA sequence of claim 1 that is:

```
                5'-ATG ACT TCC AAG GTC CCC

GTC TTT CGT CTC GAC GAC CTC AAG AGC GGC AAG GTC

CTC ACC GAG CTC GCC GAG GCC GTC ACC ACC AAG GGT

ATC TTC TAC TTG ACC GAG AGC GGC CTG GTC GAC GAC

GAC CAC ACC TCG GCG CGT GAG ACG TGC GTT GAC TTT

TTC AAG AAC GGA AGC GAG GAG GAG AAG AGG GCC GTG

ACG CTC GCC GAC CGT AAC GCC CGC CGC GGC TTC TCT

GCC CTC GAG TGG GAG AGC ACC GCC GTC GTC ACC GAG

ACG GGC AAG TAC TCG GAC TAC TCG ACG TGC TAC TCC

ATG GGC ATC GGC GGC AAC CTG TTC CCG AAC CGG GGC

TTC GAG GAC GTC TGG CAG GAC TAC TTC GAC CGC ATG

TAC GGC GCA GCC AAG GAT GTC GCG CGC GCC GTT CTC

AAC TCT GTG GGC GCC CCG CTC GCC GGG GAG GAC ATT

GAT GAC TTC GTC GAG TGC GAT CCC CTC CTC CGC CTA

CGG TAC TTC CCC GAA GTG CCG GAG GAC CGC GTC GCC

GAA GAG GAA CCC CTC CGC ATG GGA CCC CAC TAC GAC

CTA TCG ACC ATC ACG CTC GTG CAC CAG ACA GCC TGC

GCC AAC GGC TTC GTG AGC CTG CAG TGC GAG GTG GAC

GGA GAA TTC GTC GAC CTC CCG ACG CTC CCC GGC GCC

ATG GTC GTC TTC TGC GGC GCG GTC GGC ACC CTG GCC

ACG GGC GGC AAG GTC AAG GCG CCC AAG CAC CGG GTC

AAG TCT CCC GGG CGC GAC CAG CGC GTC GGC AGC AGC

CGC ACG TCG AGC GTC TTC TTC CTG CGG CCG AAG CCC

GAC TTC AGC TTC AAC GTG CAG CAG TCG AGG GAG TGG

GGT TTC AAC GTC CGC ATC CCG TCG GAG CGC ACG ACG

TTC AGG GAG TGG CTT GGC GGG AAC TAT GTC AAC ATG

CGG AGG GAT AAG CCG GCG GCA GCG GAG GCG GCT GTC

CCC GCG GCT GCC CCT GTC TCT ACC GCA GCT CCT ATA

GCC ACT-3'
``` wherein A is deoxyadenyl, G is deoxyguanyl, C is deoxycytidyl, and T is thymidyl.

3. A recombinant DNA vector that comprises the DNA sequence of claim 1.

4. A recombinant DNA expression vector of claim 3 that further comprises a promoter and a translational activating sequence positioned to drive expression of a DNA sequence encoding the polypeptide having the amino acid sequence set forth in claim 1.

5. The recombinant DNA expression vector of claim 4, wherein said promoter functions in E. coli.

6. The recombinant DNA expression vector of claim 5, wherein said promoter is the λpL promoter.

7. The recombinant DNA expression vector of claim 6 that is plasmid pIT507.

8. The recombinant DNA expression vector of claim 6 that is plasmid pIT511.

9. The recombinant DNA expression vector of claim 4, wherein said promoter functions in Penicillium.

10. The recombinant DNA expression vector of claim 9, wherein said promoter is the promoter of the Penicillium chrysogenum IPS gene.

11. The recombinant DNA expression vector of claim 10 that is plasmid pPS58.

12. The recombinant DNA expression vector of claim 10 that is plasmid pPS59.

13. The recombinant DNA expression vector of claim 10 that is plasmid pPS60.

14. The recombinant DNA expression vector of claim 10 that is plasmid pPS61.

15. The recombinant DNA expression vector of claim 10 that is plasmid pPS62.

16. The recombinant DNA expression vector of claim 4, wherein said promoter functions in Cephalosporium.

17. The recombinant DNA expression vector of claim 16 wherein said promoter is the promoter of a Cephalosporium acremonium gene encoding the polypeptide having the amino acid sequence set forth in claim 1.

18. The recombinant DNA expression vector of claim 17 that is pIT503.

19. The recombinant DNA expression vector of claim 17 that is pPS52.

20. The recombinant DNA expression vector of claim 17 that is pPS56.

21. The recombinant DNA expression vector that is plasmid pIT513.

22. A recombinant DNA sequence comprising the promoter and translational activating sequence of a Cephalosporium gene encoding the polypeptide having the amino acid sequence set forth in claim 1.

23. The DNA sequence of claim 22 that is:

```
5'-A AGC TTG TAC GGA GAA TTA AGG CTT GCA CGA TTC

CAT GGC GGT CTC GAC GAT CAG GGA CCA TGC ACG ATA

CAT ATT CTC CTG CGA ACC AAG AAC GAG AAG AGA ACT

CGA TGG CTT CTT ATG ATT CGT TGA CAA AAC TTC ACA

AGA CAC TCG TGG GTT TAC AAT GCT ACA TTG ACG TGT

GCG GCC AAG GCT GAG GGG AAG CAG GGC GTC ACT TAC

GGC TAA GTA GCA GTT GTC TAA AAA GGA GTT CCT CGG CGT

AAG CTA CGA GGT GGG GTT TGA GAT ATA TAT ATA CCG

CTT TGA CAA CGT TTC GTT CTC ACT GGG ATC TTG TGA

ATC CTT AAA TTC CTC TTG CAG AAC TTT CCT CCA CGC

TAC TCC TCT CAA GTC ATC GCT CAA AAC CAC AGC ATC

AAC ATG-3'
``` wherein A is deoxyadenyl, G is deoxyguanyl, C is deoxycytidyl, and T is thymidyl.

24. A recombinant DNA vector comprising the DNA sequence of claim 22.

25. A recombinant DNA sequence comprising the 3' regulatory DNA sequence of a Cephalosporium gene encoding the polypeptide having the amino acid sequence set forth in claim 1 wherein the 3' regulatory DNA sequence is:

```
5' - TAG GGA ACC CGC CGA TCG AGT AAT AAA TCT ACG

GGA GTT TAA GAA GAA AAA TTG CCC TAT AAA TTG CTA

AAT TTT TAA AAC ACA AAG CAT GAG TGT CAA GAG TTT

CAA GTT TCA A - 3'
``` wherein A is deoxyadenyl, G is deoxyguanyl, C is deoxycytidyl, and T is thymidyl.

26. A recombinant DNA vector that comprises the DNA sequence of claim 25.

27. A method for expressing a *Cephalosporium deacetoxycephalosporin* C synthetase/hydroxylase polypeptide in a recombinant host cell, said method comprising:
  (1) transforming said host cell with a recombinant DNA expression vector that comprises:
    (a) a promoter and translational activating sequence that functions in said host cell; and
    (b) a DNA sequence of claim 1 that encodes a *Cephalosporium deacetoxycephalosporin* C synthetase/hydroxylase polypeptide and is positioned for expression from said promoter; and
  (2) culturing said host cell transformed in step (1) under conditions that allow for expression of said *Cephalosporium deacetoxycephalosporin* C synthetase/hydroxylase polypeptide.

28. The method of claim 27, wherein said recombinant host cell is selected from the group consisting of *E. coli*, Cephalosporium, and Penicillium.

29. The method of claim 28, wherein said recombinant host cell cultured in step 2 is *E. coli*.

30. The method of claim 29, wherein said recombinant host cell cultured in step 2 is selected from the group consisting of *E. coli* K12 JM109/pIT507 and *E. coli* K12 JM109/pIT511.

31. The method of claim 28, wherein said recombinant host cell cultured in step 2 is Penicillium.

32. The method of claim 31, wherein said recombinant host cell cultured in step 2 is *Penicillium chrysogenum*/pPS59.

33. The method of claim 31, wherein said recombinant host cell cultured in step 2 is *Penicillium chrysogenum*/pPS61.

34. The method of claim 31, wherein said recombinant host cell cultured in step 2 is *Penicillium chrysogenum*/pPS62.

35. The method of claim 28, wherein said recombinant host cell cultured in step 2 is Cephalosporium.

36. The method of claim 35, wherein said recombinant host cell cultured in step 2 is *Cephalosporium acremonium*/pIT503.

37. The method of claim 35, wherein said recombinant host cell cultured in step 2 is *Cephalosporium acremonium*/pPS52.

38. The method of claim 35, wherein said recombinant host cell cultured in step 2 is *Cephalosporium acremonium*/pPS56.

39. A method for producing a cephalosporin in a Penicillium host cell that comprises transforming said host cell with a recombinant DNA expression vector that comprises a gene that codes for the polypeptide having the amino acid sequence set forth in claim 1.

40. A recombinant host cell transformed with a recombinant DNA vector that comprises a DNA sequence of claim 1.

41. The transformed host cell of claim 40 that is *E. coli* K12.

42. The transformed host cell of claim 41 that is *E. coli* K12 JM109/pIT503.

43. The transformed host cell of claim 41 that is *E. coli* K12 JM109/pIT507.

44. The transformed host cell of claim 41 that is *E. coli* K12 JM109/pIT511.

45. The transformed host cell of claim 40 that is *Penicillium chrysogenum*.

46. The transformed host cell of claim 45 that is *Penicillium chrysogenum*/pPS59.

47. The transformed host cell of claim 45 that is *Penicillium chrysogenum*/pPS61.

48. The transformed host cell of claim 45 that is *Penicillium chrysogenum*/pPS62.

49. The transformed host cell of claim 40 that is *Cephalosporium acremonium*.

50. The transformed host cell of claim 49 that is *Cephalosporium acremonium*/pIT503.

51. The transformed host cell of claim 49 that is *Cephalosporium acremonium*/pPS52.

52. The transformed host cell of claim 49 that is *Cephalosporium acremonium*/pPS56.

53. A recombinant DNA vector selected from the group consisting of plasmids pPS51, pPS53, pPS54, pPS55, and pPS57.

* * * * *